US008889131B2

(12) United States Patent
Aikawa et al.

(10) Patent No.: US 8,889,131 B2
(45) Date of Patent: Nov. 18, 2014

(54) NOTCH INHIBITION IN THE TREATMENT AND PREVENTION OF A METABOLIC DISEASE OR DISORDER AND CARDIOVASCULAR COMPLICATIONS THEREOF

(75) Inventors: Masanori Aikawa, Chestnut Hill, MA (US); Daiju Fukuda, Brookline, MA (US); Tetsuro Miyazaki, Brookline, MA (US); Elena Aikawa, Chestnut, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 13/461,365

(22) Filed: May 1, 2012

(65) Prior Publication Data
US 2013/0064832 A1 Mar. 14, 2013

Related U.S. Application Data

(63) Continuation-in-part of application No. PCT/US2010/054798, filed on Oct. 29, 2010.

(60) Provisional application No. 61/257,026, filed on Nov. 1, 2009.

(51) Int. Cl.
*A61K 39/395* (2006.01)
*C07K 16/22* (2006.01)
*C07K 14/475* (2006.01)
*A61K 38/17* (2006.01)
*C12N 15/113* (2010.01)
*A61K 39/00* (2006.01)

(52) U.S. Cl.
CPC ............. *A61K 38/1709* (2013.01); *C07K 16/22* (2013.01); *C12N 15/113* (2013.01); *C12N 15/1138* (2013.01); *A61K 2039/505* (2013.01); *C07K 2317/76* (2013.01); *C12N 2310/14* (2013.01)
USPC .................... 424/130.1; 424/158.1; 530/350; 530/399; 530/387.1

(58) Field of Classification Search
None
See application file for complete search history.

(56) References Cited

U.S. PATENT DOCUMENTS

| | | | |
|---|---|---|---|
| 5,703,129 A | 12/1997 | Felsenstein et al. |
| 6,448,229 B2 | 9/2002 | Teall |
| 6,683,091 B2 | 1/2004 | Asberom et al. |
| 6,703,221 B1 | 3/2004 | Chan et al. |
| 6,756,511 B2 | 6/2004 | Castro Pineiro et al. |
| 6,890,956 B2 | 5/2005 | Churcher et al. |
| 6,967,196 B1 | 11/2005 | Smith et al. |
| 6,984,626 B2 | 1/2006 | Nadin et al. |
| 6,995,155 B2 | 2/2006 | Churcher et al. |
| 7,161,006 B2 | 1/2007 | Crawforth et al. |
| 7,183,303 B2 | 2/2007 | Castro Pineiro et al. |
| 7,365,196 B2 | 4/2008 | Belanger et al. |
| 8,133,857 B2 | 3/2012 | Aikawa |
| 8,404,233 B2 | 3/2013 | Sunamura et al. |
| 2003/0180784 A1 | 9/2003 | McCarthy et al. |
| 2004/0102390 A1 | 5/2004 | Freier et al. |
| 2005/0025751 A1 | 2/2005 | Bodmer et al. |
| 2005/0026831 A1 | 2/2005 | Bodmer et al. |
| 2005/0075320 A1 | 4/2005 | Nadin et al. |
| 2005/0143369 A1 | 6/2005 | Castro Pineiro et al. |
| 2005/0227973 A1 | 10/2005 | Brown et al. |
| 2005/0261276 A1 | 11/2005 | Crawforth et al. |
| 2006/0004004 A1 | 1/2006 | Asberom et al. |
| 2006/0009467 A1 | 1/2006 | Josien et al. |
| 2006/0030694 A1 | 2/2006 | Kitajewski et al. |
| 2006/0194315 A1 | 8/2006 | Condie et al. |
| 2007/0213266 A1 | 9/2007 | Gill et al. |
| 2007/0213329 A1 | 9/2007 | Castro Pineiro et al. |
| 2008/0206753 A1 | 8/2008 | Eagan et al. |
| 2009/0137470 A1 | 5/2009 | Stylianou |
| 2009/0175849 A1 | 7/2009 | Aikawa |
| 2009/0232813 A1 | 9/2009 | Beauchamp et al. |
| 2010/0303812 A1 | 12/2010 | Sunamura et al. |
| 2013/0336958 A1 | 12/2013 | Aikawa |

FOREIGN PATENT DOCUMENTS

| | | |
|---|---|---|
| WO | WO 00/50391 A1 | 8/2000 |
| WO | WO 01/70677 A1 | 9/2001 |
| WO | WO 02/081435 A1 | 10/2002 |
| WO | WO 03/012441 A1 | 2/2003 |
| WO | WO 03/018543 A1 | 3/2003 |
| WO | WO 03/041735 A3 | 5/2003 |
| WO | WO 03/042246 A2 | 5/2003 |
| WO | WO 2005/008250 A1 | 1/2005 |
| WO | WO 2007/103114 A2 | 9/2007 |
| WO | WO 2008/139202 A1 | 11/2008 |
| WO | WO-2009025867 A2 * | 2/2009 |
| WO | WO 2010/021729 A2 | 2/2010 |

OTHER PUBLICATIONS

Fukuda et al. Notch ligand Delta-like 1 blockade attenuates atherosclerosis and metabolic disorders. Proc Natl Acad Sci USA 109(27): E1868-1877, 2012.*
Irabarren et al. Metabolic syndrome and early-onset coronary artery disease. J Am Coll Cardiol 48(9): 1800-1807, 2006.*
Malik et al. Impact of the metabolic syndrome on mortality from coronary heart disease, cardiovascular disease, and all causes in United States adults. Circulation 110: 1245-1250, 2004.*

(Continued)

*Primary Examiner* — Bridget E Bunner
(74) *Attorney, Agent, or Firm* — Law Office of: Michael A. Sanzo, LLC

(57) ABSTRACT

The present invention is directed to methods of treating or preventing a metabolic disease or disorder and cardiovascular complications and other complications thereof by administering agents that inhibit the NOTCH signaling pathway. In addition, the invention encompasses methods for determining whether a patient is at increased risk for developing these conditions by determining the amount, function, or activity of NOTCH pathway components in biological samples derived from the patient or in imaging analysis.

20 Claims, 51 Drawing Sheets

(56) References Cited

OTHER PUBLICATIONS

Sutherland e tal. The metabolic syndrome and inflammation. Metabolic Syndrome and Related disorders 2(2): 82-104 (plus 2 extra pages), 2004.*

Eckel et al. The metabolic syndrome. Lancet 365: 1415-1428, 2005.*

Subramanian et al. Dietary cholesterol worsens adipose tissue macrophage accumulation and atherosclerosis in obese LDL receptor-deficient mice. Arterioscler Thromb Vasc Biol 28: 685-691, 2008.*

Phillips, A.J. The challenge of gene therapy and DNA delivery. J Pharm Pharacol 53: 1169-1174, 2001.*

Pirollo et al. Targeted delivery of small interfering RNA: approaching effective cancer therapies. Cancer Res 68(5): 1247-1250, 2008.*

Rubanyi et al. The future of human gene therapy. Mol Aspects Med 22: 113-142, 2001.*

Rusanescu et al. Notch signaling in cardiovascular disease and calcification. Curr Cardiol Rev 4: 148-156, 2008.*

Li et al. Notch3 signaling promotes the development of pulmonary arterial hypertension. Nature Med 15(11): 1289-1297, 2009; published online Oct. 25, 2009.*

Clément, et al., "Notch3 and IL-1 βexert opposing effects on a vascular smooth muscle cell inflammatory pathway in which NF- κB drives crosstalk," J. Cell Sci. 120:3352-3361 (Sep. 2007).

Curry, et al., "Gamma secretase inhibitor blocks Notch activation and induces apoptosis in Kaposi's sarcoma tumor cells," Oncogene 24:6333-6344 (Jun. 2005).

De Strooper, et al., "A Presenilin-1-Dependent γ-Secretase-Like Protease Mediates Release of Notch Intracellular Domain," Nature 398:518-522 (Apr. 8, 1999).

Esposito, et al., "The metabolic syndrome and inflammation: association or causation?" Nutr. Metab. Cardiovasc. Dis. 14:228-232 (Oct. 2004).

Evin, et al., "A Synthetic Substrate Assay for the Gamma-Secretase of the β-A4 Amyloid of Alzheimer's Disease," J. Pept. Sci. 1(2):132-139 (Mar./Apr. 1995).

Fung, et al., "Delta-Like 4 Induces Notch Signaling in Macrophages: Implications for Inflammation," Circulation 115:2948-2956 (May 2007).

Fung, et al., "Induction of the Pathway in Activated Human Macrophages," Circulation 110(17):274, Supplement III, Abstract 1312 (Oct. 26, 2004).

Gale, et al., "Haploinsufficiency of delta-like 4 ligand results in embryonic lethality due to major defects in arterial and vascular development," Proc. Natl. Acad. Sci. USA 101(45):15949-15954 (Nov. 9, 2004).

Garg, et al., "Mutations in NOTCH1 Cause Aortic Valve Disease," Nature 437:270-274 (Sep. 2005).

Hartley, et al., "Expression of infectious murine leukemia viruses by RAW264.7 cells, a potential complication for studies with a widely used mouse macrophage cell line," Retrovirology 5:1-6 (published online Jan. 4, 2008).

High, et al., "The multifaceted role of Notch in cardiac development and disease,"Nature Rev. 9:49-61 (Jan. 2008).

Hofmann, et al., "Notch Signaling in Blood Vessels Who Is Talking to Whom About What?" Circ. Res. 100:1556-1568 (Jun. 2007).

Hoke, et al., "In Vitro Gama-Secretase Cleavage of the Alzheimer's Amyloid Precursor Protein Correlates to a Subset of Presenlin Complexes and is Inhibited by Zinc," FEBS J. 272:5544-5557 (published online Oct. 6, 2005).

Hotamisligil, "Inflammation and metabolic disorders," Nature444:860-867 (Dec. 2006).

Ikeuchi, et al., "The Notch Ligands, Delta1 and Jagged2, Are Substrates for Presenlin-Dependent "γ-Secretase" Cleavage," J. Biol. Chem. 278(10):7751-7754 (Mar. 7, 2003).

Iso, et al., "Notch Signaling in Vascular Development," Arterioscler. Thromb. Vasc. Biol. 23:543-553 (published online Feb. 2003).

Itoh, et al., "Synergy and Antagonism Between Notch and BMP Receptor Signaling Pathways in Endothelial Cells," EMBO J. 23(3):541-551 (published online Jan. 2004).

Kanda, et al., "MCP-1 contributes to macrophage infiltration into adipose tissue, insulin resistance and hepatic steatosis in obesity," J Clin. Invest. 116(6):1494-1505 (Jun. 2006).

Liang, et al., "The Macrophage at the Crossroads of Insulin Resistance and Atherosclerosis," Circ. Res. 100:1546-1555 (Jun. 2007).

Lindner, et al., "Members of the Jagged/NotchGene Families Are Expressed in Injured Arteries and Regulate Cell Phenotype via Alterations in Cell Matrix and Cell-Cell Interaction," Am. J. Pathol. 159(3):875-883 (Sep. 2001).

Mumm, et al., "A Ligand-Induced Extracellular Cleavage Regulates γ-Secretase-Like Proteolytic Activation of Notch1," Mol. Cell 5:197-206 (Feb. 2000).

Nobta, et al., "Critical Regulation of Bone Morphogenetic Protein-Induced Osteoblastic Differentiation by Delta1/Jagged1-Activated Notch1 Signaling," J. Biol. Chem. 280(16):15842-15848 (Apr. 22, 2005).

Peri, et al., "Development of Human Protein Reference Database as an Initial Platform for Approaching Systems Biology in Humans," Genome Res. 13(10):2363-2371 (Oct. 2003).

Pinnix, et al., "A Novel γ-Secretase Assay Based on Detection of the Putative C-Terminal Fragment-γof Amyloid β Protein Precursor," J. Biol. Chem. 276(1):481-487 (Jan. 5, 2001).

Poulos, et al., "Cell line models for differentiation: predipocytes and adipocytes," Exp. Biol. Med. 235:1185-1193 (published online Sep. 2010).

Radtke, et al., "Notch Signaling in the Immune System," Immunity 32:14-27 (Jan. 29, 2010).

Selkoe, et al., "Notch and Presenlin: Regulated Intrmembrane Proteolysis Links Development and Degenration," Annu. Rev. Neurosci. 26:565-597 (2003) (First published online as a Review in Advance on Apr. 18, 2003).

Sernee, et al., "Selecting Cells with Different Alsheimer's Disease γ-Secretase Activity Using FACS," Eur. J. Biochem. 270:495-506 (published online Jan. 2003).

Shimizu, et al., "Physical Interaction of Delta1, Jagged1, and Jagged2 with Notch1 and Notch3 Receptors," Biochem. Biophys. Res. Commun. 276:385-389 (Sep. 2000).

Shimizu, et al., "Mouse Jagged1 Physically Interacts with Notch2 and Other Notch Receptors," J. Biol. Chem. 274(46):32961-32969 (Nov. 12, 1999).

Shimizu, et al., "Notch Signaling Induces Osteogenic Differentiation and Mineralization of Vascular Smooth Muscle Cells," Arterioscler. Thromb. Vasc. Biol. 29:1104-1111 (published online Apr. 2009).

Stockhausen, et al., "Effects of the Histone Deacetylase Inhibitor Valproic Acid on Notch Signaling in Human Neuroblastoma Cells," Br. J. Cancer 92:751-759 (Published online Feb. 1, 2005).

Swirski, et al.,"Ly-6C$^{hi}$monocytes dominate hypercholesterolemia-associated monocytosis and give rise to macrophages in atheromata," J. Clin. Invest. 117(1):195-205 (Jan. 2007).

Takizawa, et al., "Enhanced Gene Activation by Notch and BMP Signaling Cross-Talk," Nucleic Acids Res. 31(19):5723-5731 (Oct. 2003).

Towler, et al., "Oxidation, Inflammation, and Aortic Valve Calcification," J. Am. Coll. Cardiol. 52(10):851-854 (Sep. 2008).

Van Es, et al., "Notch/γ-Secretase Inhibition Turns Proliferative Cells in Intestinal Crypts and Adenomas into Goblet Cells," Nature 435:959-963 (Jun. 2005).

Wang, et al., "μOpiate Receptor: cDNA Cloning and Expression," Proc. Natl. Acad. Sci. USA 90:10230-10234 (Nov. 1993).

Weng, et al., "Activating Mutations of NOTCH1 in Human T Cell Acute Lymphoblastic Leukemia," Science 306:269-271 (Oct. 8, 2004).

Williams, et al., "Up-regulation of the Notch ligand Delta-like 4 inhibits VEGF-induced endothelial cell function," Blood 107(3):931-939 (Feb. 1, 2006).

Xu, et al., "Gamma-Secretase: Characterization and Implication for Alzheimer Disease Therapy," Neurobiol. Aging 23(6):1023-1030 (2002) (Nov.-Dec. 2002).

U.S. Appl. No. 13/903,288, filed May 28, 2013.

International Search Report for PCT/US2010/054798 filed Oct. 29, 2010.

Written Opinion of the International Searching Authority for PCT/US2010/054798 filed Oct. 29, 2010.

(56) References Cited

OTHER PUBLICATIONS

International Preliminary Report on Patentability for PCT/US2010/054798 filed Oct. 29, 2010.

Supplementary European Search Report for counterpart European application EP 10 82 7551 prepared on Jun. 12, 2013.

Abedin, et al., "Vascular Calcification Mechanisms and Clinical Ramifications," *Arterioscler. Thromb. Vasc. Biol.* 24:1161-1170 (Jul. 2004).

Aikawa, et al., "The vulnerable atherosclerotic plaque Pathogenesis and therapeutic approach," *Cardiovasc. Pathol.* 13:125-138 (May-Jun. 2004).

Aikawa, et al., "Arterial and Aortic Valve Calcification Abolished by Elastolytic Cathepsin S Deficiency in Chronic Renal Disease," *Circulation* 119:1785-1794 (Mar. 2009).

Aoyama, et al., "γ-Secretase inhibitor reduces diet-induced atherosclerosis in apolipoprotein E-deficient mice," *Biochem. Biophys. Res. Comm.* 383:216-221 (Apr. 2009).

Artavanis-Tsakonas, et al., "Notch Signaling: Cell Fate Control and Signal Integration in Development," *Science* 284:770-776 (Apr. 30, 1999).

Aster, et al., "Notch Signaling in Leukemia," *Annu. Rev. Pathol. Mech. Dis.* 3:587-613 (2008) (First published online as a Review in Advance on Oct. 17, 2007).

Bianchi, et al., "Physiology and Pathology of Notch Signalling System," *J Cell. Physiol.* 207:300-308 (May 2006).

Brou, et al., "A Novel Proteolytic Cleavage Involved in Notch Signaling: The Role of the Disintegrin-Metalloprotease TACE," *Mol. Cell* 5:207-216 (Feb. 2000).

Chawla, "Control of Macrophage Activation and Function by PPARs," *Circ. Res.* 106:1559-1569 (May 2010).

\* cited by examiner

NOTCH INHIBITION IN THE TREATMENT AND PREVENTION OF A METABOLIC DISEASE OR DISORDER AND CARDIOVASCULAR COMPLICATIONS THEREOF

RELATED APPLICATIONS AND INCORPORATION BY REFERENCE

This application is a continuation-in-part application of international patent application Serial No. PCT/US2010/054798 filed 29 Oct. 2010, which published as PCT Publication No. WO 2011/053822 on 5 May 2011, which claims benefit of U.S. provisional patent application 61/257,026, filed on 1 Nov. 2009.

Reference is made to U.S. Pat. No. 8,133,857 and U.S. patent application Ser. No. 13/358,425.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted in ASCII format via EFS-Web and is hereby incorporated by reference in its entirety. Said ASCII copy, created on May 30, 2012, is named 44766201.txt and is 757 bytes in size.

FIELD OF THE INVENTION

The present invention is directed to methods of treating or preventing both obesity and metabolic syndrome by administering agents that block or modulate the NOTCH signaling pathway. In addition, the invention includes assays for identifying patients at risk of developing these conditions and assays for identifying therapeutic agents based upon their ability to block NOTCH signaling.

BACKGROUND OF THE INVENTION

Obesity, which often associates with other metabolic disorders, has become a global threat to human health. In the United States, over two-thirds of adults are overweight and one-third is obese. The most serious and frequent major complications of obesity are atherosclerosis and "heart attack".

Metabolic syndrome (Sutherland, et al., *Metabolic Syndrome and Related Disorders* 2:82-104 (2004); Esposito, et al., *Nutr. Metab. Cardiovasc. Dis.* 14:228-232 (2004)), relates to obesity and is characterized by a group of metabolic risk factors including: 1) abdominal obesity (excessive fat tissue in and around the abdomen); 2) atherogenic dyslipidemia (high triglycerides; low HDL cholesterol and high LDL cholesterol); 3) elevated blood pressure; 4) insulin resistance or glucose intolerance; 5) a prothrombotic state (e.g., high fibrinogen or plasminogen activator inhibitor-1 in the blood); and 6) a proinflammatory state (e.g., elevated CRP in the blood). Metabolic syndrome has become increasingly common in developed countries and is closely associated with risk of coronary heart disease (Malik, et al., *Circulation* 110: 1245-1250 (2004); Irabarren, et al., *J. Am. Coll. Cardiol.* 48:1800-1807 (2006)). Accumulating evidence suggests that the key features of metabolic syndrome are closely associated with chronic inflammation characterized by macrophage accumulation, increased cytokine production, and activation of a network of inflammatory signaling pathways.

Cardiometabolic syndrome includes obesity-related metabolic disorders and atherosclerosis. Cardiometabolic disorders also promote arterial and valvular calcification which may lead to devastating clinical complications: acute myocardial infarction and aortic stenosis. In addition, diabetes causes chronic kidney disease that also leads to cardiovascular ectopic calcification and acute myocardial infarction. Collectively, several major components of the cardiometabolic syndrome, developed via interrelated mechanisms, enhance each other through local or systemic inflammation.

The NOTCH signaling pathway has been identified as playing an important role in many diverse biological functions, including cellular differentiation and proliferation (see U.S. Pat. No. 6,703,221). Mutations that increase NOTCH signaling have been associated with the development of leukemia and inhibitors of NOTCH are being studied for their potential use in the treatment of neurological diseases and cancer (Artavanis-Tsakonas, et al., *Science.* 284:770-776 (1999); Wang, et al., *Science* 306:269-271 (2004); Stockhausen, et al., *Br. J. Cancer* 92:751-759 (2005); Van Es, et al., *Nature* 435:959-963 (2005)).

The NOTCH pathway is activated by four different transmembrane receptor subtypes (designated as NOTCH-1-NOTCH-4) that rely upon regulated proteolysis. Expression patterns of NOTCH depend on cell type. Following ligand binding, the receptor undergoes sequential cleavage by metalloproteases of the ADAM family (Bru, et al., *Mol. Cell* 5:207-216 (2000); Mumm, et al., *Mol. Cell* 5:197-206 (2000)) and the presenilin-dependent gamma-secretase (Selkoe, et al., *Annu. Rev. Neurosci.* 26:565-97 (2003); De Strooper, et al., *Nature* 398:518-522 (1999)). The final proteolytic cleavage step permits the intracellular domain of the NOTCH receptor to translocate to the cell nucleus where it interacts with transcription factors to induce target gene expression.

In the cell nucleus, the NOTCH intracellular domain undergoes ubiquitilation. Proteolytic processing of the NOTCH precursor protein by furin-protease and its trafficking to the cell membrane also determine turnover and availability of receptors, and, in turn, activation of this signaling pathway. Altered glycosylation of the Notch extracellular domain by Fringe protein family members may also modify efficiency of ligand binding.

As mentioned above, inhibitors of NOTCH, particularly gamma-secretase inhibitors, have received a great deal of attention as possible therapeutic agents for the treatment of neurological diseases (especially Alzheimer's disease) and cancer (especially leukemia). The therapeutic use of these agents in treating or preventing obesity or metabolic syndrome would represent a clear advance in medicine and public health.

Citation or identification of any document in this application is not an admission that such document is available as prior art to the present invention.

SUMMARY OF THE INVENTION

The present invention is directed to methods of treating or preventing obesity or a metabolic disease, disorder or syndrome in a patient by administering a therapeutically effective amount of a compound that inhibits or modulates the NOTCH signaling pathway. Applicants refer to metabolic syndrome with a modified 2005 National Cholesterol Education Program-ATP III definition as 3 or more of the following symptoms: waist circumference ≥40 inches in men, ≥35 inches in women; blood pressure ≥130/85 mmHg; triglycerides ≥150 mg/dL; HDL cholesterol ≤40 mg/dL in men, 50 mg/dL in women; and glucose ≥100 mg/dL. Applicants categorize body mass index (BMI) according to the WHO criteria: BMI≤25 kg/m$^2$=healthy weight, BMI 25-29.9 kg/m$^2$=overweight and BMI≥30 kg/m$^2$=obese.

As used herein, the term "therapeutically effective amount" may refer to a sufficient amount of a NOTCH inhibitor to reduce, when administered at regular intervals over a period of time (e.g., 12-36 months), the body mass index of an obese patient to below 30 kg/m$^2$ (preferably to below 25 kg/m$^2$) or, alternatively, the weight of an obese patient by at least 15% (and preferably 20 or 25%). With respect to metabolic syndrome, the term may refer to a sufficient amount of a NOTCH inhibitor to reduce or eliminate, when administered at regular intervals over a period of time (e.g., 12-36 months), at least one of the symptoms associated with metabolic syndrome mentioned above, and preferably, enough so that the patient does not exhibit any of the symptoms. In the context of prevention, a therapeutically effective amount may be a sufficient dosage when administered at regular intervals to reduce the number of patients becoming obese or developing metabolic syndrome by at least 25% (and preferably at least 50 or 70%) relative to clinically similar patients not receiving the inhibitor. The term "clinically similar" may refer to patients that are not obese and do not have metabolic syndrome or, alternatively, to patients that have similar (e.g., within 15%) NOTCH signaling activity.

The term "NOTCH inhibitor" may refer to an agent capable of blocking NOTCH signaling. Mechanisms of action of such NOTCH inhibitors include, but are not limited to, inhibition of gamma-secretase and subsequent suppression of NOTCH receptor cleavage, inhibition of NOTCH trafficking to the cell membrane, suppression of expression or function of ligands and/or receptors, inhibition of ligand turnover, cleavage, and/or endocytosis, modification of NOTCH glycosylation, alteration of ubiquitilation of NOTCH components including the NOTCH intracellular domain, modification of expression and/or activity of co-factors or effectors (e.g., members of the MAML family, RBP-Jkappa/CBF-1), and alteration of differentiation/population of undifferentiated cells in bone marrow, circulating blood, or peripheral tissues (e.g., fat, arteries, veins, heart, heart valves, brain). Preferred inhibitors may include receptor antagonists that block the binding of NOTCH ligands to receptors, RNA interfering agents for NOTCH components, blocking antibodies against NOTCH components, small molecules and peptides that interfere with expression, function, or activity of any NOTCH components, and gamma-secretase inhibitors. An alternative approach would be a systemic or local delivery of a DNA plasmid encoding a NOTCH component or a dominant negative form of such a component. In addition, the agents to modulate Notch signaling include the ones that can enhance expression or activity of any Notch components that play an inhibitory role in this signaling mechanism. These agents also include any biosimilars that inhibit or modulate expression, function, or activity of any NOTCH components.

In another aspect, levels of expression, function, or activity of NOTCH components in a biological sample such as peripheral blood may be used to determine whether, relative to a control group, a subject that is not obese or that does not have a metabolic disease, metabolic disorder or metabolic syndrome, is at increased risk of developing these conditions in the future. Results indicating that higher levels of NOTCH activity are present in the patient may be an indication of increased risk. The "control group" may be the general population of patients that are not obese or have a metabolic disease, metabolic disorder or metabolic syndrome or the group may be patients that appear normal and that are matched to the patient in ways well known in the art, e.g., by age, gender etc. The test biological sample may be blood, plasma, serum, or urine. The Notch component tested for may be a NOTCH receptor or a NOTCH ligand, particularly a ligand selected from the group consisting of: Delta1 (or Delta-like 1/Dll1), Delta3 (Delta-like 3/Dll3), Delta4 (Delta-like 4/Dll4), Jagged1, and Jagged2. Control samples may be selected using methods well known in the art and might constitute, for example, blood, serum plasma etc. from individuals known to be free of cardiovascular disease or from the population in general. Such assays may also monitor effects of existing or new therapies for the metabolic syndrome and its complications.

Advanced molecular or functional imaging may enable the visualization of biological or pathological processes in vivo. The invention further proposes the use of expression or activity of Notch signaling components as imaging biomarkers to identify patients with subclinical metabolic disorders and associated diseases, to predict future development of the metabolic syndrome and its complications such as atherosclerosis, heart attack, aortic stenosis, and to monitor effects of therapeutic agents or devices against these diseases. Results indicating that higher levels of NOTCH expression or activity may be present in the patient are an indication of increased risk.

The invention also encompasses methods for assaying a test compound to determine whether it has potential use in the treatment or prevention of obesity or metabolic syndrome based upon its effect on any features or measures of the NOTCH signaling pathway, inhibition suggesting potential therapeutic value. For example, test compounds may be incubated with gamma-secretase to determine whether proteolytic cleavage is prevented. Alternatively, receptor-binding assays may be performed using test compounds in the presence of known ligands for NOTCH, e.g., Delta1 (Delta-like 1/Dll1), Delta4 (Delta-like 4/Dll4), Jagged 1 or Jagged 2 (see, e.g., Ikeuchi, et al., *J. Biol. Chem.* 278:7751-7754 (2003)) to determine the extent to which receptor binding is blocked. RBP-Jkappa/CBF-1 activity or expression of known direct target genes of NOTCH, including but not limited to the Hes and Hey family members, may also be used to examine the effects of a test compound. Compounds identified using these assays may undergo further evaluation in animal models to test their safety and potential clinical value.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1:
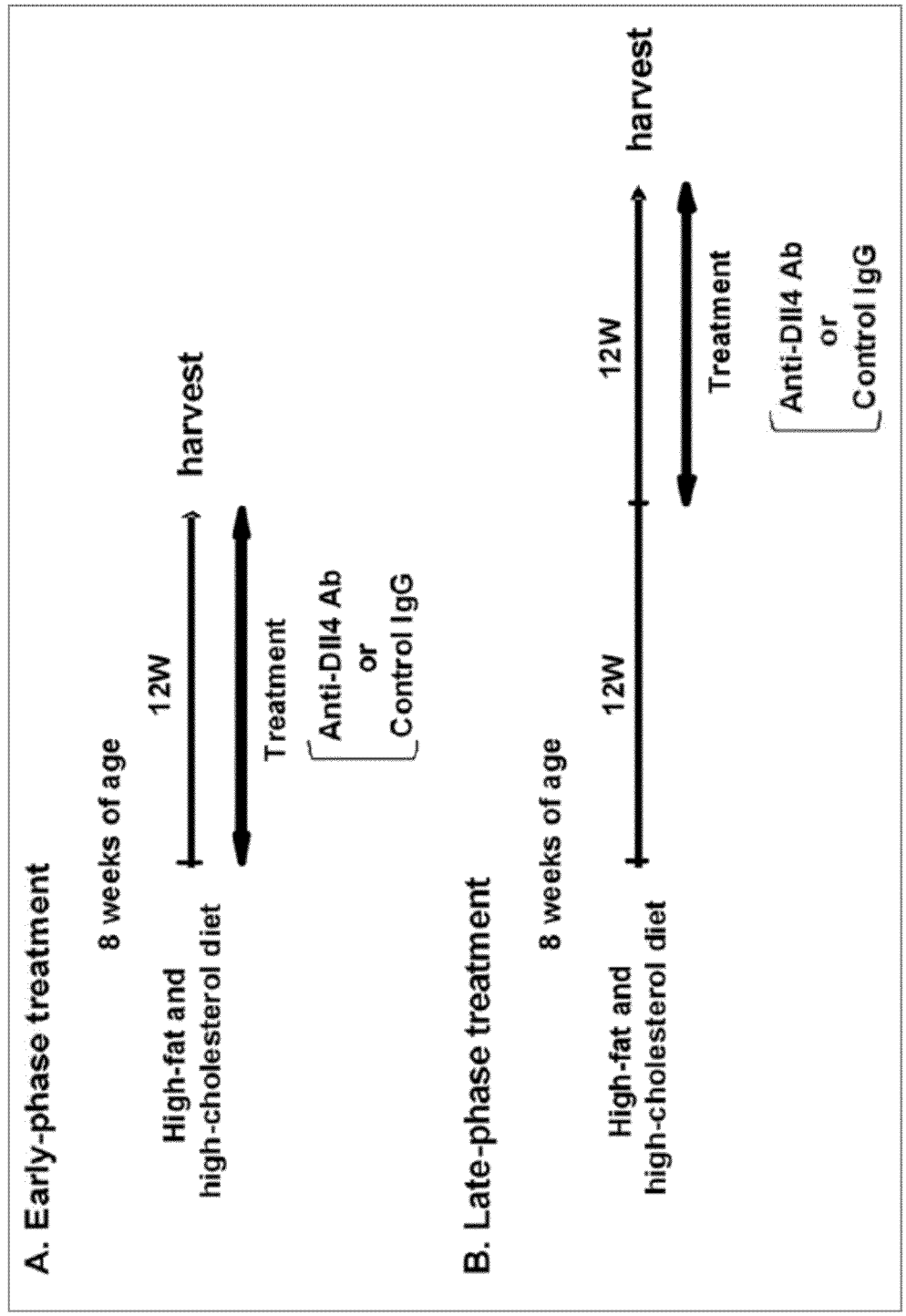
FIGS. 1A-1B depict two groups in which Ldlr$^{-/-}$ mice were randomly assigned and fed a high-cholesterol/high-fat diet. The mice were injected with 250 μg of hamster anti-mouse Dll4 antibody (Dll4 Ab) or isotype control IgG (IgG) (BioXcell) intraperitoneally twice a week from 8 weeks of age or 20 weeks of age, for 12 weeks.

The present invention is based, in part, on the concept that inhibition or modulation of NOTCH signaling can be used in the treatment of obesity, related metabolic disorders and ensuing cardiovascular complications. Therapeutic targets related to Notch signaling include ligands such as Delta-like 1 (Dll1), Dll3, Dll4, Jagged 1 and Jagged 2), receptors (Notch1, Notch2, Notch3, and Notch4), and all other co-factors, including but not limited to Mastermind-like 1, 2, and 3 (MAML1-3) and RBP-Jkappa. The methods include, but are not limited to, systemic or local administration of blocking antibodies, peptides, and RNA therapeutics, e.g., small-interfering RNA oligonucleotides (siRNA oligos), antisense oligonucleotides and biosimilars.

The present invention is directed to therapeutic methods in which an inhibitor of NOTCH signaling is administered to a patient to treat or prevent the development of either obesity or metabolic syndrome. Any of the NOTCH inhibitors, including gamma-secretase inhibitors, which have been described in the art may be used for this purpose. References describing such inhibitors and the way in which they can be made, purified, and used include: U.S. Pat. No. 5,703,129; U.S. Pat. No. 6,448,229; U.S. Pat. No. 6,683,091; U.S. Pat. No. 6,756,511; U.S. Pat. No. 6,890,956; U.S. Pat. No. 6,984,626; U.S. Pat. No. 6,995,155; WO 01/70677; WO 02/081435; WO 03/018543; WO 00/50391; WO 03/0422646; WO 03/041735; U.S. published application 2005-0227973; 2006-0030694; 2006-0004004; 2006-0009467; 2005-0261276; 2005-0143369; and 2005-0075320, all of which are hereby incorporated by reference.

The compounds described above will typically be administered to patients in a pharmaceutical composition comprising the compound along with a pharmaceutically acceptable carrier. The carrier may be any solvent, diluent, liquid or solid vehicle that is pharmaceutically acceptable and typically used in formulating drugs. Guidance concerning the making of pharmaceutical formulations can be obtained from standard works in the art (see, e.g., Remington's Pharmaceutical Sciences, 16$^{th}$ edition, E. W. Martin, Easton, Pa. (1980)). In addition, pharmaceutical compositions may contain any of the excipients that are commonly used in the art. Examples of carriers or excipients that may be present include, but are not limited to, sugars (e.g., lactose, glucose and sucrose); starches, such as corn starch or potato starch; cellulose and its derivatives (e.g., sodium carboxymethyl cellulose, ethyl cellulose, or cellulose acetate); malt; gelatin; talc; cocoa butter; oils (e.g., peanut oil, cottonseed oil, safflower oil, sesame oil, olive oil, corn oil, or soybean oil); glycols; buffering agents; saline; Ringer's solution; alcohols; lubricants; coloring agents; dispersing agents; coating agents; flavoring agents; preservatives; or antioxidants.

The invention is compatible with the delivery of compounds by any route known in the art, including peroral, internal, rectal, nasal, lingual, transdermal, intravenous, intra-arterial, intramuscular, intraperitoneal, intracutaneous and subcutaneous routes. The delivery methods also include drug eluting stents. The most preferred route is oral, especially using dosage forms such as tablets, capsules or solutions. In cases where a compound is susceptible to degradation in the stomach of a patient, it may be enterically coated or it may be administered parenterally.

It will be understood that pharmaceutical compositions may contain any pharmaceutically acceptable form of an inhibitory compound, i.e., any form which maintains therapeutic activity and which does not cause unacceptable adverse effects when administered. For example, a compound may be in the form of a pharmaceutically acceptable salt, ester or pro-drug.

Liquid dosage forms for oral administration include, but are not limited to, pharmaceutically acceptable emulsions, microemulsions, solutions, suspensions, syrups and elixirs. In addition to the active compounds, liquid dosage form may contain inert diluents commonly used in the art, such as, for example, water, or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, dimethyl formamide, oils, glycerol, alcohols, polyethylene glycols, and fatty acid esters.

Injectable preparations may be in the form of sterile, injectable aqueous or oleaginous suspensions, diluents or solvents that may be used may include 1,3-butanediol, water, Ringer's solution and isotonic saline solutions. In addition, oils or fatty acids may be present.

As mentioned previously, the most preferred dosage forms will be those for oral administration, particularly solid dosage forms such as capsules, tablets, pills, powders or granules. In these dosage forms, the active compound will typically be mixed with at least one inert, pharmaceutically acceptable excipient or carrier such as sodium citrate, or dicalcium phosphate and/or: fillers or extenders such as starches, lactose, sucrose, glucose, mannitol and silicic acid; binders such as, for example, carboxymethyl cellulose, alginates, gelatin, polyvinylpyrrolidinone, and acacia, humectants such as glycerol; disintegrating agents such as calcium carbonate, silicates or sodium carbonate; solution retarding agents such as paraffin; absorption accelerators such as quaternary ammonium compound; wetting agents such as cetyl alcohol or glycerol monostearate; absorbents such as kaolin; and lubricants, such as talc, magnesium stearate; sodium lauryl sulphate, etc. In addition, dosage forms may include buffering and flavoring agents.

Pharmaceutical compositions will be administered to patients in one or more unit dosage forms. A "unit dosage form" refers to a single drug administration entity, e.g., a single tablet, capsule or injection vial. The amount of inhibitory compound present should be at least the amount required to reduce the symptoms associated with obesity or metabolic syndrome when one or more unit dosage forms are administered to a patient. On a biological level, sufficient inhibitor should be present to substantially reduce NOTCH signaling pathway activity. For example, a sufficient amount of a gamma-secretase inhibitor may be included in unit dosage forms to reduce gamma-secretase activity by 20%, 40%, 60% or more. The exact dosages given and amount of inhibitor in unit dosage forms may be determined for individual compounds using methods that are well known in the art of pharmacology and may be further adjusted by physicians on a case-by-case basis based upon clinical considerations.

Subjects, particularly individuals that are obese or have metabolic syndrome, or who are at high risk of becoming obese or developing metabolic syndrome, may be treated by administering one or more of the inhibitory compounds described above. As previously mentioned, the exact dosage will depend upon the particular compound being given and will be determined using procedures well known in the art, balancing toxicity and therapeutic efficacy. Compounds may also be given to test animals to study their effect on the obesity or metabolic syndrome. In these cases, dosages are limited only by toxicity. It should also be recognized that inhibitory compounds may be administered as the sole active agents in a dosage form, or they may be combined with other drugs to improve overall effectiveness.

Assays designed to identify compounds of potential use in the treatment or prevention of obesity and metabolic syndrome may involve any method known in the art for identifying compounds that inhibit the NOTCH signaling pathway. The most common assays will be either enzymatic assays for inhibitors of gamma-secretase or assays to identify agents that interfere with receptor binding. In the former case, many different assays have been described in the art which may be utilized for examining the effect of a test compound on gamma-secretase activity. These include assays using radiolabeled substrates followed by HPLC or TLC analysis (see, e.g., Evin, et al., *J. Pept. Sci.* 1(2):132-139 (1995)); FACS assays (Sernee, et al., *Eur. J. Biochem.* 270:495-506 (2003)); and other in vitro or in vivo assays (Pinnix, et al., *J. Biol. Chem.* 276:481-487 (2001); Xu, et al., *Neurobiol. Aging* 23(6):1023-1030 (2002); and Holke, et al., *FEBS J.* 272:5544 (2005)). All of these references are hereby incorporated by reference in their entirety. Commercially available assays such as the QTL Lightspeed assay (QTL Biosystems, Santa Fe, N. Mex.) may also be used.

Receptor binding assays that may be adapted to identify compounds that interfere with the binding of NOTCH ligands have been described in the art and may be used in conjunction with the present invention (see, e.g., Shimizu, et al., *J. Biol. Chem.* 274(46):32961-32969 (1999); Shimizu, et al., *Biochem. Biophys. Res. Commun.* 276(1):385-389 (2000), both of which are hereby incorporated by reference in their entirety). In general, receptor binding assays are performed using a source of NOTCH receptor together with one of the ligands that are known to bind to the receptor and with the compound being tested for binding activity. As a source of receptor, mammalian cells that have been transformed to recombinantly express NOTCH-1-NOTCH-4 may be used. The assay itself may be performed either with intact cells or with membranes prepared from the cells (see, e.g., Wang, et al., *Proc. Natl. Acad. Sci. USA* 90:10230-10234 (1993)). The membranes or cells are incubated with one of the ligands for the NOTCH receptor (e.g., Delta1 (Delta-like 1/Dll1), Delta4 (Delta-like 4/Dll4), Jagged 1 or Jagged 2) and with a preparation of the compound being tested. After binding is complete, the receptor is separated from the solution containing ligand and test compound, e.g., by filtration, and the amount of binding that has occurred is determined. Preferably, the ligand used is detectably labeled with a radioisotope such as $^{125}$I, however, fluorescent chemiluminescent or enzymatic labels can also be used.

Nonspecific binding may be determined by carrying out the binding reaction in the presence of a large excess of unlabeled ligand. For example, labeled ligand may be incubated with receptor and test compound in the presence of a thousand-fold excess of unlabeled ligand. Nonspecific binding should typically be subtracted from total binding, i.e., binding in the absence of unlabeled ligand, to arrive at the specific binding for each sample tested. Other steps, such as washing, stifling, shaking, filtering and the like may be included in the assays as necessary. Typically, wash steps are included after the separation of membrane-bound ligand from ligand remaining in solution and prior to quantitation of the amount of ligand bound, e.g., by counting radioactive isotope. The specific binding obtained in the presence of test compound is compared with that obtained in the presence of labeled ligand alone to determine the extent to which the test compound has displaced receptor binding.

In performing binding assays, care must be taken to avoid artifacts which may make it appear that a test compound is interacting with the NOTCH receptor when, in fact, binding is being inhibited by some other mechanism. For example, the compound being tested should be in a buffer which does itself substantially inhibit the bind of ligand to the NOTCH receptor and should, preferably, be tested at several different concentrations. In addition, it is desirable that compounds identified as displacing the binding of ligand to receptor be reexamined in a concentration range sufficient to perform a Scatchard analysis of the results. This type of analysis is well known in the art and can be used for determining the affinity of a test compound for receptor (see, e.g., Ausubel, et al., *Curr. Protocols in Mol. Biol.*, 11.2.1-11.219 (1993); *Laboratory Techniques in Biochemistry and Molecular Biology*, Work, et al., NY (1978)). Computer programs may be used to help in the analysis of results (see, e.g., Munson, *Meth. Enzymol.* 92:543-577 (1983)).

The effects/actions of compounds can also be determined by other indicators of activated states of NOTCH signaling including, but not limited to, receptor cleavage and/or nuclear translocation, ligand cleavage and/or endocytosis, NOTCH trafficking to cell membrane, expression of ligands and/or receptors, ligand turnover, cleavage, and/or endocytosis, NOTCH glycosylation, ubiquitilation of NOTCH components including NOTCH intracellular domain, and expression and/or activity of co-factors or effectors (e.g., members of the MAML family, RBP-Jkappa/CBF-1), differentiated state or population of undifferentiated cells in bone marrow, circulating blood, spleen, or other tissues, and expression levels of known direct target genes of NOTCH signaling including but not limited to the Hes and Hey family members.

Inhibition or modulation of Notch signaling components can prevent, retard, or improve various metabolic diseases or disorders (e.g., obesity, metabolic syndrome, insulin resistance, diabetes, (including type 2 diabetes), and dyslipidemia) and their clinical complications such as acute myocardial infarction ("heart attack") and aortic stenosis and other cardiovascular complications such as but not limited to atherosclerosis; chronic kidney disease (particularly in view of diabetes impact on kidney vasculature); arterial calcification; valvular calcification, including but not limited to aortic or mitral calcification; valvular stenosis, including but not limited to, aortic or mitral valve stenosis; acute myocardial infarction; restenosis after coronary intervention; accelerated tissue damage or delayed healing after coronary intervention, including but not limited to: valve implantation (including bioprosthetic valve implantation); stent implantation; implantation of engineered tissues, allograft, homograft (including but not limited to, Ross procedure), bioprosthesis tissues, Dacron grafts or any synthetic or bioprosthetic conduit; heart transplantation; arterial or vein graft implantation (including but not limited to, saphenous vein bypass grafts and hemodialysis AV shunts); stroke; and heart failure; failure of vein grafts for coronary bypass surgery; diabetic nephropathy; vasculitis; retinopathy; erectile dysfunction; and non-cardiovascular complications such as, but not limited to, pancreatitis; nonalcoholic fatty liver disease; neuroinflammation; cognitive impairment; cancer.

Notch signaling components as therapeutic targets include, but are not limited to: ligands (e.g., Dll4); receptors (e.g., Notch3); co-factors (e.g., RBP-Jκ, MAML1); gamma-secretase complex; ADAM-family members; and prototypical direct targets Hes and Hey family genes. These Notch signaling components and related molecules can also serve as circulating or imaging biomarkers for diagnosis, monitoring, or risk prediction of cardiometabolic disorders. In addition, inhibition or modulation of Notch signaling leads to suppression of various dysmetabolic events, including but not limited to, expression of gene products (e.g., IL-1β, iNOS), activation of signaling mechanisms (e.g., NF-κB, Akt, MAPK), cell functions/phenotypes (e.g., fat and vascular inflammation, fat hypertrophy, foam cell formation).

Cardiovascular therapeutic targets for Notch inhibition or modulation also include, but are not limited to, the following clinical problems: metabolic disorders that accelerate tissue damage or delayed healing after coronary intervention (e.g., stent implantation); heart transplantation; allograft, homograft (e.g., Ross procedure) or bioprosthesis valve implantation; arterial, vein (e.g., saphenous vein bypass grafts, hemodialysis AV shunts) or Dacron grafts; and any synthetic, bioprosthetic, or tissue engineered conduits; metabolic disorders that delay healing of injured tissues such as cardiac muscles following acute myocardial infarction and ischemic brain after stroke; metabolic disorders that accelerate development of heart failure; and metabolic disorders that impair healing of injured tissues after any surgical procedures. Other complications of metabolic disorders that may be treated include diabetic nephropathy, chronic kidney disease, vasculitis, and retinopathy.

It is also known that metabolic syndrome positively associates with risk of cancer. Thus, the detection of patients at risk of developing metabolic syndrome also serves to identify individuals at increased risk of developing cancer, and treatments for metabolic syndrome may serve to reduce this risk.

Therapeutic targets include these metabolic disorders and all the associated pathologic states, dysfunctions, and complications in multiple organs (e.g., liver, pancreas, arteries, veins, heart, heart valves, kidney, lung, skin, eye). Therapeutic targets also include the brain and nervous system (e.g., neuroinflammation or cognitive impairment). In addition, Notch inhibition or modulation targets failure of tissue-engineered organs implanted in the dysmetabolic recipients and may be used during in vitro processes to develop tissue-engineered conduits before implantation (e.g., tissue-engineered scaffolds loaded with Notch inhibitors or modulators). These engineered tissues include, but are not limited to, arteries, veins, heart valves, liver, bone, and ear. In addition, Notch inhibition or modulation targets erectile dysfunction associated with metabolic disorders, particularly insulin resistance and type 2 diabetes.

Measurements of Notch components in biological samples including, but not limited to, peripheral blood or urine may indicate the severity of metabolic disorders and/or predict cardiovascular risk. These methods are also used to identify subclinical features of metabolic disorders and thus predict future development of cardiometabolic syndrome. Furthermore, measurements of Notch components may be used to monitor the effects of existing or new therapies. Metabolic disorders that may be detected include, but are not limited to, obesity, dyslipidemia (particularly high triglycerides and low high-density LDL or HDL), insulin resistance, type 2 diabetes mellitus, arterial and valvular calcification, chronic kidney disease, pancreatitis, and nonalcoholic fatty liver disease. Cardiovascular complications that may be identified, predicted, or monitored in this manner include but are not limited to: restenosis after coronary intervention; aortic valve calcification and stenosis; mitral valve annulus calcification; failure of vein grafts for coronary bypass surgery, and vasculitis. The same procedure may also be used to determine the extent to which metabolic organs (e.g., adipose tissue, liver) and other related organs (e.g., arteries, veins, cardiac valves, kidney) have an inflammatory nature which is likely to progress and cause more serious problems.

Methods of measuring levels of Notch components or related molecules in clinical or preclinical biological samples include but are not limited to ELISA. For example, ELISA for Dll4 detects increased levels of a soluble/shedded form of this ligand in the plasma of patients with cardiometabolic syndrome or animal models of cardiometabolic disorders.

Notch signaling components can serve as targets for clinical or preclinical molecular imaging. As noted previously, molecular imaging is a powerful tool for finding pathological tissues or organs such as inflamed arteries or calcifying valves before devastating clinical complications occur (e.g., heart attacks, aortic stenosis). Identifying such subclinical lesions using molecular imaging predicts future events and permits clinicians to monitor the effects of new drugs or medical devices. Methods for detecting the expression or activity of Notch signaling components include, but are not limited to, optical or near infrared fluorescence imaging, MRI, nuclear imaging (e.g., PET or SPECT), ultrasound, and CT.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Delta-Like 4 Participates in the Pathogenesis of Atherosclerosis and Obesity: A Potential Common Mechanism for Cardiometabolic Disorders The present example examines whether the Notch ligand Delta-like 4 (Dll4) contributes to the pathogenesis of cardiometabolic disorders.

A. Methods

Mice and Anti-Dll4 Ab Treatment

Eight-week-old male Ldlr$^{-/-}$ mice were purchased from The Jackson Laboratory. Ldlr$^{-/-}$ mice were fed a high-fat, high-cholesterol diet (D12108, Research Diets; 40% fat, 1.25% cholesterol) from 8 weeks of age through the completion of the study. All mice were housed on a 12-hour light/dark cycle, with food and water ad libitum. Animal care and experimentation was approved by the Harvard Medical School Institutional Animal Care and Use Committee. Ldlr$^{-/-}$ mice were assigned randomly to two groups and were injected with 250 μg of hamster anti-mouse Dll4 antibody (Dll4 Ab) or isotype control IgG (IgG) (BioXcell) intraperitoneally twice a week from 8 weeks of age or 20 weeks of age, for 12 weeks (FIG. 1). Mice were weighed twice a week. For bolus injection experiment, Applicants injected 250 μg of Dll4 Ab or IgG to fat-fed 10-week-old Ldlr$^{-/-}$ mice, and harvested them at 6 hours after injection.

Histology and Immunohistochemical Analysis

At the time of the harvest, after blood collection, Applicants perfused 0.9% sodium chloride solution at a constant pressure via the left ventricle and then removed tissues immediately. Thoracic aorta, aortic root, liver, and thymus were embedded in OCT compound (TissueTek). Epididymal fat pads and small intestines were embedded in paraffin after fixation with formalin or 4% paraformaldehyde, respectively. Tissues were sectioned serially (6 μm intervals) and stained with hematoxylin and eosin (H&E) for general morphology. Some sections were incubated with anti-Mac3 antibody, anti-MCP-1 antibody (both from BD Biosciences), and anti-Dll4 antibody (Rock Land) followed by the avidin-biotin complex technique, and stained with ACE. Picrosirius red staining was performed as described previously and viewed under polarized microscope. Alkaline phosphatase (ALP) activity was detected according to the manufacturer's instructions (alkaline phosphatase substrate kit, Vector Laboratories). Calcium deposition in plaques was detected by von Kossa staining, using a commercially available kit (Polysciences, Inc.). To analyze adipocyte size, Applicants measured the two-dimensional size of 100 adipocytes in five fields and got the value by average of each field. Applicants also performed PAS staining with sections from the small intestine, using a commercially available staining kit (Sigma-Aldrich). Images were captured and processed with OPTIPHOT (Nikon) with a digital camera (DXM1200F, Nikon). Morphometric analysis was performed using image analysis software (Image-Pro Plus 6.0, Media cybernetics).

Ex Vivo Fluorescence Reflectance Imaging of the Aorta and Aortic Valve

Ldlr$^{-/-}$ mice that received late-phase treatment were used for fluorescence reflectance imaging. Two imaging agents were administered to each mouse 24 hours before the harvest—cross-linked iron oxide (CLIO) 750 fluorescent nanoparticle (Jaffer, et al. *Mol. Imaging* 5:85-92 (2006)) for detection of macrophage accumulation and OsteoSense680 (VisEn) for detection of osteogenic activity. After perfusion with 0.9% sodium chloride solution at a constant pressure via the left ventricle, Applicants removed the heart and aorta. Signals from macrophages and osteogenic activity were detected on aortae using the Kodak Imaging Station 4000MM Pro (Kodak). Laser scanning fluorescence microscopy (FLUOVIEW1000, Olympus) was used on the opened aortic root to detect signals for osteogenic activity. The target-to-background ratio was calculated as described previously (Aikawa, et al., *Circulation* 119:1785-1794 (2009)).

Analysis of Metabolic Parameters

Serum insulin (Alpco), total cholesterol, and triglyceride levels (Wako) were measured with commercially available kits after four-hour fasting. Serum MCP-1 levels (Signosis) were measured with samples obtained at the harvest. Glucose and insulin tolerance tests were performed after 16 and 4 hours fasting, respectively. Glucose and insulin solutions were injected into the peritoneal cavity at doses of 1.0 mg/kg and 0.5 unit/kg, respectively. Blood was collected via tail vein at different time points, and glucose levels were measured with a glucometer.

Metabolic Studies

The details of indirect experiments were described previously (Maeda, et al. *Cell Metab.* 1:107-119 (2005)). Mouse physical activity was monitored with OPTO-M3 Activity Application Device (Columbus Instruments). Each animal's movements (other than scratching, grooming, digging, etc.) were determined using infrared beams in x, y, and z axes and recorded for 48 consecutive hours. Animals were placed in an indirect open circuit calorimeter (Oxymax System, Columbus Instruments). Oxygen and carbon dioxide concentrations by volume were monitored at the inlet and outlet parts of a partially sealed chamber, through which a known flow of ambient air is being forcibly ventilated. The concentration difference measured between the parts was used to compute oxygen consumption ($VO_2$) and carbon dioxide production ($VCO_2$). The consumption and production information were presented in units of ml/kg/min and normalized to 0° C. and 760 mmHg. Food intake was investigated with the Oxymax Feed Scale Device (Columbus Instruments) and manual measurements.

Blood Pressure Measurement

Blood pressure of each mouse was measured with a non-invasive blood pressure system (CODA, Kent Scientific Corporation) in conscious animals. In each animal, the mean value of three measurements was used for comparison.

Fractionation of Adipose Tissue

Previous papers describe fractionation of adipose tissue (Hosooka, et al. *Nat. Med.* 14:188-193 (2008)). Applicants minced epididymal fat pads in PBS containing 2% BSA, and then incubated it on a shaking platform for 60 min at 37° C. with the same medium containing collagenase (1250 U/ml). Applicants then passed the mixture through a nylon filter (pore size, 250 mm) to remove undigested material and centrifuged the filtrate for 5 min at 200 g at 4° C. Applicants recovered floating cells and the pellet as the mature adipocyte fraction and the stromal vascular fraction (SVF), respectively.

Flow Cytometry Analysis

To investigate effects of Dll4 blockade on tissue monocytes/macrophages and circulating leukocytes, Applicants performed flow cytometry analysis (Swirski, et al., *Science* 325:612-616 (2009)). Samples were collected from Ldlr$^{-/-}$ mice treated with Dll4 Ab or IgG for 12 weeks (n=3, per group). Anti-Ly-6C-FITC, anti-B220-PE, anti-CD49b-PE, anti-CD90-PE, anti-TER119-PE, anti-Ly-6G-PE, anti-NK1.1-PE, biotinylated-anti-MHC class II, anti-F4/80-PE-Cy7, anti-CD11b-APC-Cy7, and anti-CD11c-Alexa700 (BD Biosciences) were used for flow cytometric analyses. Strep- PerCP (BD Biosciences) was used to label biotinylated Ab. Monocytes were identified as $CD11b^{high}$ (CD90/B220/CD49b/NK1.1/TER119/Ly-6G)$^{low}$ (F4/80/I-Ab/CD11c)$^{low}$ Ly-6C$^{high/low}$.

Neutrophils were identified as $CD11b^{high}$ (CD90/B220/CD49b/NK1.1/Ly-6G)$^{high}$ (F4/80/I-Ab/CD11c)$^{low}$ Ly-6C$^{int}$. Data were acquired on an LSRII (BD Biosciences) and analyzed with FlowJo v.8.5.2 (Tree Star, Inc.).

Isolation of Macrophages from Adipose Tissue

From SVF obtained from adipose tissue, Applicants isolated F4/80-positive macrophages using magnetic sorting (EasySep system, StemCell Technologies). SVF was obtained from Ldlr$^{-/-}$ mice treated with Dll4 Ab or IgG for 12 weeks. Applicants used a PE-conjugated anti-F4/80 antibody as a primary Ab (Biolegend).

Isolation of Residual Peritoneal Macrophages

At the time of harvest, Applicants collected residual peritoneal macrophages by washing the peritoneal cavity with PBS. Cells were seeded on plastic dishes and harvested after 16-hour incubation in RPMI-1640 medium containing 5% FBS.

Cell Culture

3T3-L1 preadipocytes (American Type Culture Collection) were maintained in Dulbecco's modified Eagle's medium (DMEM) (Gibco) containing 10% FBS. Differentiation of 3T3-L1 preadipocytes to mature adipocytes was performed as previously described and used as differentiated 3T3-L1 adipocytes at day 10 after the induction of differentiation. Differentiation was initiated two days after cells were confluent by adding fresh medium containing 0.5 mM isobutylmethylxanthine, 1 µM dexamethasone, and 10 µg/ml insulin. After two days, the methylisobutylxanthine and dexamethasone were removed and insulin was maintained for two additional days. On day 4 and thereafter, DMEM containing only 10% FBS was replaced every two days.

Differentiated 3T3-L1 adipocytes were starved for 16 hours and then used for in vitro experiments. For blockade Dll4-mediated Notch signaling, Applicants treated 3T3-L1 adipocytes with Dll4 Ab or IgG (10 µg/ml) and γ-secretase inhibitor (DAPT, 10 µM) or DMSO for 24 hours. To activate Dll4-mediated Notch signaling, Applicants seeded 3T3-L1 adipocytes to plates coated with recombinant mouse Dll4 (rDll4) (1 µg/ml), and then harvested cells after 48-hour incubation (Williams, et al., *Blood* 107:931-939 (2006)). Applicants also used SN50 (25 µg/ml) NF-κB inhibitor to determine the interaction between Notch signaling and the NF-κB pathway.

RAW264.7 cells (American Type Culture Collection) were also maintained in DMEM containing 10% FBS. For blockade of Dll4-mediated Notch signaling, Applicants pre-treated RAW264.7 cells with Dll4 Ab or IgG for 2 hours and then stimulated these cells with 1 ng/ml LPS for 24 hours. LPS stimulation activates the Notch signaling in RAW264.7 cells.

Transient Transfection and Luciferase Assay

Applicants transfected siRNA against mouse Dll4 (Dharmacon), plasmid encoding mouse Dll4 (GeneCopoeia), RBP-Jκ reporter (SABiosciences), and Notch3 intracellular domains (N3ICD) to 3T3-L1 adipocytes by electroporation (Nucleofector system; Amaxa) according to the manufacturer's instructions. The Dll4-expressing plasmid was also transfected to RAW264.7 cells. N3ICD was a generous gift from Dr. Shigeru Chiba (Department of Clinical and Experimental Hematology, Graduate School of Comprehensive Human Sciences, University of Tsukuba). Applicants transfected 2 µg of siRNA or plasmid to cells and harvested them 48 hours or 24 hours after transfection, respectively. Applicants used 5 µl of RBP-Jκ reporter solution for each transfection. After incubation for 24 hours, cells were seeded to rDll4-coated plates and used for the luciferase assay after 48-hour incubation. Luciferase activity was determined using a Dual-Luciferase Reporter Assay System (Promega). Applicants transfected 5 µg of N3ICD to cells and harvested them 24 hours after transfection.

Immunocytochemistry

Differentiated 3T3-L1 adipocytes incubated in rDll4-coated plates were fixed in 4% paraformaldehyde and permeabilized with 0.1% NP40. After blocking with 1% goat serum, cells were incubated with a rabbit anti-p65 antibody (Santa Cruz Biotechnology), followed by an Alexa Fluor 594-conjugated donkey anti-rabbit Ig antibody (Molecular Probes). Nuclei were counterstained with Hoechst 33342 (Sigma). Cells were observed under an ECLIPSE TE2000-U (Nikon) equipped with a mercury illumination system and SPOT RT Camera (Diagnostic Instruments, Inc.).

Real-Time Quantitative RT-PCR

Applicants synthesized cDNA from total RNA extracted from tissues and cells. Real-time quantitative RT-PCR was done with a MyiQ single-color real-time PCR detection system (BioRad) and PerfeCTa SYBR Green SuperMix for iQ (Quanta Biosciences). Data are expressed in arbitrary units that were normalized by β-actin.

Immunoblotting

Lysates prepared from tissues and cells in lysis buffer containing protease inhibitor cocktail (Sigma) and phosphatase inhibitor cocktail (Roche) were separated with SDS-PAGE gels. Applicants used the following antibodies: NF-κB p65 (Santa Cruz Biotechnology), phospho-NF-κB p65 (Rock Land), IK-Bα (Cell Signaling), and β-actin (Sigma).

Statistics

Data are expressed as mean±SEM for continuous variables. Comparison between two groups was performed by unpaired Student's t-test. Comparisons of multiple groups were made by one-way ANOVA, followed by the Student-Newman-Keuls multiple comparison test. A P value<0.05 was considered statistically significant.

B. Results

Increasing incidence of obesity, a major component of the metabolic disease cluster, closely associates with atherosclerosis and represents the cardiometabolic syndrome. Accumulating evidence links chronic inflammation, particularly accumulation of activated macrophages, and cardiometabolic disorders (Hotamisligil, *Nature* 444:860-867 (2006)). Notch signaling, one of the fundamental signaling mechanisms, regulates cell fate decisions (Artavanis-Tsakonas, et al., *Science* 284:770-776 (1999)), and also contributes to physiological homeostasis and pathological processes in adults (Aster, at al., *Annu. Rev. Pathol.* 3:587-613 (2008); Radtke, et al., *Immunity* 32:14-27 (2010)). Notch receptors (Notch1-4) undergo proteolytic cleavage when bound by Delta-like (Dll1, Dll3, Dll4) or Serrate (Jagged1, Jagged 2) ligands expressed on adjacent cells, allowing nuclear translocation of the Notch intracellular domain. Notch pathway components are expressed in a cell-type-specific fashion and have diverse context-dependent functions. Applicants recently showed that macrophages in human atheromata express Dll4, previously known to be specific to endothelial cells, and demonstrated that Dll4-triggered Notch signaling promotes inflammatory responses in macrophages in vitro (Fung, et al., *Circulation* 115:2948-2956 (2007)).

The present study tested the hypothesis in vivo that the pro-inflammatory properties of Dll4 may contribute to the pathogenesis of cardiometabolic disorders, using antibody blockade. Generation, characterization, and effects of Applicants' Dll4 Ab (HMD4-2) are described in recent papers. The use of neutralizing anti-mouse Dll4 Ab enabled to circumvent the embryonic lethality reported in Dll4-deficient mouse studies (Gale, et al. *Proc. Natl Acad. Sci. USA* 101:15949-15954 (2004)). Applicants also performed mechanistic experiments in vivo and in vitro to address the mechanisms for the effects of Dll4 blockade on cardiometabolic disorders.

Figure 2:
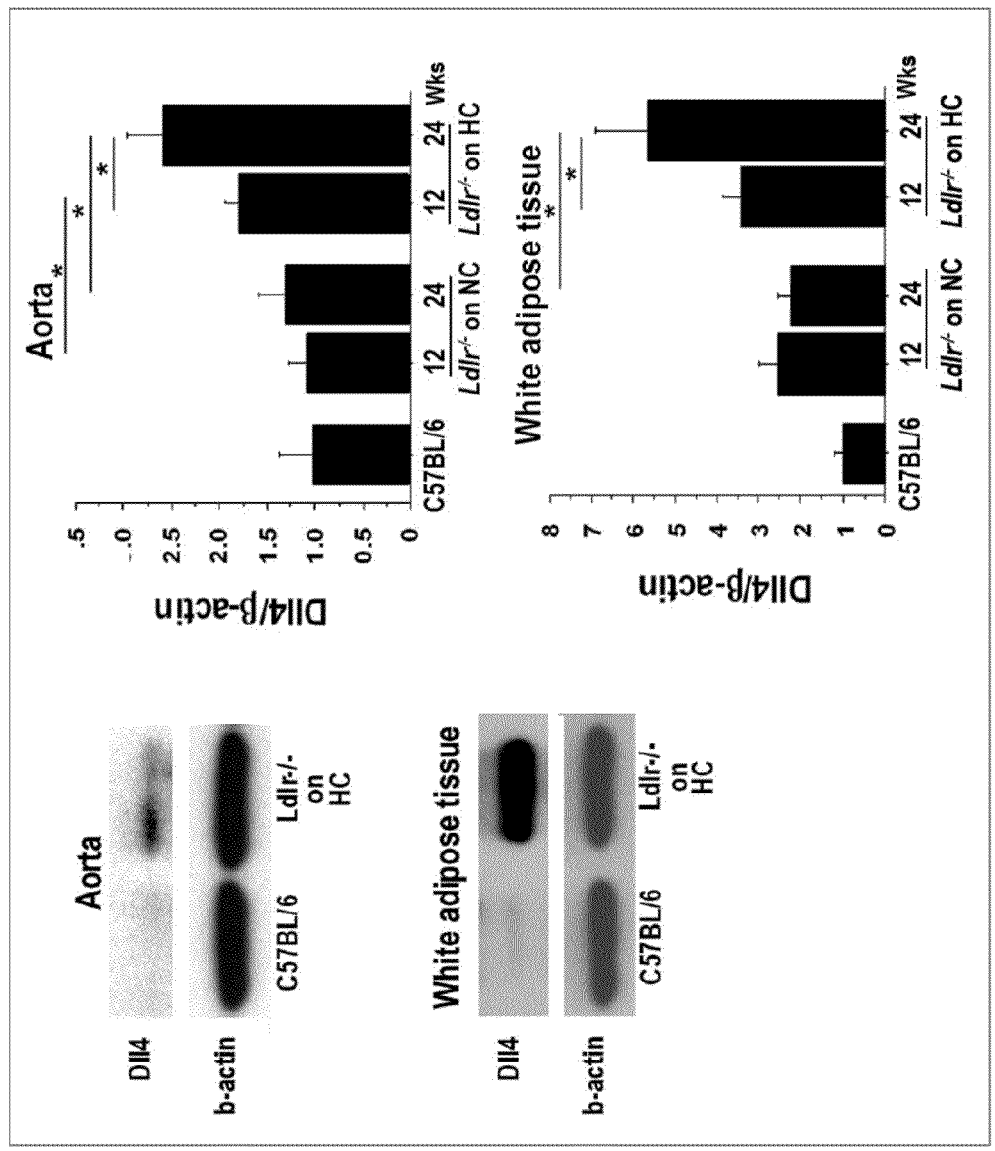
FIG. 2 depicts high-cholesterol/high-fat feeding promoting expression of Dll4 mRNA and protein in adipose tissue and aorta in a time-dependent manner, compared with normal-chow feeding.
Figure 3:
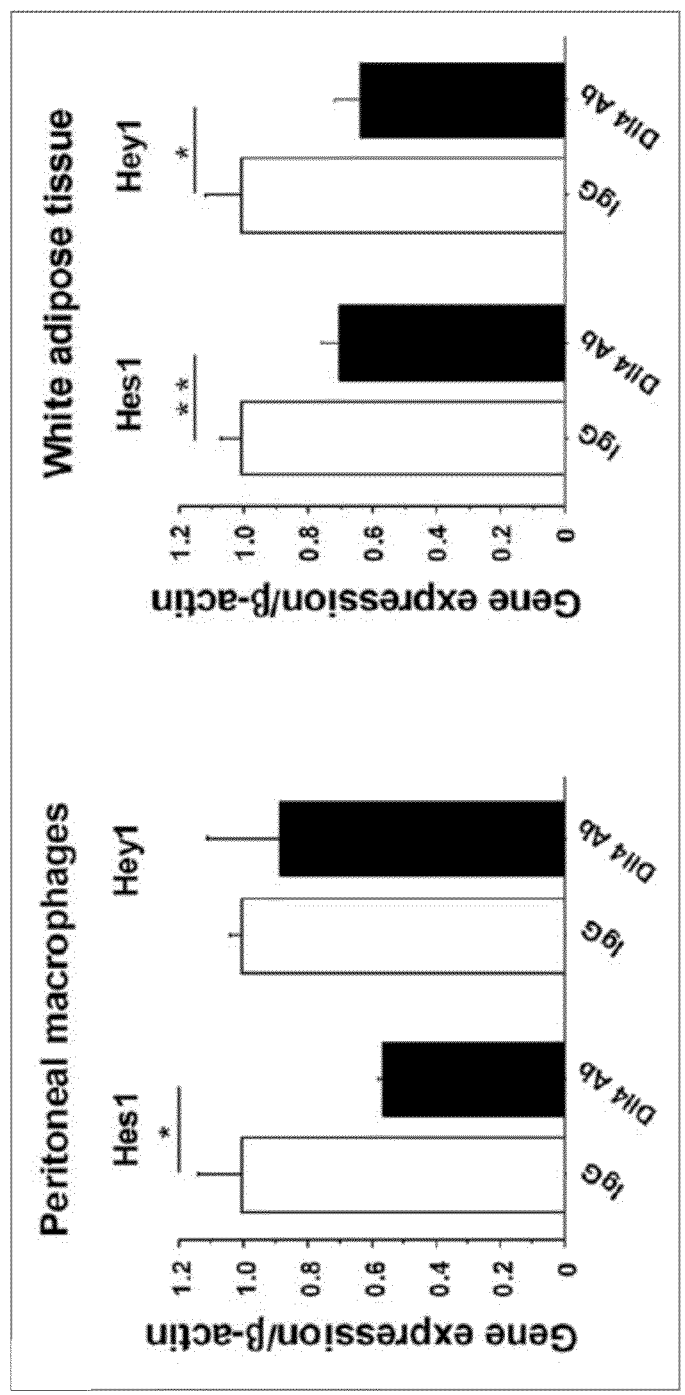
FIG. 3 depicts an effect of bolus injection of Dll4 Ab (250 μg) to Ldlr$^{-/-}$ mice on Notch target genes Hes1 and Hey1 in peritoneal macrophages and adipose tissue.

Applicants first examined Dll4 expression in the histological sections of epididymal adipose tissue and atherosclerotic vascular lesions. Human white adipose tissues expressed Dll4, as did atheromata as Applicants previously described (Fung, et al., *Circulation* 115:2948-2956 (2007)). Epididymal adipose tissue and atherosclerotic lesions of 32-week-old $Ldlr^{-/-}$ mice fed a high-fat diet (40% fat and 1.25% cholesterol) also expressed Dll4. High-fat feeding promoted expression of Dll4 mRNA and protein in adipose tissue and aorta, compared with normal-chow feeding (FIG. 2), suggesting that pro-inflammatory environment promotes Dll4 expression as Applicants reported previously (Fung, et al., *Circulation* 115:2948-2956 (2007)). Bolus injection of Dll4 Ab (250 µg) to $Ldlr^{-/-}$ mice revealed significant reduction of the prototypical Notch target genes Hes1 and Hey1 in fat and peritoneal macrophages (FIG. 3). These results suggest that Dll4 Ab suppresses Notch signaling in target organs and cells important in metabolic disease.

To investigate the effects of Dll4 Ab on the initiation and progression of cardiometabolic disorders, Applicants administered Dll4 Ab or isotype control IgG (250 µg, i.p., twice a week) for 12 weeks to fat-fed $Ldlr^{-/-}$ mice from 8 weeks of age (early phase treatment to prevent the disease initiation) or 20 weeks of age (late phase for regression), respectively (FIG. 1).

Figure 4A:
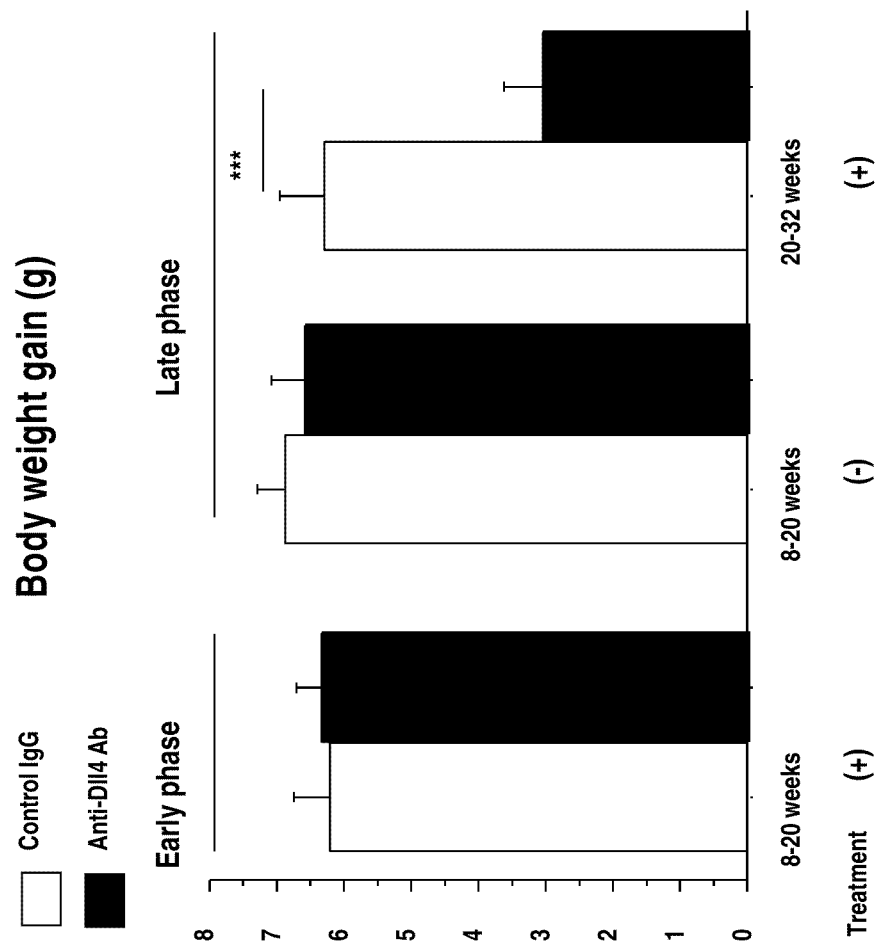
FIGS. 4A-C depicts Dll4 Ab treatment retarded body weight gain as compared with IgG in late-phase treatment. Dll4 Ab treatment significantly reduced both fat weight and mass (DEXA scan), and adipocyte size. Early-phase administration showed no significant difference in body weight. Dll4 expression in 3T3-L1 adipocytes increased during differentiation in vitro, which may explain no effects with early-phase administration.
Figure 4B:
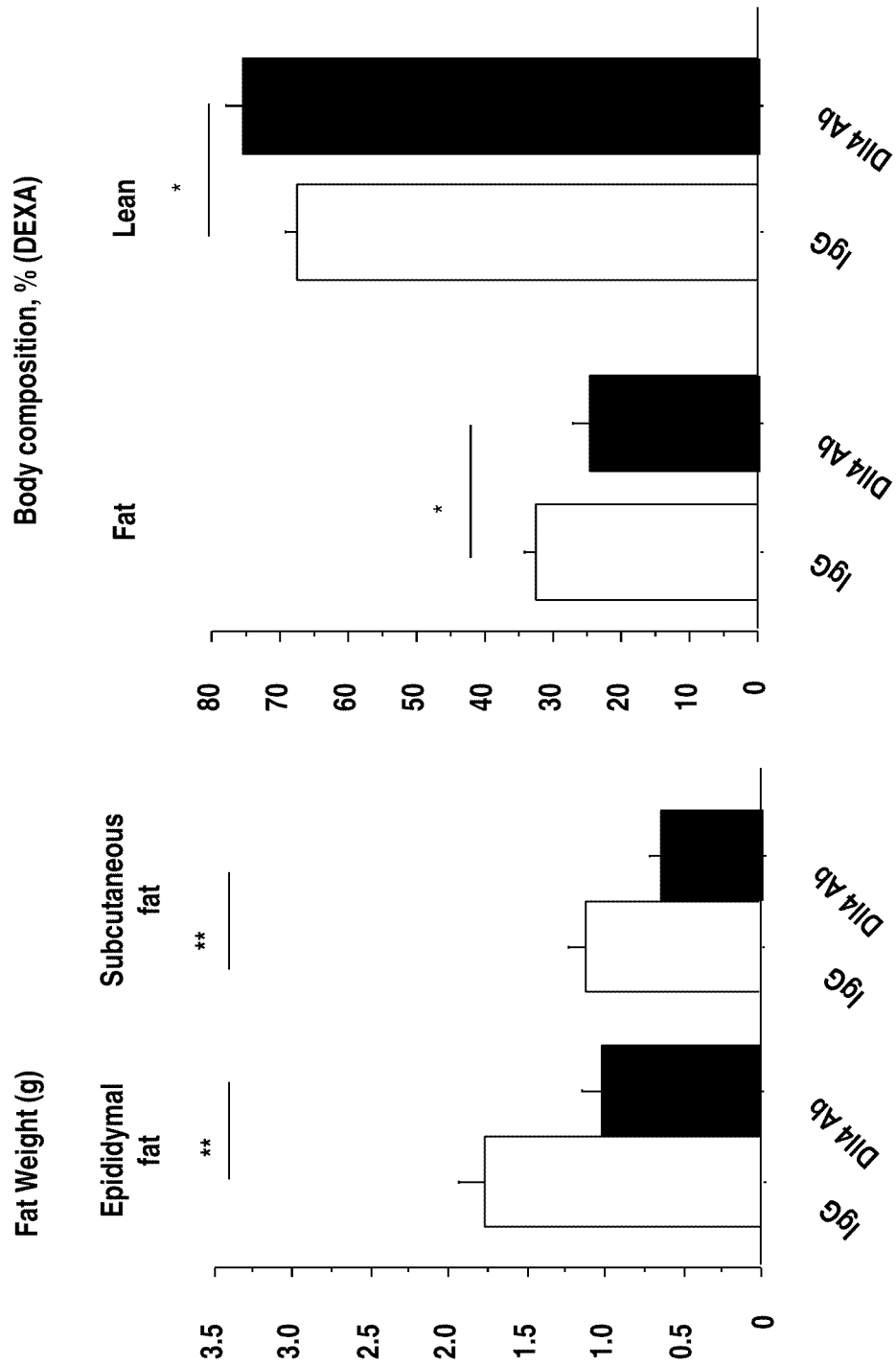
Figure 4C:
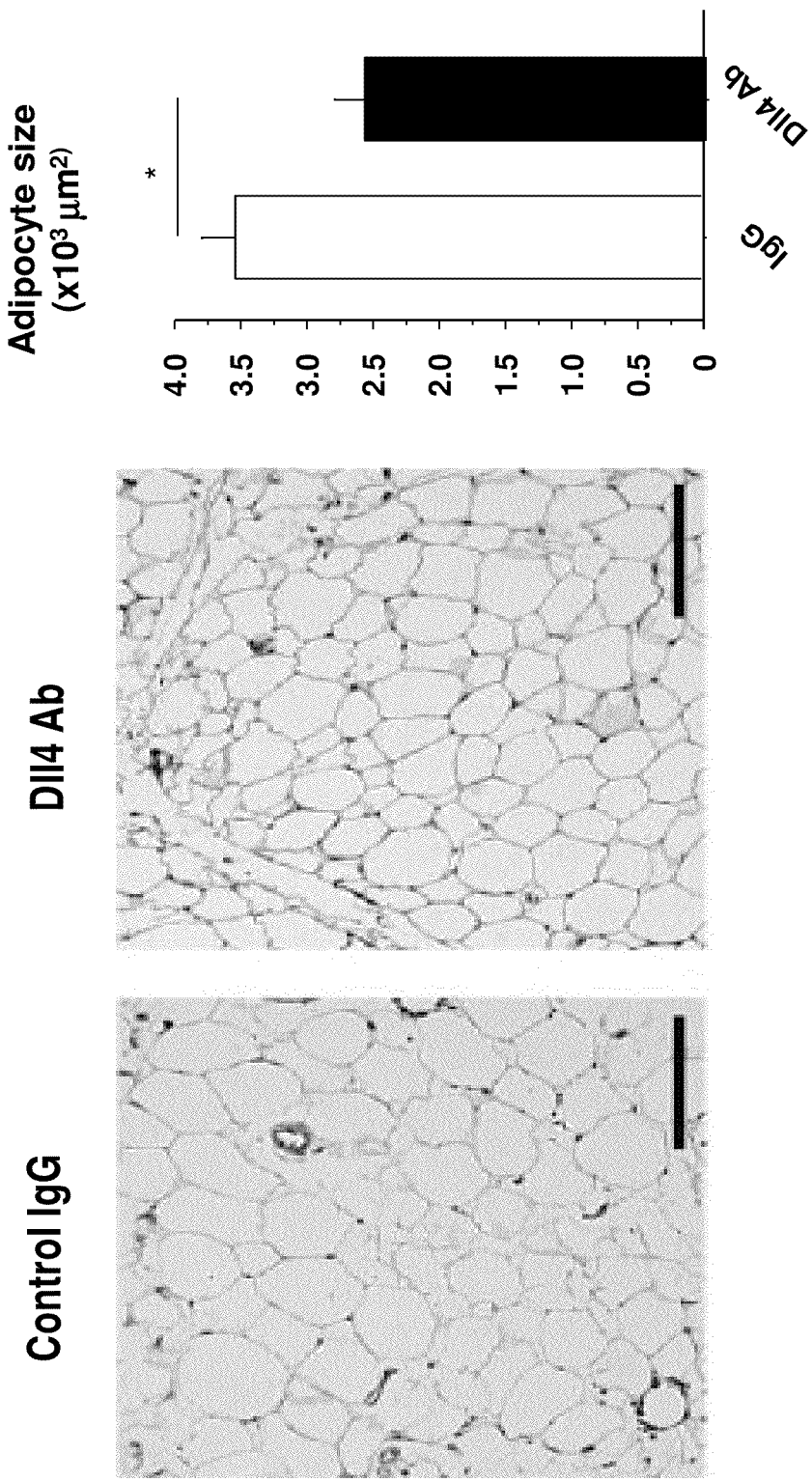

Dll4 Ab retarded body weight gain compared with IgG in late-phase treatment, although food intake was similar (FIG. 4A). Dll4 Ab treatment significantly reduced both fat weight and mass (FIG. 4B), and adipocyte size (FIG. 4C). Early-phase administration showed no significant difference in body weight. Dll4 expression in 3T3-L1 adipocytes increased during differentiation in vitro, which may explain no effects with early-phase administration.

Figure 5:
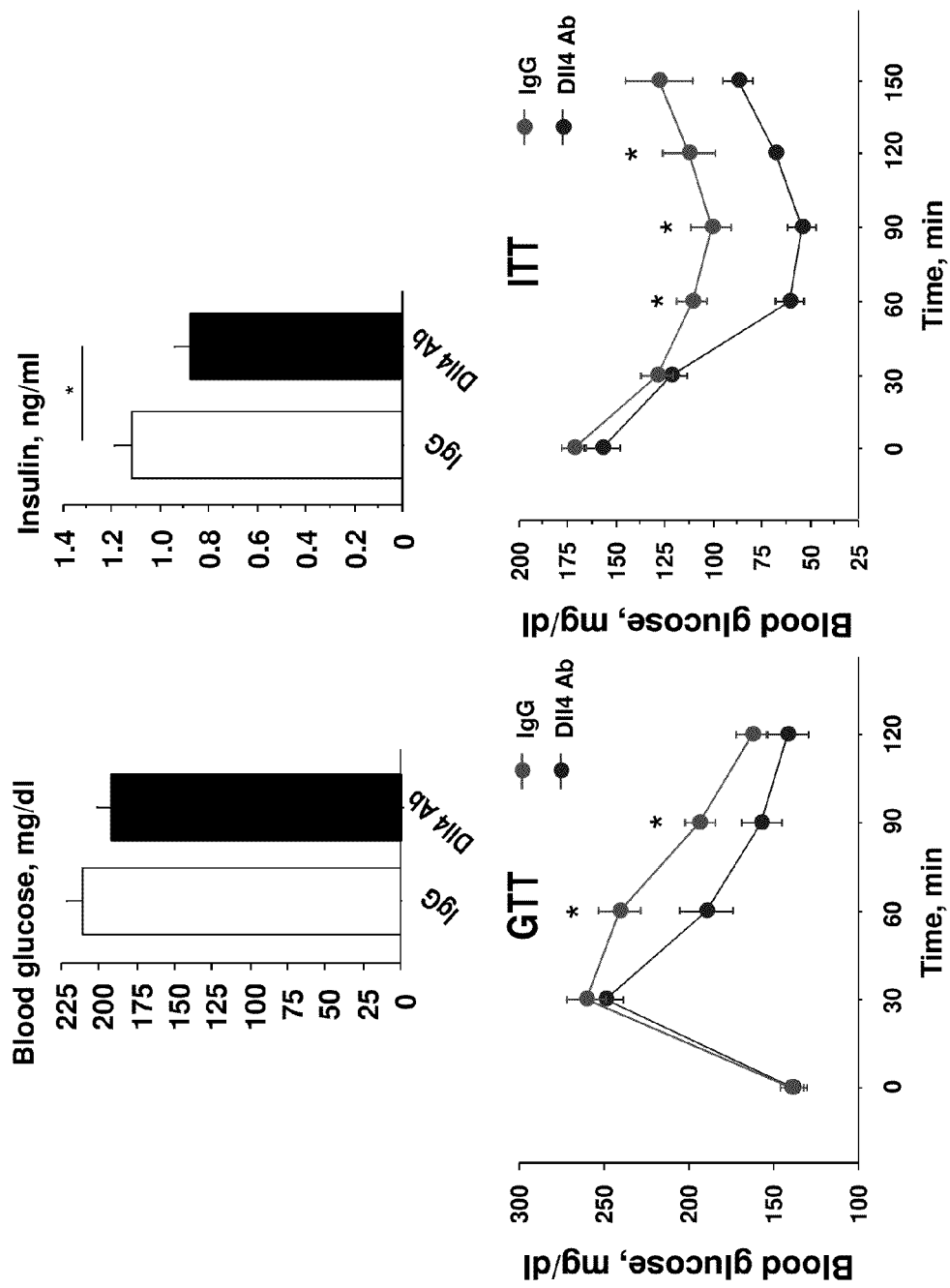
FIG. 5 depicts the effects of Dll4 blockade on glucose homeostasis. After treatment, while blood glucose levels after 4-hour fasting were similar in both groups, serum insulin levels were lower in Ab-treated mice. Glucose and insulin tolerance tests (GTT and ITT) revealed that Dll4 blockade sensitized fat-fed Ldlr$^{-/-}$ mice to insulin.
Figure 6:
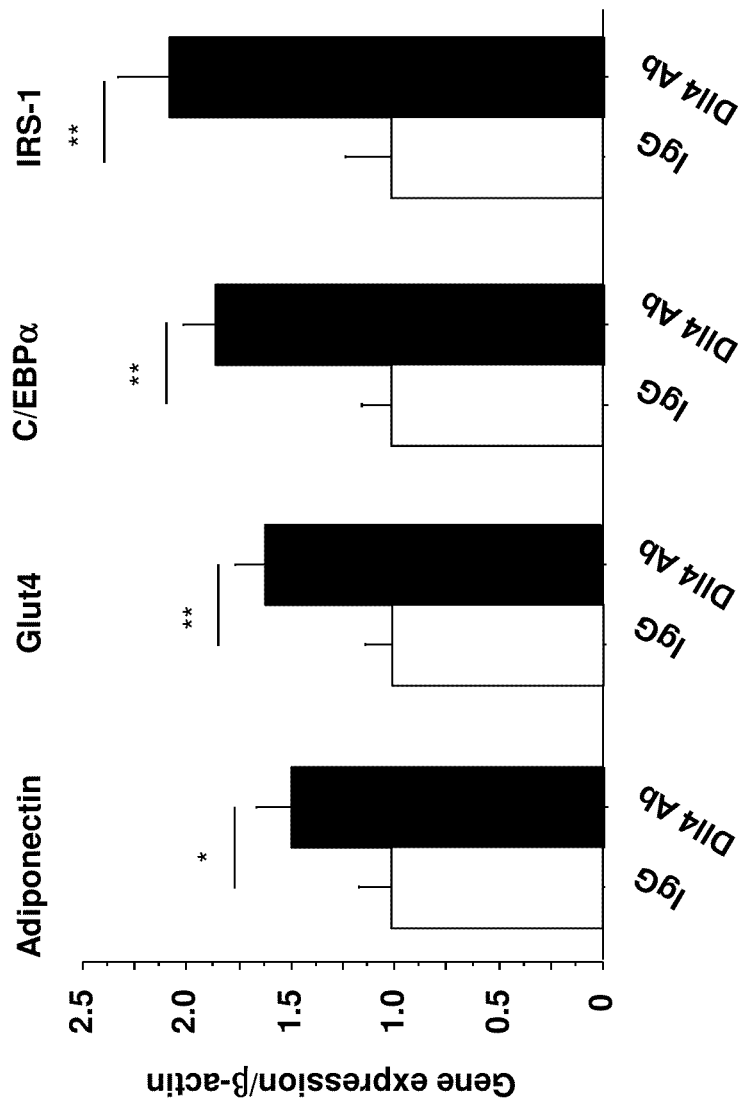
FIG. 6 depicts the increased expression of adiponectin, GLUT4, C/EBPα and IRS-1, relative to insulin sensitivity, in adipose tissue of Ab-treated mice.

Reduction of fat mass prompted us to examine the effects of Dll4 blockade on glucose homeostasis. After treatment, while blood glucose levels after 4-hour fasting were similar in both groups, serum insulin levels were lower in Ab-treated mice (FIG. 5). Glucose and insulin tolerance tests revealed that Dll4 blockade sensitized fat-fed $Ldlr^{-/-}$ mice to insulin (FIG. 5). The expression of adiponectin, GLUT4, C/EBPα and IRS-1 related to insulin sensitivity also increased in adipose tissue of Ab-treated mice (FIG. 6). Applicants did not observe significant differences between groups in serum lipid levels and blood pressure. Determining whether differences in energy expenditure in Dll4 Ab-treated mice could account for the differences in adiposity employed indirect calorimetry and physical activity experiments after 12 weeks of treatment. The rates of carbon dioxide production, oxygen consumption, and physical activity in Ab-treated mice tended to be higher than those in control mice, albeit with no statistically significant differences at this experimental point. Both groups of mice had similar respiratory quotient. Dll4 Ab administration did not affect physical activity as examined by infrared beams, and treated animals did not show any obvious signs of distress.

Figure 7A:
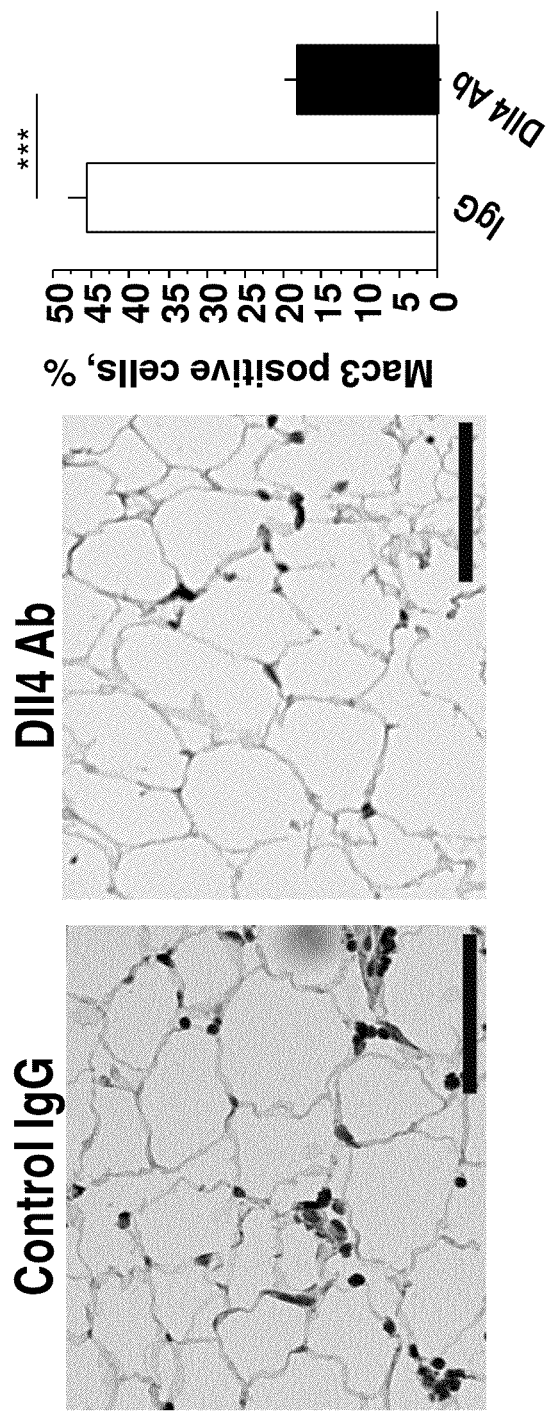
FIGS. 7A-B depict immunostaining and quantitative RT-PCR for macrophage markers in adipose tissue, indicating that Dll4 Ab treatment reduced macrophage accumulation.
Figure 7B:
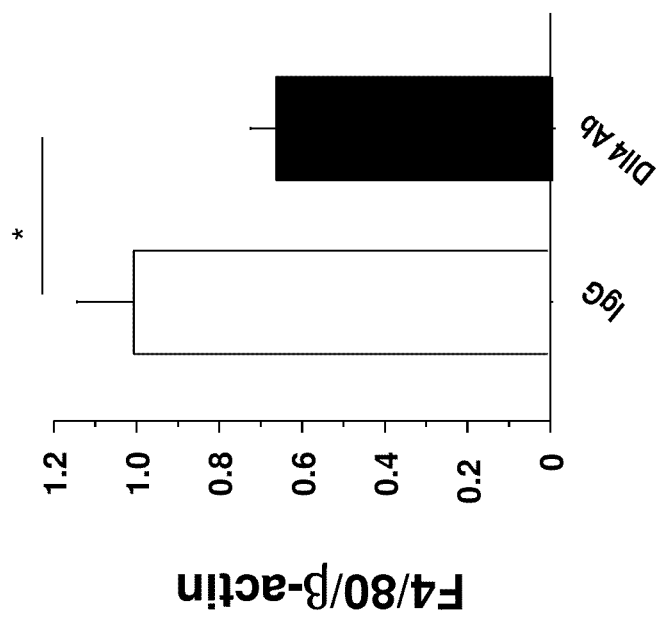
Figure 8:
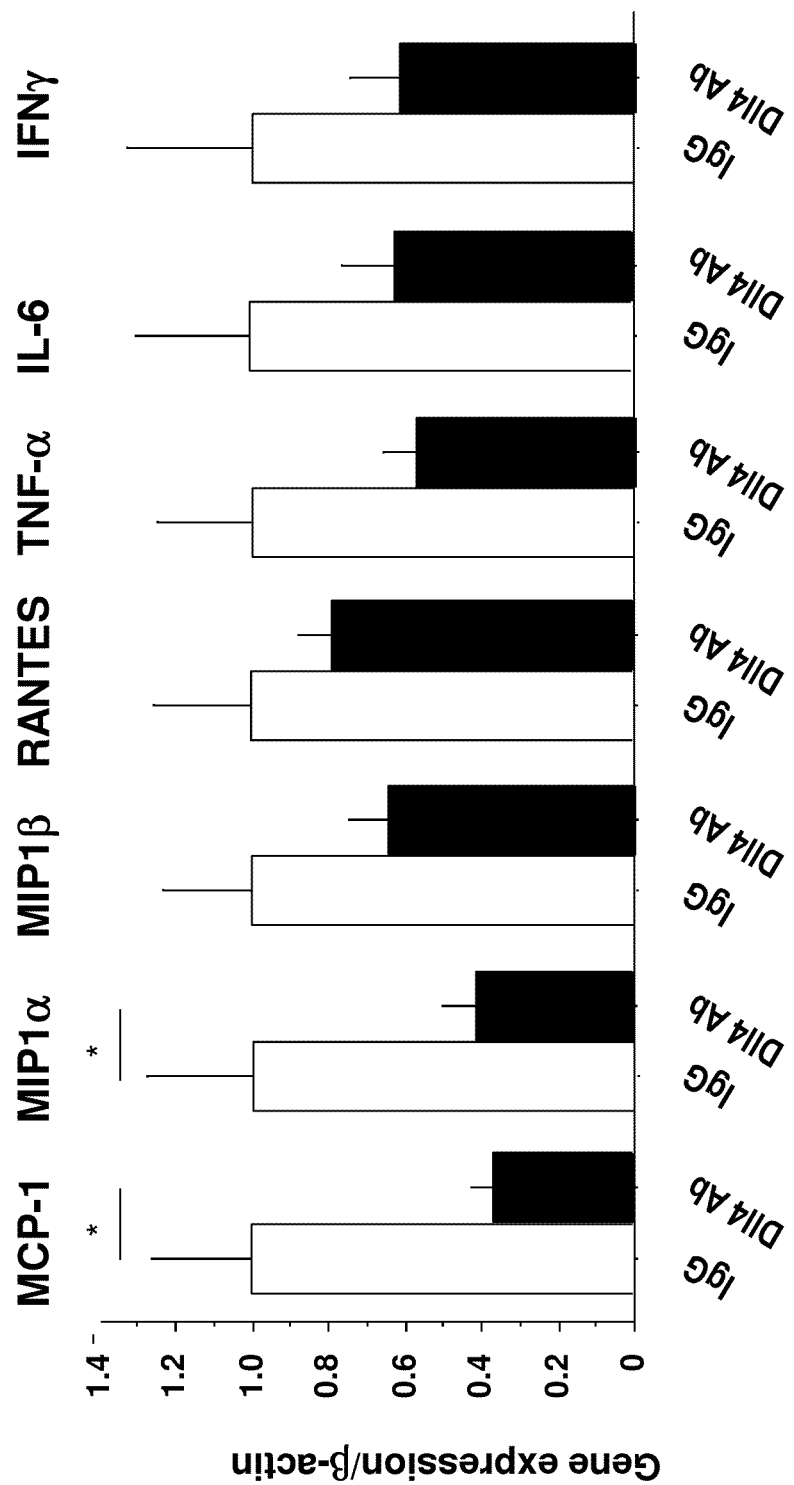
FIG. 8 depicts reduction of proinflammatory molecules, including monocyte chemoattractants MCP-1 and MIP-1α, in adipose tissue in Ab-treated animals.

Visceral obesity and insulin resistance associate closely with increased accumulation of macrophages in adipose tissue (Hotamisligil, *Nature* 444:860-867 (2006)). Therefore, Applicants hypothesized that Dll4 blockade may reduce macrophage content and/or activity in adipose tissue. Immunostaining and quantitative RT-PCR for macrophage markers showed that Dll4 Ab administration decreased macrophages in adipose tissue (FIGS. 7A-B). Adipose tissue in Ab-treated animals also showed decreased expression of proinflammatory molecules, including monocyte chemoattractants MCP-1 and MIP-1α (FIG. 8).

Figure 9A:
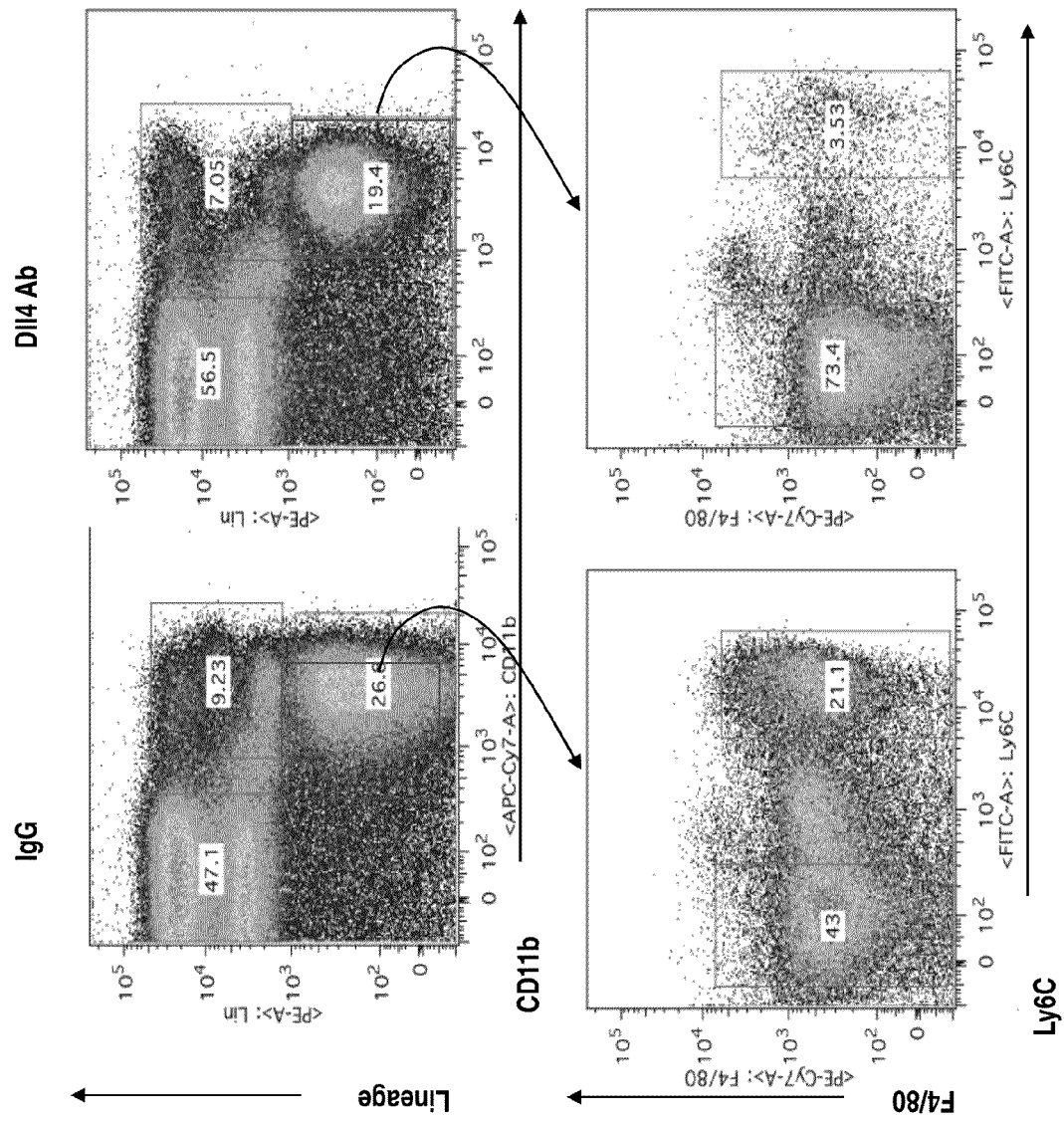
FIGS. 9A-9B depict the effects of Dll4 blockade on inflammatory properties of macrophages as examined by flow cytometry using stromal vascular fraction (SVF) obtained from epididymal fat. A proinflammatory subpopulation of monocytes/macrophages (Ly6C high) was decreased in the fat of Dll4 Ab-treated animals whereas no changes were observed in circulating monocytes and bone marrow cells.
Figure 9B:
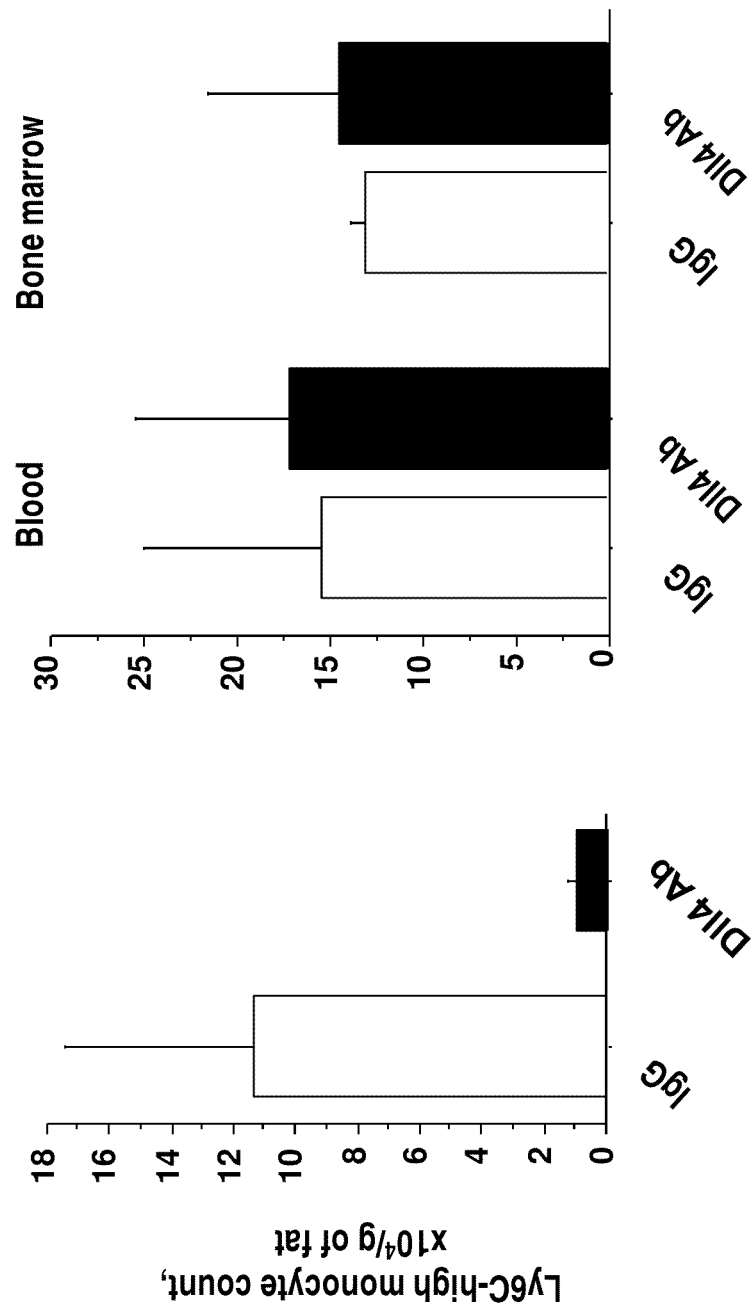
Figure 10:
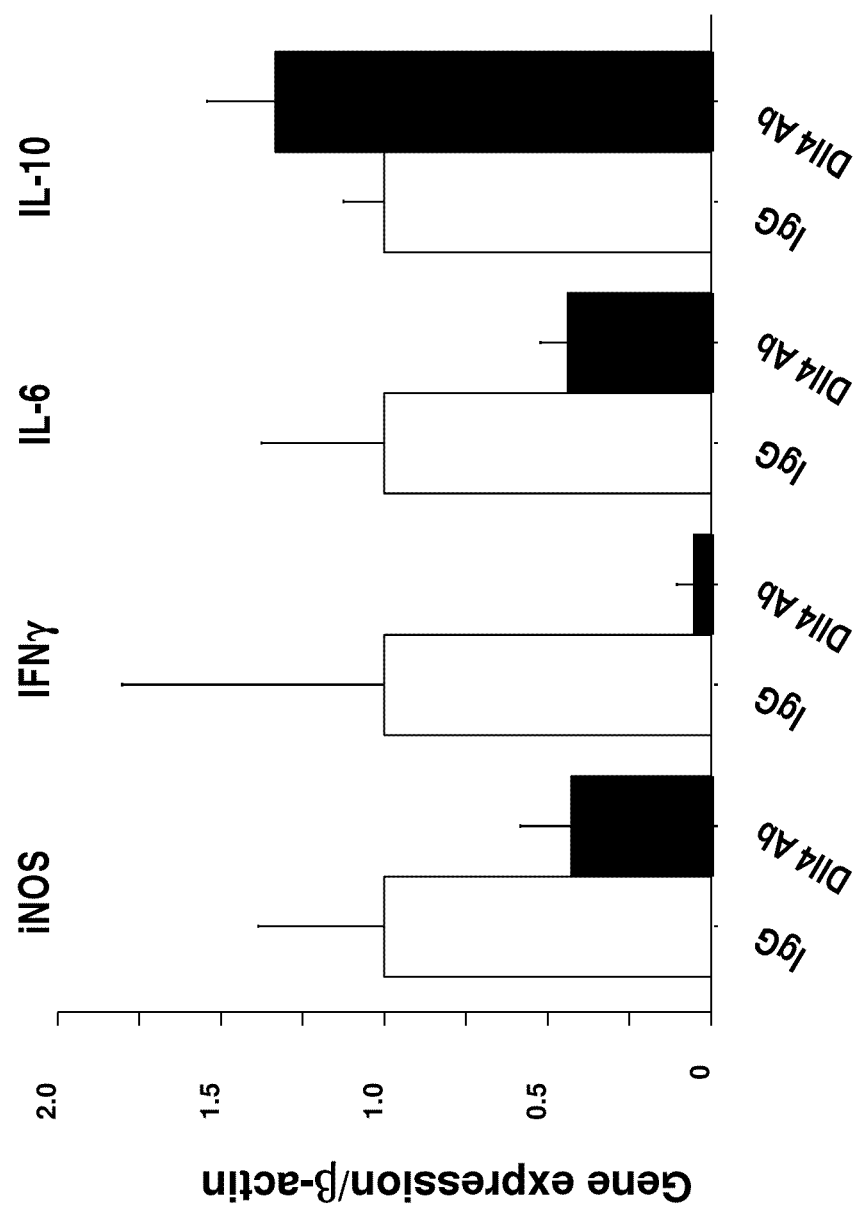
FIG. 10 depicts the tendency for F4/80-positive macrophages collected from SVF of Ab-treated animals to express lower levels of pro-inflammatory M1 molecules (e.g. iNOS, IFN-γ, and IL-6) and slightly higher levels of anti-inflammatory IL-10.
Figure 11A:
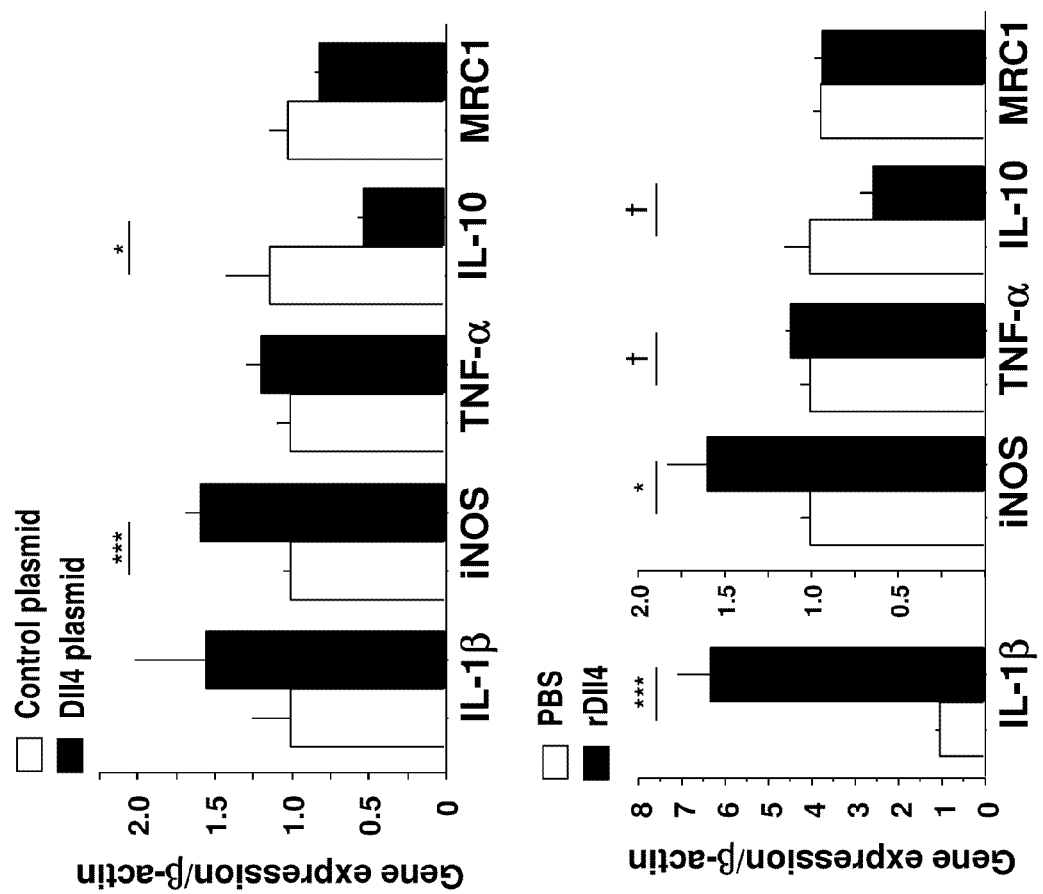
FIG. 11A depicts that enforced Dll4 expression and recombinant Dll4 (rDll4) induced expression of pro-inflammatory M1 genes such as IL-1β and iNOS and suppressed anti-inflammatory M2 genes (e.g., IL-10). In contrast.
Figure 11B:
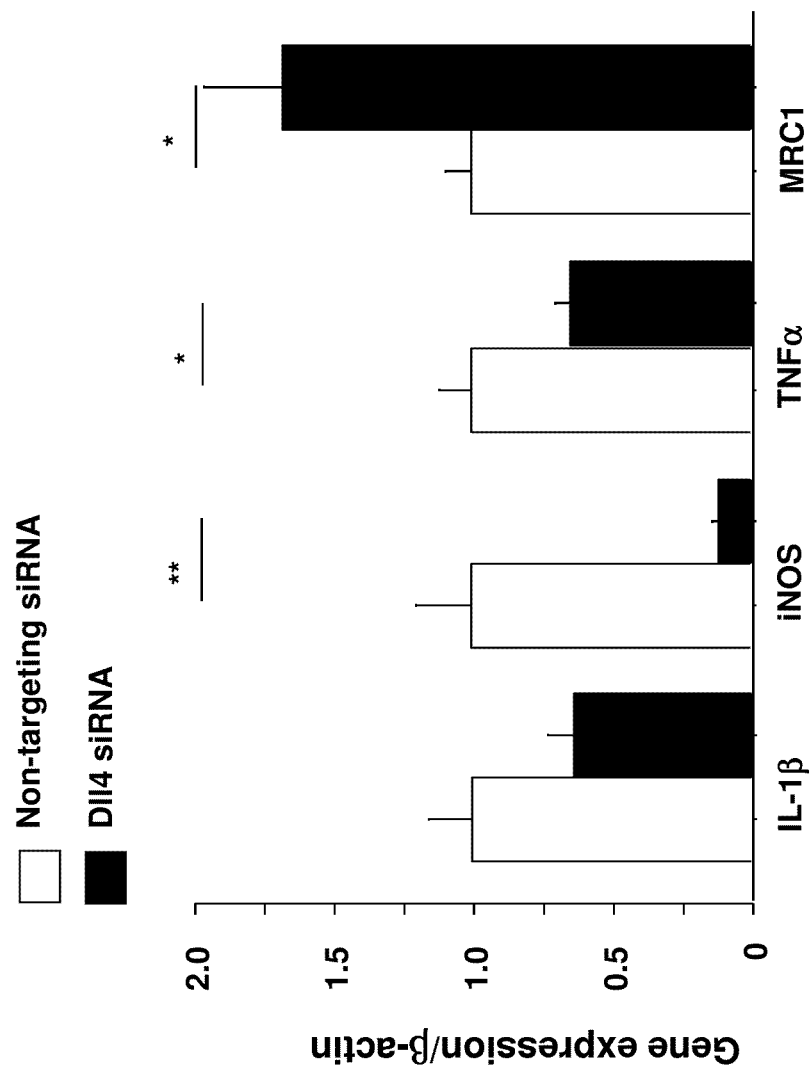
FIG. 11B depicts that Dll4 blockade reduced iNOS induction and increased the M2 gene MRC1.

In addition to the number of macrophages, phenotypic change of macrophages towards pro-inflammatory status results in acceleration of metabolic disorders (Chawla, *Circ Res* 106:1559-1569 (2010); Liang, et al., *Circ Res* 100:1546-1555 (2007)). Classically activated ("M1") macrophages express increased levels of pro-inflammatory genes (e.g., iNOS, IL-1β), while alternatively activated or anti-inflammatory ("M2") macrophages are represented by genes, including IL-10 and mannose receptor (MRC1). To address the mechanism by which Dll4 blockade improved metabolic disorders, Applicants tested the hypothesis that Dll4 promotes macrophage M1 polarization in vivo and in vitro. The effects of Dll4 blockade on inflammatory properties of macrophages were examined by flow cytometry using stromal vascular fraction (SVF) obtained from epididymal fat. Dll4 Ab administration tended to decrease Ly6C-high population in SVF, indicating reduction of the pro-inflammatory subpopulation of monocytes/macrophages (Swirski, et al., *J. Clin. Invest.* 117:195-205 (2007)), while producing no effect in blood and bone marrow (FIG. 9A-B). Furthermore, F4/80-positive macrophages collected from SVF of Ab-treated animals expressed lower levels of pro-inflammatory M1 molecules (e.g. iNOS, IFN-γ, and IL-6) and slightly higher levels of anti-inflammatory IL-10 (FIG. 10), concurring with Applicants' previous in vitro data on Dll4 binding to human primary macrophages (Fung, et al., *Circulation* 115:2948-2956 (2007)). Applicants then used gain- and loss-of-function systems using Dll4 expression vector and recombinant Dll4 (rDll4), and siRNA-mediated Dll4 silencing in macrophage-like cell line RAW264.7 to explore mechanisms underlying the observed inflammatory effects. Enforced Dll4 expression and rDll4 induced expression of pro-inflammatory M1 genes such as IL-1β and iNOS and suppressed anti-inflammatory M2 genes (e.g., IL-10) (FIG. 11A). In contrast, Dll4 blockade reduced iNOS induction and increased the M2 gene MRC1 (FIG. 11B). These results indicate that the Dll4-mediated signaling may serve as a molecular switch towards a pro-inflammatory phenotype of macrophages.

Figure 12A:
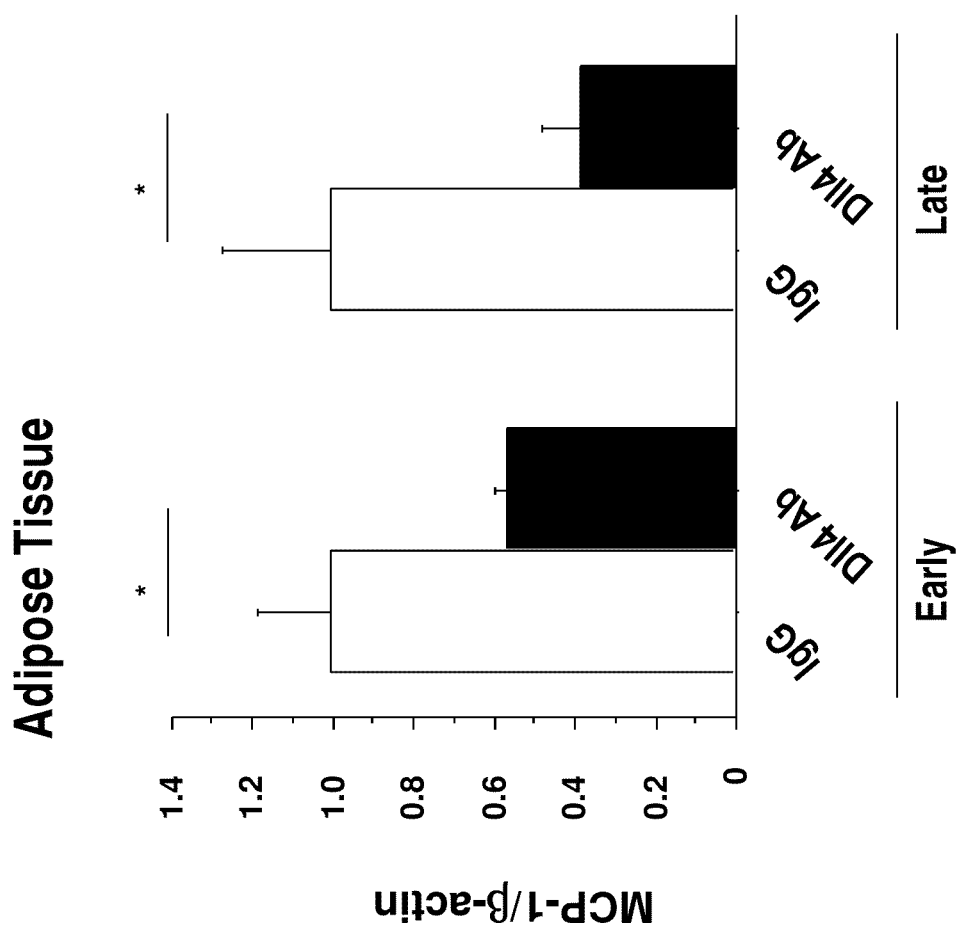
FIGS. 12A-C depict quantitative RT-PCR and ELISA for MCP-1 in adipocytes and SVF isolated from epididymal fat.
Figure 12B:
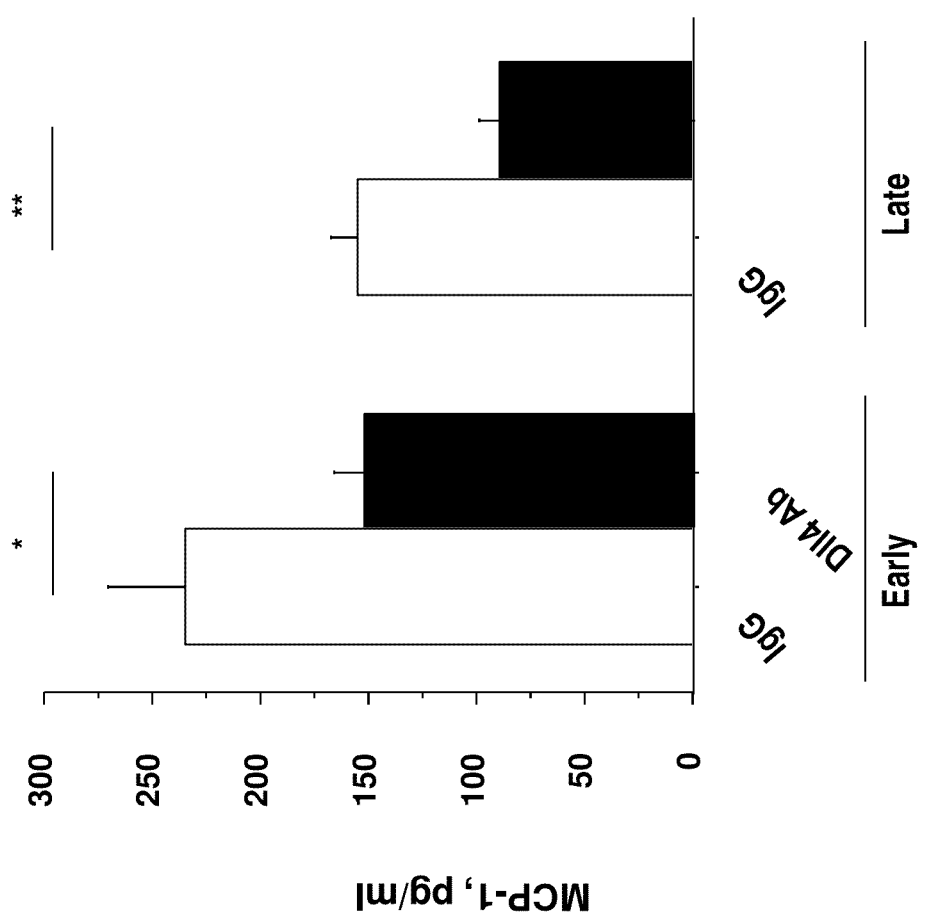
Figure 12C:
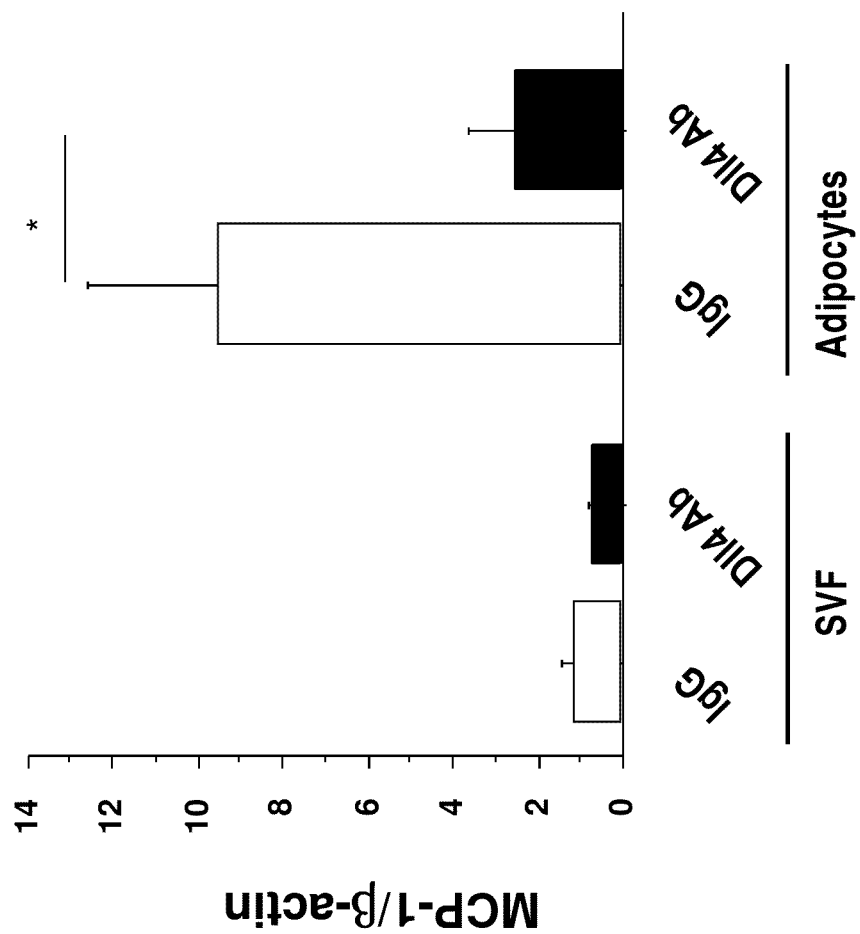

MCP-1 promotes accumulation of macrophages in adipose tissue and insulin resistance (Kanda, et al. *J. Clin. Invest.* 116:1494-1505 (2006)). To further explore the mechanisms by which Dll4 Ab treatment decreased macrophage accumulation in adipose tissue, the subsequent experiments focused on MCP-1. Along with RNA expression in epididymal fat, serum MCP-1 levels in Ab-treated mice were lower than those in IgG-treated mice (FIGS. 12A-B). Quantitative RT-PCR using adipocytes and SVF isolated from epididymal fat revealed that adipocytes were the major source of MCP-1 production (FIG. 12C). Dll4 Ab treatment reduced MCP-1 expression in adipocytes. Ab treatment also decreased Notch target gene Hey1 in adipocytes, suggesting suppression of Notch signaling.

Figure 13:
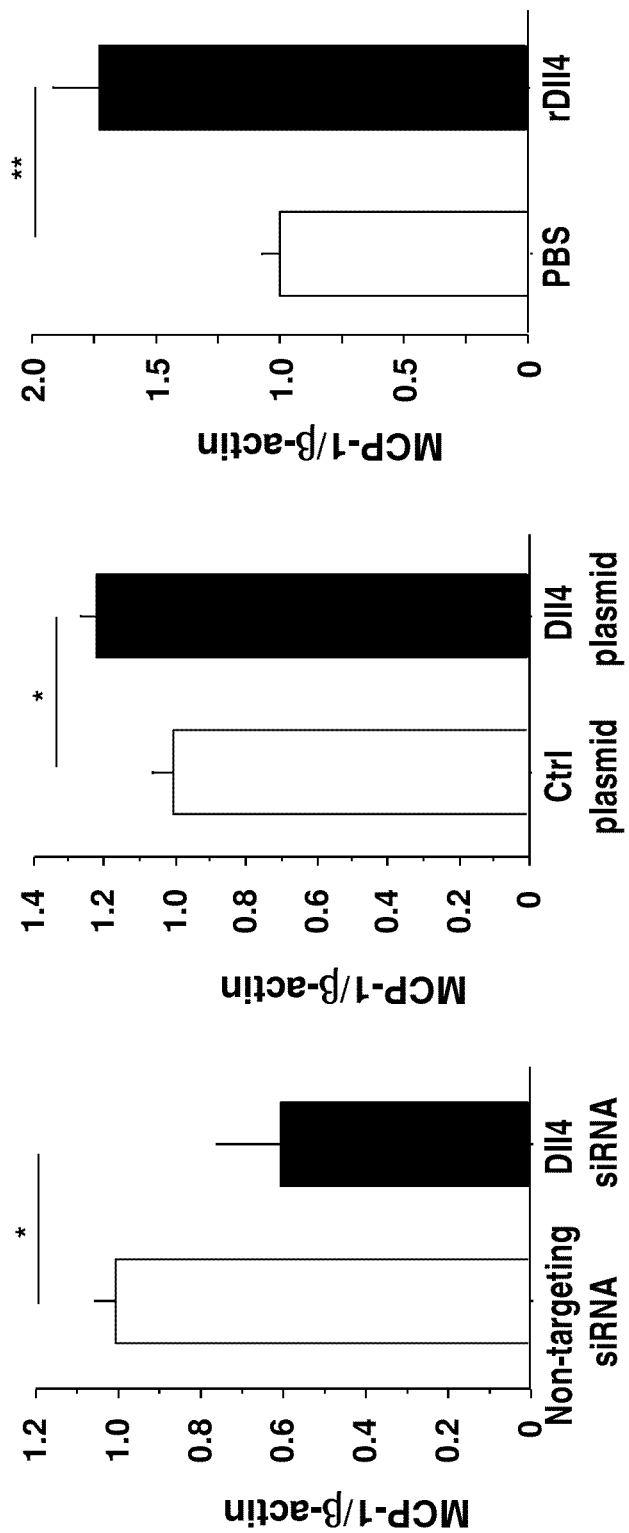
FIG. 13 depicts the effects of RNAi silencing of Dll4, enforced Dll4 expression, and rDll4 on MCP-1 mRNA expression.
Figure 14:
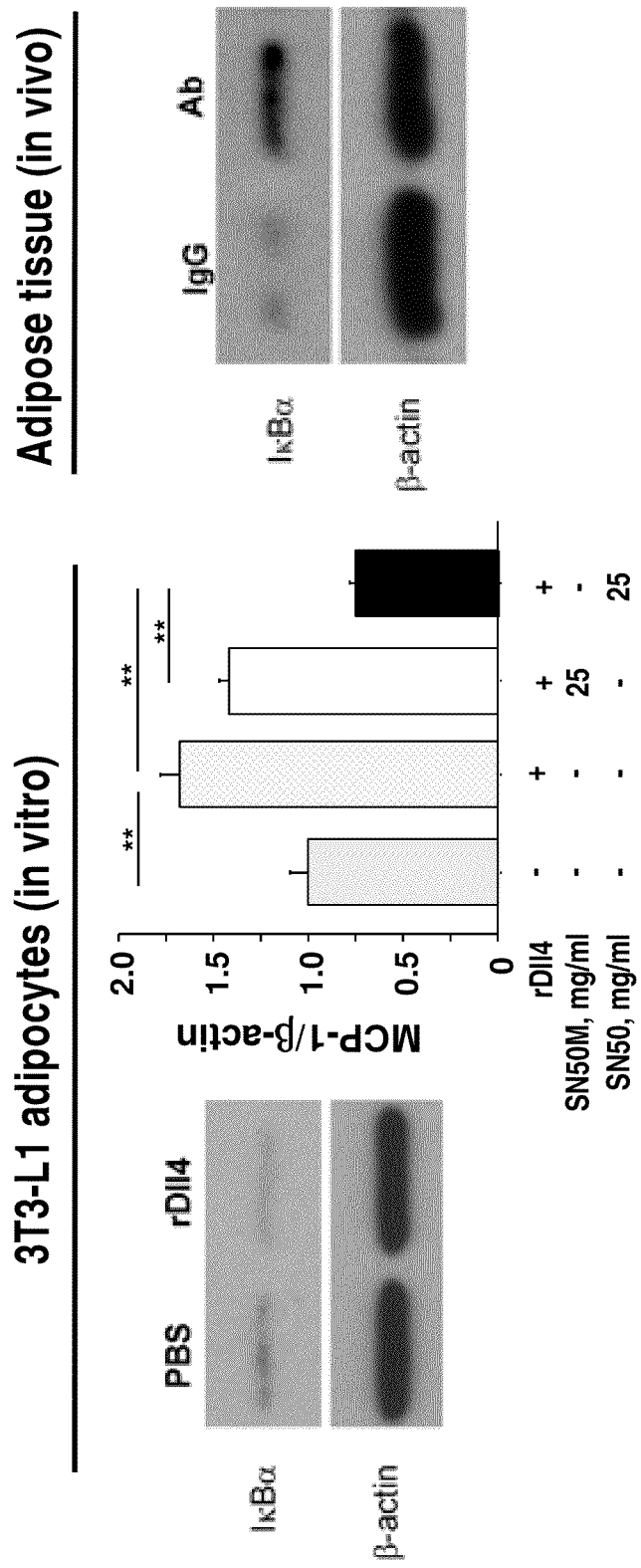
FIG. 14 depicts NF-κB activation by rDll4 (increased degradation of IκBα) and suppression of rDll4-induced MCP-1 expression by NF-κB inhibitor SN50 in 3T3-L1 adipocytes (left panel) and suppression of IκBα degradation in adipose tissue of Dll4 Ab-treated mice (right panel).

Loss-of-function and gain-of-function mechanistic studies further examined in vitro the causal role of Dll4 in MCP-1 expression in adipocytes, using differentiated 3T3-L1 adipocytes. RNAi silencing of Dll4 reduced MCP-1 RNA expression (FIG. 13). DAPT, a γ-secretase inhibitor that blocks Notch activation, produced a similar effect. Overexpression experiments using the Dll4-expressing plasmid increased MCP-1 expression (FIG. 13). To further determine whether Dll4 regulates MCP-1 expression, Applicants cultured 3T3-L1 adipocytes on dishes coated with rDll4. As shown, rDll4 promoted adipocyte MCP-1 expression (FIG. 13). Stimulation of Notch signaling by rDll4 was confirmed via RBP-Jκ reporter activity, which Dll4 Ab abrogated. The nuclear factor-KB (NF-κB) pathway promotes MCP-1 transcription, and Applicants previously demonstrated that Dll4-triggered Notch signaling induces NF-κB activation (Fung, et al., *Circulation* 115:2948-2956 (2007)). In the present study, rDll4 increased phosphorylation of NF-κB subunit p65, degradation of IκBα (FIG. 14, left panel), and nuclear translocation of p65 in 3T3-L1 adipocytes. SN50, a cell-permeable peptide inhibitor of NF-κB, abrogated Dll4-triggered MCP-1 induction (FIG. 14, center panel). These three independent experiments demonstrated that Dll4-mediated signaling stimulates the NF-κB pathway and MCP-1 expression. Furthermore, Applicants' in vivo evidence indicated that Dll4 Ab treatment inhibited NF-κB in epididymal fat (FIG. 14, right panel), supporting in vitro data. To further investigate whether Notch signaling indeed mediates MCP-1 induction, Applicants performed transient transfection of Notch3 intracellular domain (N3ICD) to adipocytes. N3ICD increased NF-κB p65 phosphorylation and MCP-1 expression.

Figure 15:
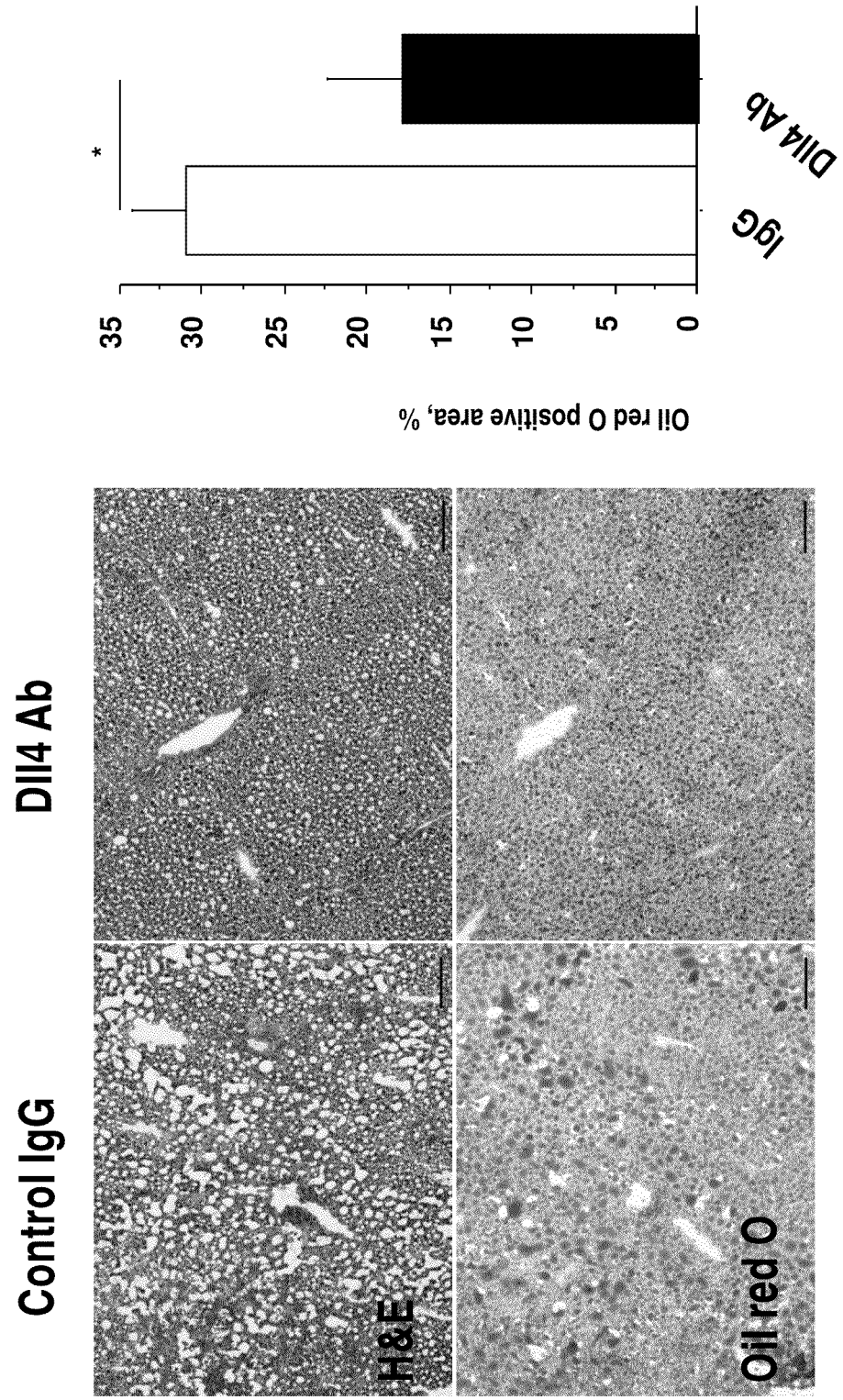
FIG. 15 depicts reduction of lipid deposition (oil red O staining) in the liver by Dll4 blockade, suggesting its effect on fatty liver.

Dll4 blockade improved several features typical of fatty liver, the key component of the cardiometabolic syndrome: 1) weight of liver, 2) lipid deposition (FIG. 15), 3) size of lipid droplets, and 4) infiltration of inflammatory cells. Weight of other organs did not differ significantly.

Figure 16:
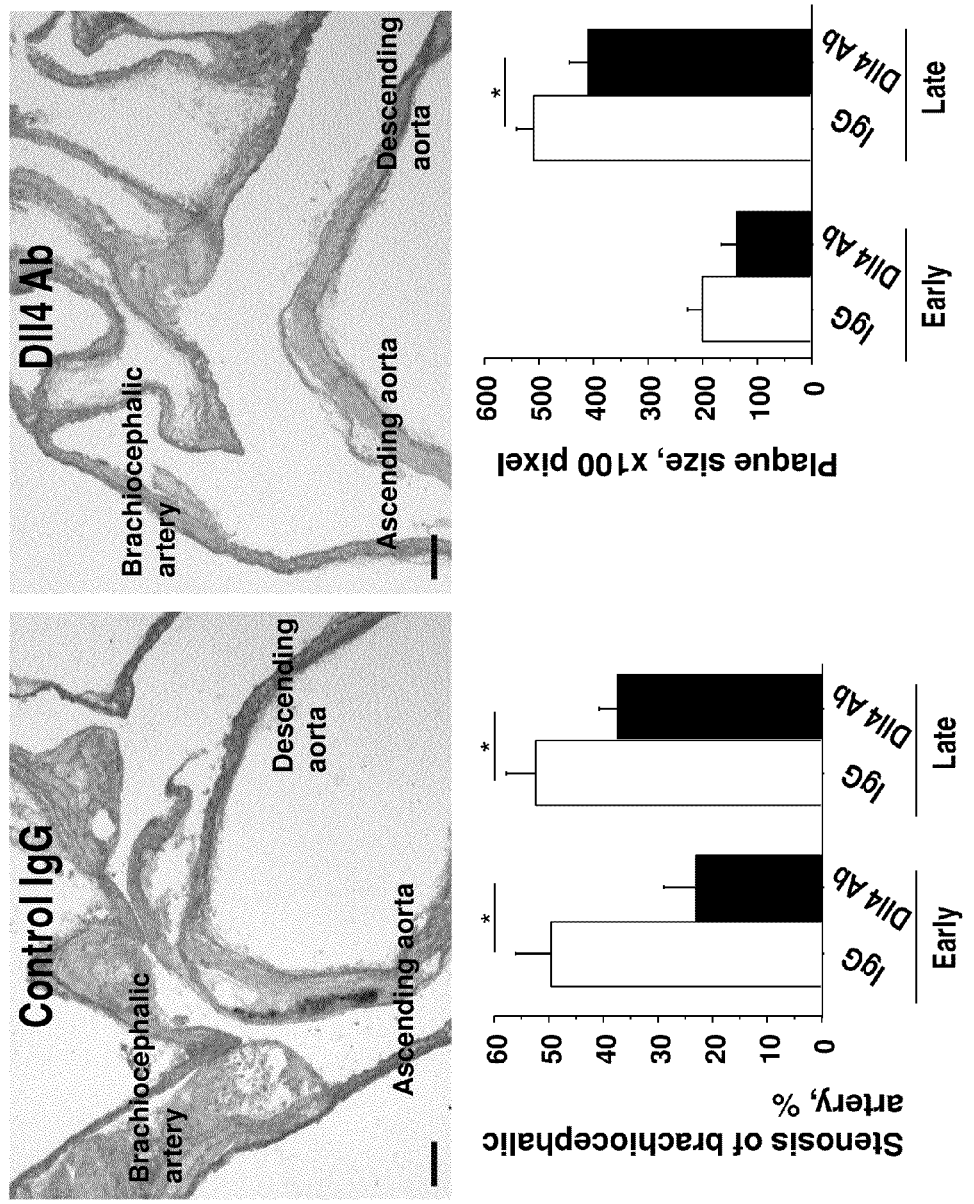
FIG. 16 depicts histological analyses of the aorta and brachiocephalic artery, demonstrating that Dll4 Ab treatment inhibited development of atherosclerotic plaques in the aorta and brachiocephalic artery.
Figure 17:
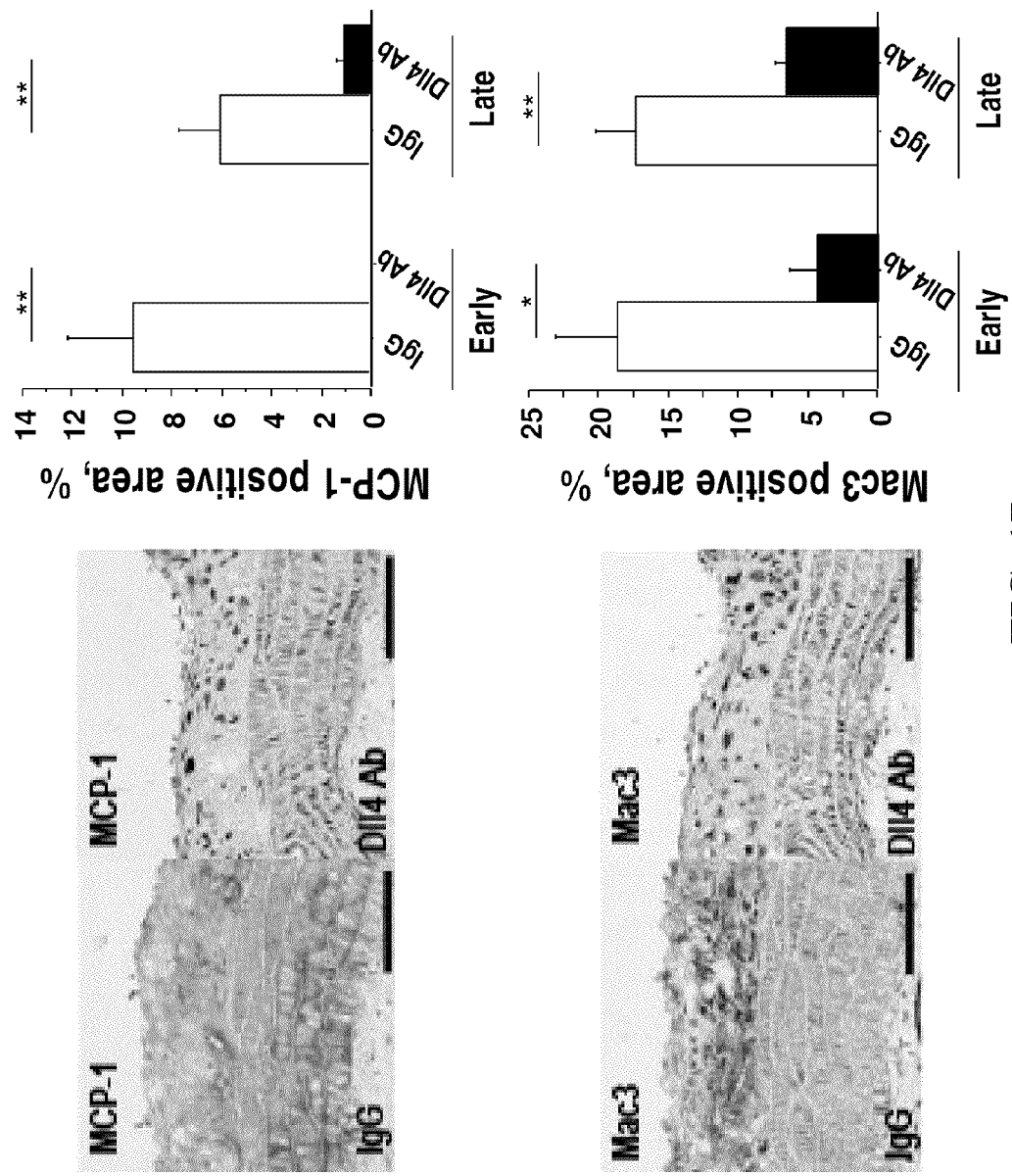
FIG. 17 depicts the effects of Dll4 Ab treatment on expression of MCP-1, a potent chemokine, and macrophage accumulation in the atherosclerotic aorta compared with the IgG group, suggesting a potential mechanism by which Dll4 promotes vascular inflammation.
Figure 18A:
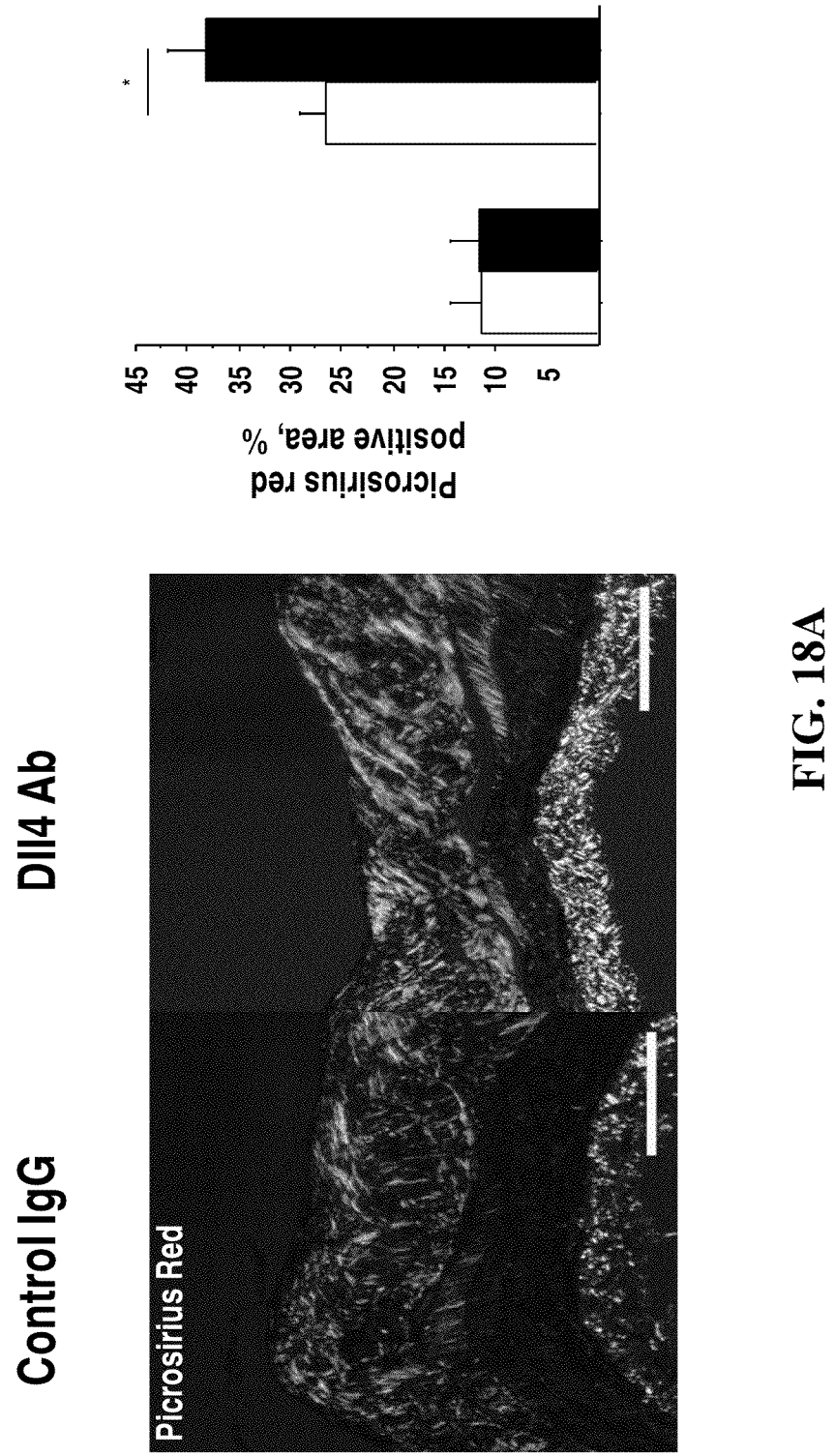
FIGS. 18A-C depicts picrosirius red staining demonstrating increased fibrillar collagen in plaques of Dll4 Ab-treated mice, and von Kossa staining (calcium deposits) and alkaline phosphatase (ALP) activity assay (osteogenic activity) indicating reduced calcification by Dll4 blockade.
Figure 18B:
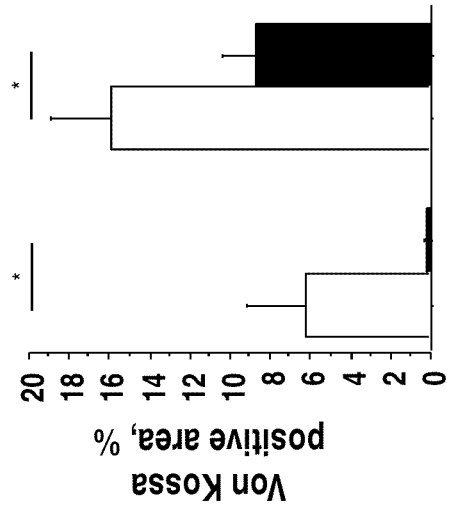
Figure 18B:
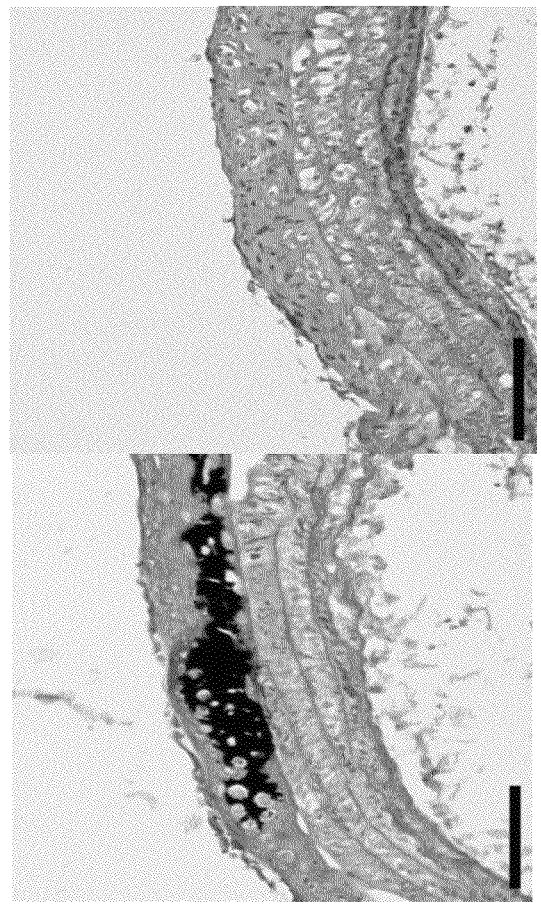
Figure 18C:
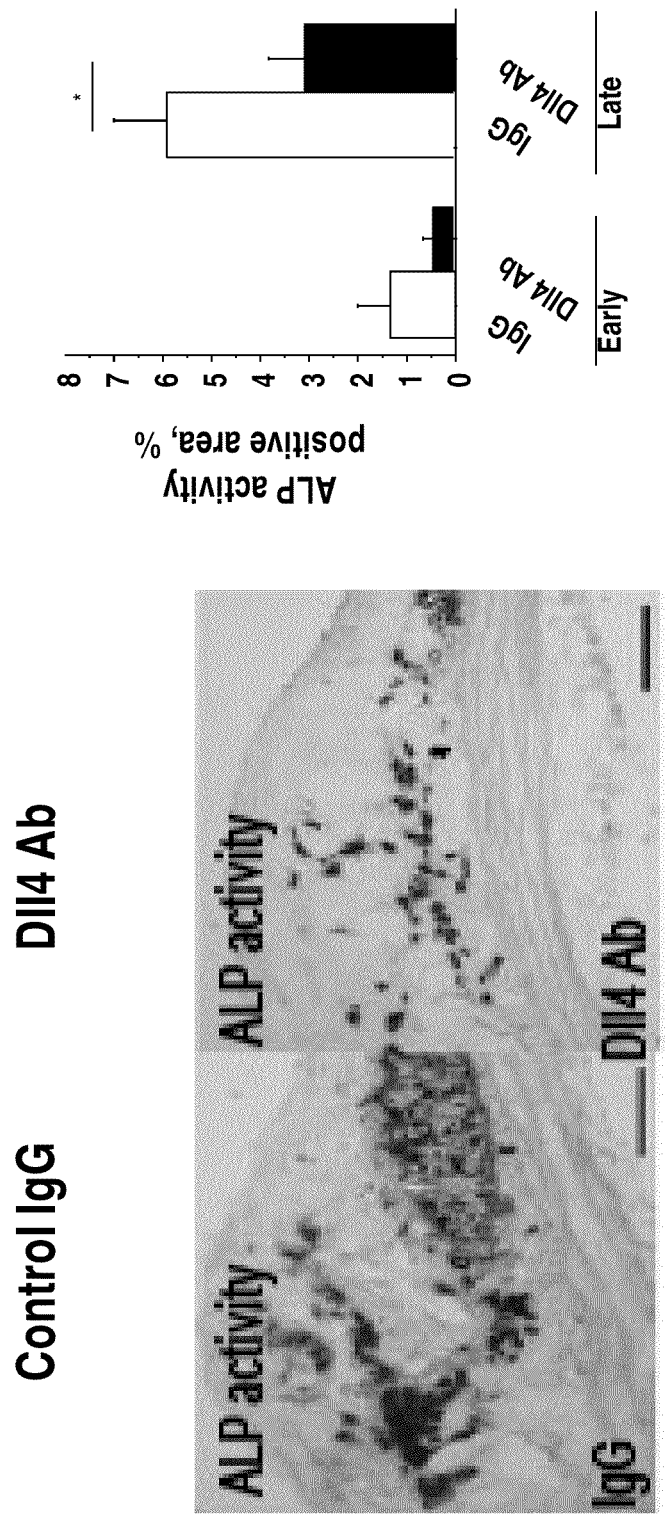
Figure 19:
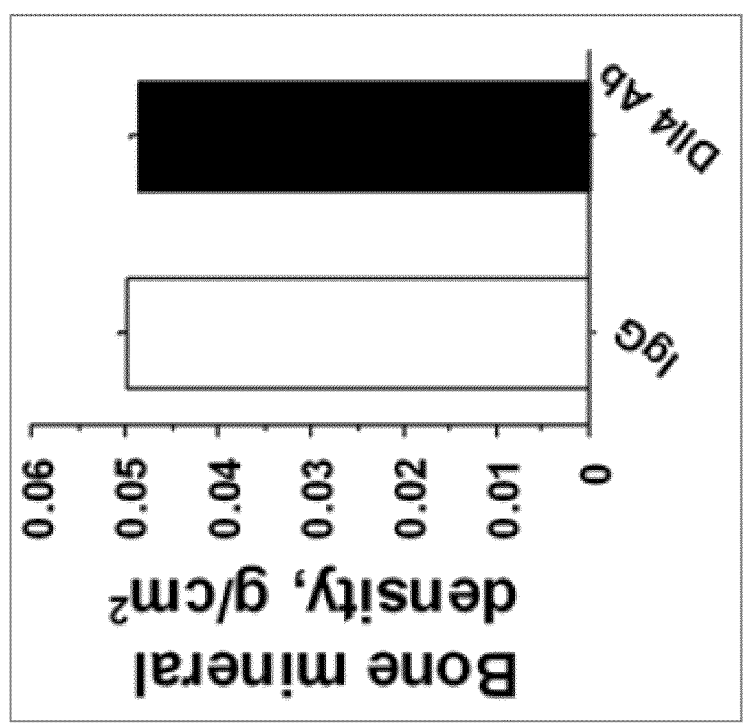
FIG. 19 depicts no appreciable effect of Dll4 blockade on bone mineral density.

Accelerated atherogenesis, a key component of the cardiometabolic syndrome, leads to acute thrombotic complications, the most common cause of death in patients with metabolic diseases. Histological analyses of the aorta and brachiocephalic arteries demonstrated that Dll4 blockade improved various features typical of atherosclerosis prone to acute events. Dll4 Ab-treated mice tended to have milder stenosis of brachiocephalic arteries and smaller atherosclerotic lesions in the aortic arch, especially in early-phase Ab administration (FIG. 16). Dll4 Ab treatment decreased MCP-1 expression and macrophage accumulation in the atherosclerotic aorta compared with the IgG group (FIG. 17). Applicants and others have established the role of macrophage production of proteinases in collagen loss and atherosclerotic plaque "instability," leading to acute vascular events (Aikawa, et al., *Cardiovasc. Pathol.* 13:125-138 (2004)). Picrosirius red staining demonstrated increased fibrillar collagen in plaques of Dll4 Ab-treated mice (FIG. 18A). Several studies, including Applicants' own, demonstrated that macrophages promote arterial calcification (Aikawa, et al., *Circulation* 119:1785-1794 (2009)) and may cause acute vascular complications (Abedin, et al., *Arterioscler. Thromb. Vasc. Biol.* 24:1161-1170 (2004)). Furthermore, evidence indirectly suggests that Notch regulates calcification (Shimizu, et al., *Arterioscler. Thromb. Vasc. Biol.* 29:1104-1111 (2009)). Dll4 Ab treatment significantly decreased calcified areas and alkaline phosphatase (ALP) activity in atherosclerotic lesions (FIGS. 18B-C). Molecular imaging using fluorescence reflectance demonstrated ex vivo that macrophage-targeted fluorescent signal correlated well with osteogenic activity, both of which decreased with Ab treatment in parallel. Aortic valve calcification, an inflammatory disorder leading to aortic stenosis and heart failure, is also a major burden in clinical practice (Aikawa, et al., *Circulation* 119:1785-1794 (2009); Towler, *J. Am. Coll. Cardiol.* 52:851-854 (2008)). Dll4 blockade tended to decrease thickness of aortic valve leaflets, and osteogenic activity. While Dll4 blockade suppressed ectopic cardiovascular calcification, this treatment did not decrease bone mineral density (FIG. 19). Aortic expression of the Notch target gene Hey2 decreased in Dll4 Ab-treated animals, indicating suppression of Notch signaling.

Figure 20A:
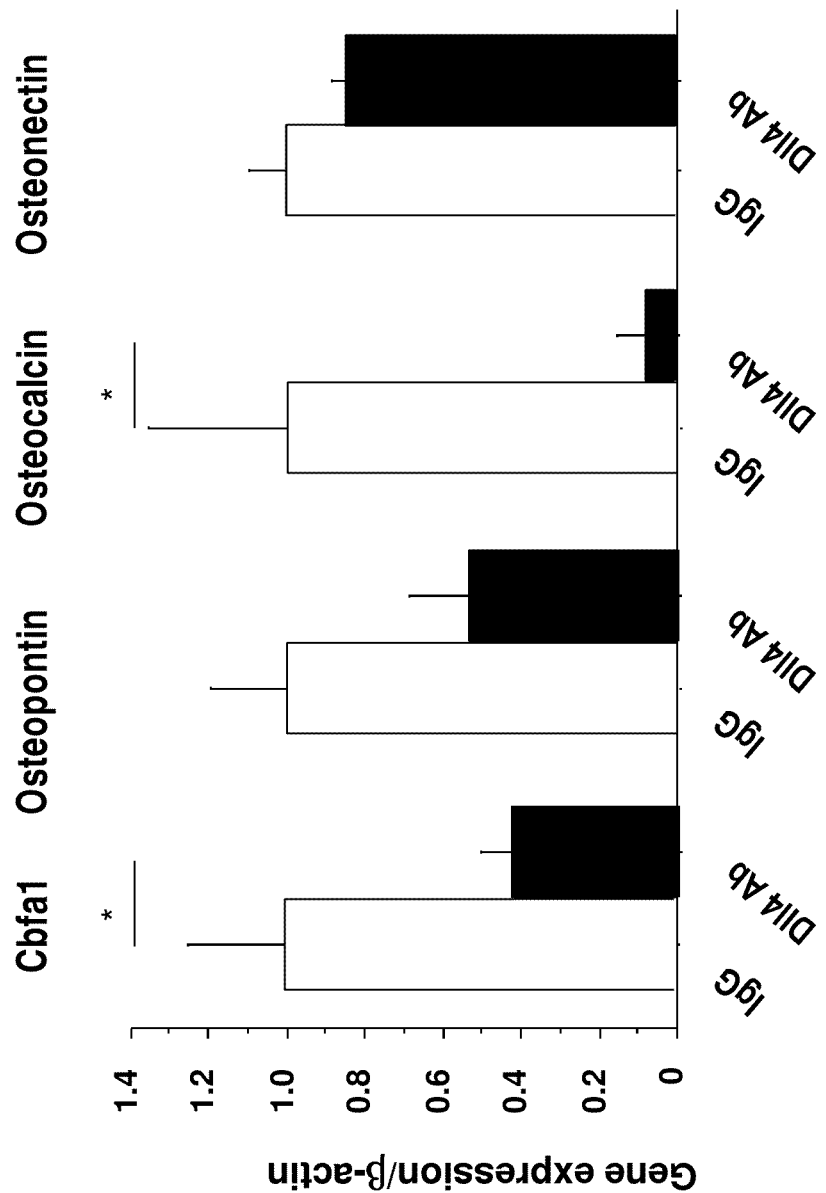
FIGS. 20A-C depict the effects of Dll4 Ab treatment on the expression of osteogenic regulators, bone morphogenetic proteins (BMPs), and matrix metalloproteinases (MMPs) in extracts from the aorta.
Figure 20B:
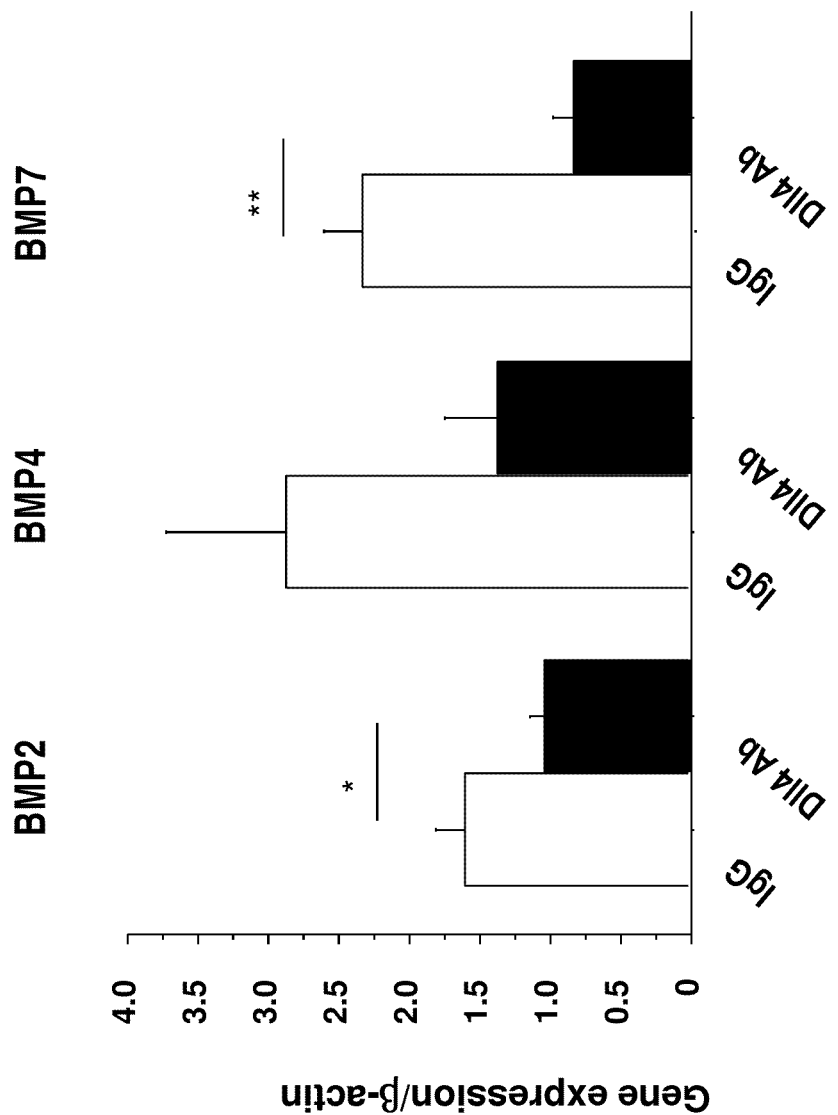
Figure 20C:
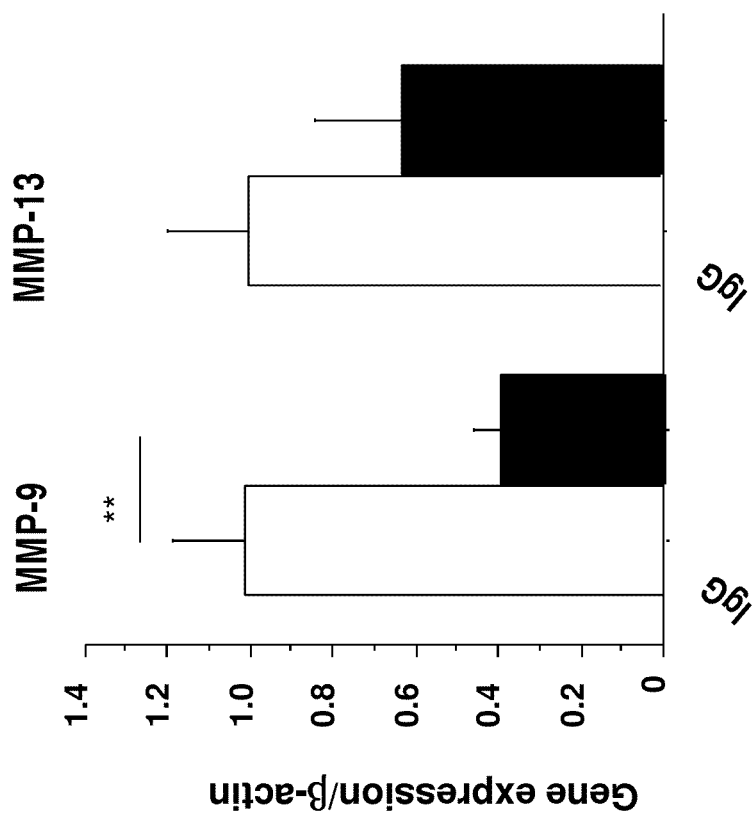
Figure 21:
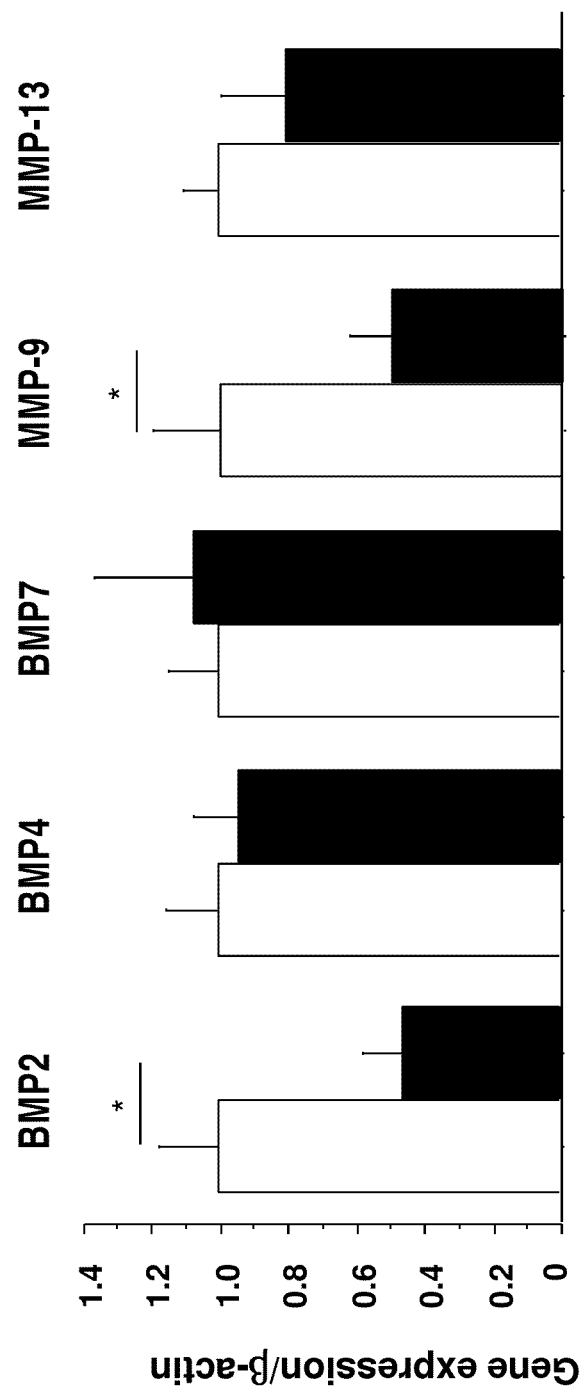
FIG. 21 depicts phenotype of macrophages derived from Dll4 Ab-treated mice, as demonstrated by mRNA expression of BMPs and MMPs.

Applicants explored molecular mechanisms of decreased plaque inflammation and calcification, and increased collagen by Dll4 blockade. In consistent with reduced calcification, Dll4 Ab treatment significantly decreased expression of osteogenic regulators and bone morphogenetic proteins (BMPs) in extracts from the aorta (FIGS. 20A-B). Ab treatment reduced the aortic expression of MMP-9/gelatinase-A and MMP-13/collagenase-3, major enzymes responsible for collagen loss (FIG. 20C). Because macrophages promote calcification and matrix degradation, Applicants further examined phenotype of macrophages derived from Ab-treated mice. In peritoneal macrophages, Dll4 Ab decreased BMP2 and MMP-9 expression (FIG. 21). In addition, complementary in vitro experiments using the plasmid encoding Dll4 and Dll4 Ab in RAW264.7 cells indicated that Dll4 promotes MMP-9 expression.

C. Discussion

A high-fat, high-cholesterol diet promoted Dll4 expression in both white adipose tissue and atheromata in LDL receptor-deficient (Ldlr$^{-/-}$) mice. Dll4 antibody (Ab) treatment in Ldlr$^{-/-}$ mice for 12 weeks retarded body weight gain, reduced fat weight, and improved insulin resistance. These changes were accompanied by diminished expression of MCP-1 and macrophage accumulation in adipose tissue, and lower levels of NF-κB activation. In vitro experiments with differentiated 3T3-L1 adipocytes revealed that Dll4-mediated Notch signaling promotes MCP-1 expression via NF-κB activation, providing a possible mechanism for these effects. Dll4 Ab also reduced MCP-1 expression, plaque burden, macrophage content, and calcification in atherosclerotic plaques and the degree of fatty liver in Ldlr$^{-/-}$ mice. These results suggest that the Dll4-Notch signaling axis is a potential common mechanism for the pathogenesis of cardiometabolic syndrome.

Example 2

Notch3 Signaling in Macrophages Promotes Obesity, Atherosclerosis and Arterial Calcification in Hypercholesterolemic Mice To test the hypothesis that Notch signaling in macrophages promotes cardiometabolic disorders, including obesity, metabolic syndrome, atherosclerosis and vascular calcification, macrophage-selective Notch3-ICD transgenic (Notch3tg) mice under control of the macrophage SR-A promoter/enhancer were used. The findings from the study suggest that Notch3 signaling induces a proinflammatory macrophage phenotype and that Notch3 activation in macrophages promotes atherosclerosis, arterial calcification, and visceral fat obesity in vivo.

A. Methods

Animal Preparation

All experiments conform to a protocol approved by the Standing Committee on Animals of Harvard Medical School. Two independent macrophage-selective Notch3 intracellular domain transgenic (Notch3tg) mice were established under the control of the macrophage scavenger receptor A (SR-A) promoter/enhancer by gene targeting in embryonic stem cells. A FLAG-epitope-tagged Notch3-ICD cDNA fragment (2.0 kb) was inserted downstream of the SR-A promoter/enhancer (5.0 kb). Line 1 of Notch3tg mice, which had a higher copy number than line 2, were then crossed into LDL receptor knockout mice (Ldlr$^{-/-}$) to render Notch3Tg mice atherosclerosis susceptible, yielding Notch3tg:Ldlr$^{-/-}$ and Ldlr-/- mice. Eight-week-old male Notch3tg:Ldlr-/- mice and Ldlr-/- littermates (n=10 each) were given a high fat and high cholesterol diet (Clinton/Cybulsky high fat rodent diet with 1.25% cholesterol, Research Diets) for 24 weeks.

To examine if Notch3 deficiency affects cardiometabolic syndrome, Nocth3−/− mice were crossed into Ldlr−/− mice to render Notch3−/− mice atherosclerotic susceptible, yielding Notch3−/−:Ldlr−/− mice. Eight-week-old male Notch3−/−: Ldlr−/− mice and Ldlr−/− littermates (n=10 each) were fed a high fat and high cholesterol diet for 20 weeks.

Histological Analysis

Aorta samples were frozen in OCT compound, and 5-1 μm serial sections were cut and stained with hematoxylin and eosin for general morphology. Oil red O staining was used to detect lipid deposits Alkaline phosphatase activity (a marker of early osteogenic differentiation) was detected on cryosections according to the manufacturer's instructions (alkaline phosphatase substrate kit, Vector Laboratories, Burlingame, Cal.). Von Kossa silver stain was used to histochemically image advanced calcification. Immunohistochemistry with rat monoclonal antibody against mouse Mac3 (BD Biosciences) was performed to detect macrophage accumulation. For quantification of histological assays, captured photomicrographs are transferred into an image analysis system (ImagePro Plus 5.1, Media Cybernetics).

Epididymal fat was fixed with 4% paraformaldehyde solution and embedded in paraffin, and 5-1 μm serial sections were cut and stained with hematoxylin and eosin, before area measurement (ImageJ software) in more than 5 representative images and 150 cells per mouse. Immunohistochemistry with rat monoclonal antibody against mouse Mac3 (BD Pharmingen) were performed. Positive cells were counted in 10 consecutive visual fields at the same magnification, and positive staining area is calculated using an image analysis system as described above.

Body Composition

Total body weight, epididymal fat weight and subcutaneous fat weight were measured. Notch3tg:Ldlr−/− mice and Ldlr−/− littermates (n=5 each) were subjected to dual-energy X-ray absorptiometry (DEXA) for body composition analysis.

Lipids and Cytokines

Serum cholesterol and triglyceride levels are determined by kits (Cholesterol E Kit and LabAssay™ Triglyceride Kit; Wako Chemicals). Serum Leptin levels were determined by Mouse Leptin Elisa Kit (Crystal Chem INC).

Isolation of Mouse Peritoneal Macrophages

Twenty-week-old male Notch3tg mice and male wild type littermates (n=6 each), and 20-week-old male Notch3−/−: Ldlr−/− mice and male Ldlr−/− littermates (n=5 each) fed on high fat and high cholesterol diet for 12 weeks were prepared. Three days after an intraperitoneal injection of 4.0% thioglycolate, primary peritoneal macrophages were harvested from mice, and cultured with Dulbecco's modified Eagle's medium (DMEM). After incubation with DMEM for 1 hour, the culture media of adherent cells was changed to fresh DMEM with 10% fetal bovine serum (FBS). After incubation for 72 hours, adherent cells were harvested.

Effect of LPS Treatment on Notch3 Expression in Mouse Primary Macrophages

Peritoneal macrophages were isolated from C57BL/6 mice (n=3) as described above. After physiological concentration of LPS (5 ng/ml) treatment for 1 and 3 hours, adherent cells were harvested.

Lipid Accumulation and Expression of Scavenger Receptors in Peritoneal Macrophages on Atherogenic Diet Eight-week-old male Notch3tg:Ldlr−/− and Ldlr−/− littermates consumed a high fat and high cholesterol diet for 12 weeks. Peritoneal macrophages were extracted from those mice and cultured with DMEM. After incubation for 1 hour, adherent cells were stained with Oil red 0 staining and harvested for extraction of total RNA and proteins.

Isolation of Adipocytes and Macrophages from Epididymal Fat

Epididymal fat from male Notch3tg:Ldlr−/− mice and Ldlr−/− littermates (n=5 each) after 24 weeks on high fat and high cholesterol diet was minced in PBS containing 2% bovine serum albumin (BSA) and 250 U/ml of collagenase type II (Worthington) and was incubated at 37° C. for 50 min. The digested tissue was passed through a 70-1 μm cell strainer (BD Biosciences) and the flow-through centrifuged and floating cells were collected as the adipocytes. After aspirating the supernatant, red blood cells were lysed with ACK lysing buffer (Gibco), and the remaining cells are collected as the stromal vascular cells (SVCs). Macrophages (CD11b-positive cells) and CD11b-negative cells are isolated from the SVCs, using anti-CD11b labeled magnetic beads (Miltenyi Biotec, Inc., Auburn, Calif.).

Indirect Effect of Notch3 Activated Macrophages on Differentiated Adipocytes

Peritoneal macrophages isolated from male Notch3tg: Ldlr−/− mice and Ldlr−/− littermates (n=5 each) after 12 weeks on high fat and high cholesterol diet were cultured with DMEM with 10% FBS for 72 hours, and the culture media is changed to fresh DMEM. After incubation with DMEM for 24 hours, the condition media was collected. Murine 3T3-L1 preadipocytes are cultivated and are differentiated for 10 days as previously described. After serum starvation for 24 hours, differentiated cells were stimulated with the condition media (n=5 each), and harvested an hour after stimulation.

Real-Time Reverse-Transcription Polymerase Chain Reaction

Total RNA was isolated from tissue and cells with an RNAspin Mini RNA isolation Kit (GE Healthcare, Buckinghamshire, UK). Polymerase chain reaction detection and quantification of Notch3ICD, Notch3, IL-1β, iNOS, TGF-β, mannose receptor, arginase 1, MCP-1, PTX3, PAI-1, CD36, SR-A, LOX-1, BMP-2, BMP-4, BMP-7, leptin, TNF-α, adiponectin, FABP4, IL-6, HSL, and ATGL was done with a MyiQ single-color real-time PCR detection system and iQ SYBR Green Supermix (BioRad, Hercules, Calif.). Quantitative PCR values were normalized by β-actin. Relative fold changes are calculated by the comparative threshold cycles ($C_T$) method, $2^{-\Delta\Delta C_T}$.

Western Blotting

After lysis in solubilization buffer, immunoblotting was performed as described before, using specific antibodies against amino acids of Notch3, CD36 (both from Santa Cruz Biotechnology Inc), IκB-α (from Cell Signaling Technology), and β-actin (from Sigma-Aldrich), before densitometric analysis (ImageJ software).

Determination of the Transgene Copy Number

Mouse tail DNA was extracted using DNeasy Blood and Tissue Kit (QIAGEN). Transgene copy number was determined in both line 1 and line 2 of N3Tg mice by real-time PCR using the human SR-A primers as previously described. Human genomic DNA was used to generate a standard curve. The primer combination for human SR-A was: forward primer: 5-GCTTGTTTCAACAACCCTTG-3 (SEQ ID NO: 1) and reverse primer: 5-ATGACACATTCCTGCGTTGA-3 (SEQ ID NO: 2).

Statistical Analysis

Mann-Whitney U test was performed when 2 groups were compared. Data are presented as mean±SEM. P values<0.05 are considered significant.

B. Results

Establishment of Macrophage-Selective N3ICDTg Mice

Figure 22:
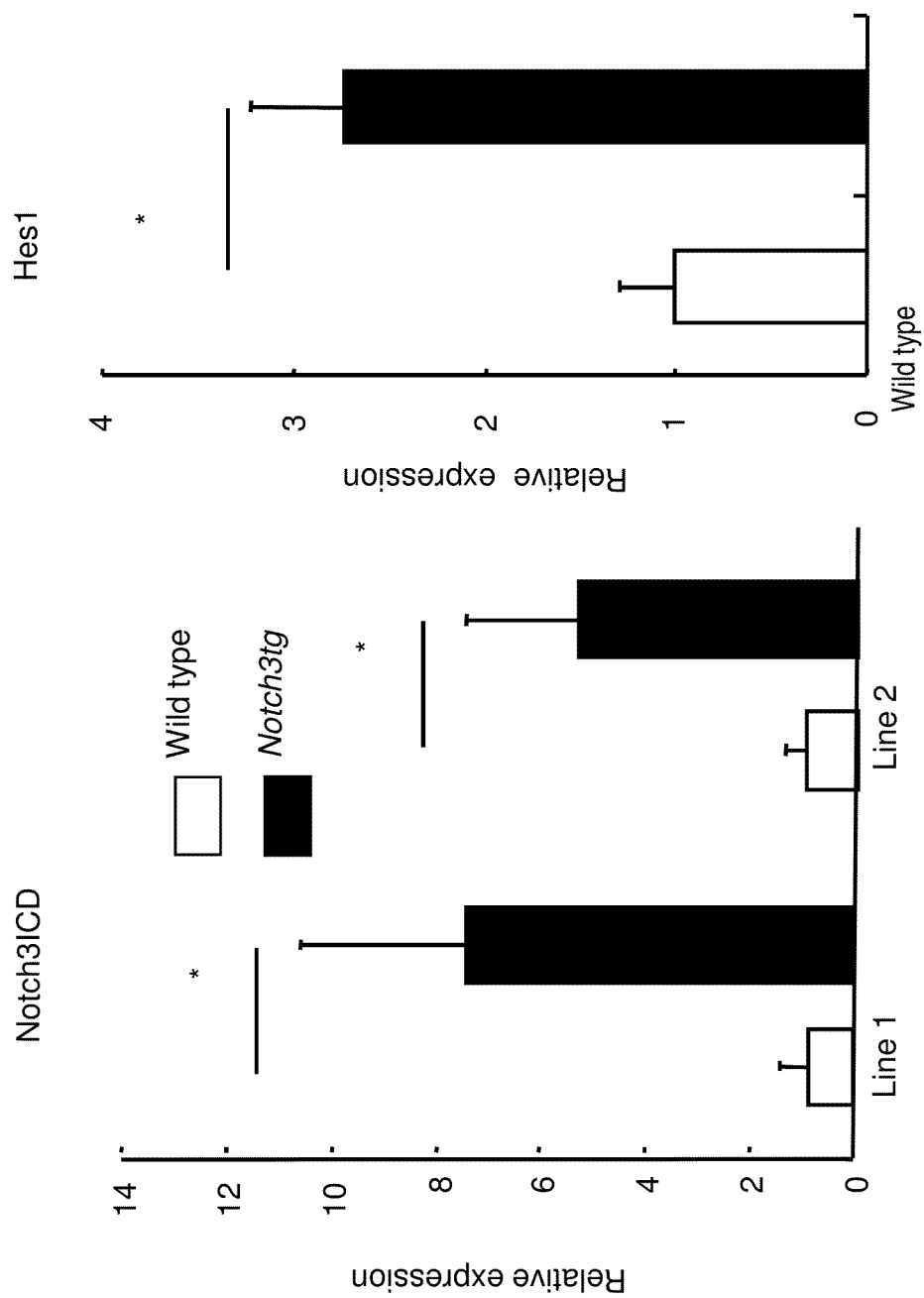
FIG. 22 depicts mRNA expression of Notch3ICD of peritoneal macrophages of 2 independent lines (Lines 1 and 2) of macrophage-selective Notch3-ICD transgenic (Notch3tg) mice under control of the macrophage scavenger receptor A (SR-A) promoter/enhancer. Expression of the prototypical Notch target gene Hes1 was higher in Notch3tg mice as compared to wild type mice, suggesting that enforced expression of NotchICD induced Notch signaling.

Applicants established 2 independent lines (Lines 1 and 2) of macrophage-selective Notch3-ICD transgenic (Notch3tg) mice under control of the macrophage scavenger receptor A (SR-A) promoter/enhancer. The estimated numbers of transgene copies were 59 copies (58.8±0.3, n=4) in Line 1 and 16 copies (16.1±0.2, n=4) in Line 2, respectively. Peritoneal macrophages of both Lines 1 and 2 Notch3tg mice showed approximately 8 and 5 times higher mRNA expression of Notch3ICD compared to respective wild type littermates (FIG. 22). Applicants used Line 1 of Notch3tg mice for the following experiments due to a larger number of transgene copies and higher expression of Notch3-ICD mRNA. A physiological concentration of LPS (5 ng/ml) increased about 10 times Notch3ICD mRNA levels in peritoneal macrophages from wild type mice in time dependent manner, suggesting peritoneal macrophages isolated from Notch3tg mice do not express exaggerated levels of Notch3ICD mRNA. Line 1 of Notch3tg mice also expressed higher levels of Hes 1 mRNA (FIG. 22), the conventional target gene of Notch signaling, in peritoneal macrophages, compared with littermate control mice. Furthermore, peritoneal macrophages of Notch3tg:Ldlr−/− mice fed on high fat and high cholesterol diet for 12 weeks expressed greater amount of Notch3-ICD protein (97 kDa) than those of Ldlr−/− littermates whereas full-length of Notch3 (281 kDa) did not differ between 2 groups.

Notch3 Signaling Pathway Regulate Macrophage Activation

Figure 23:
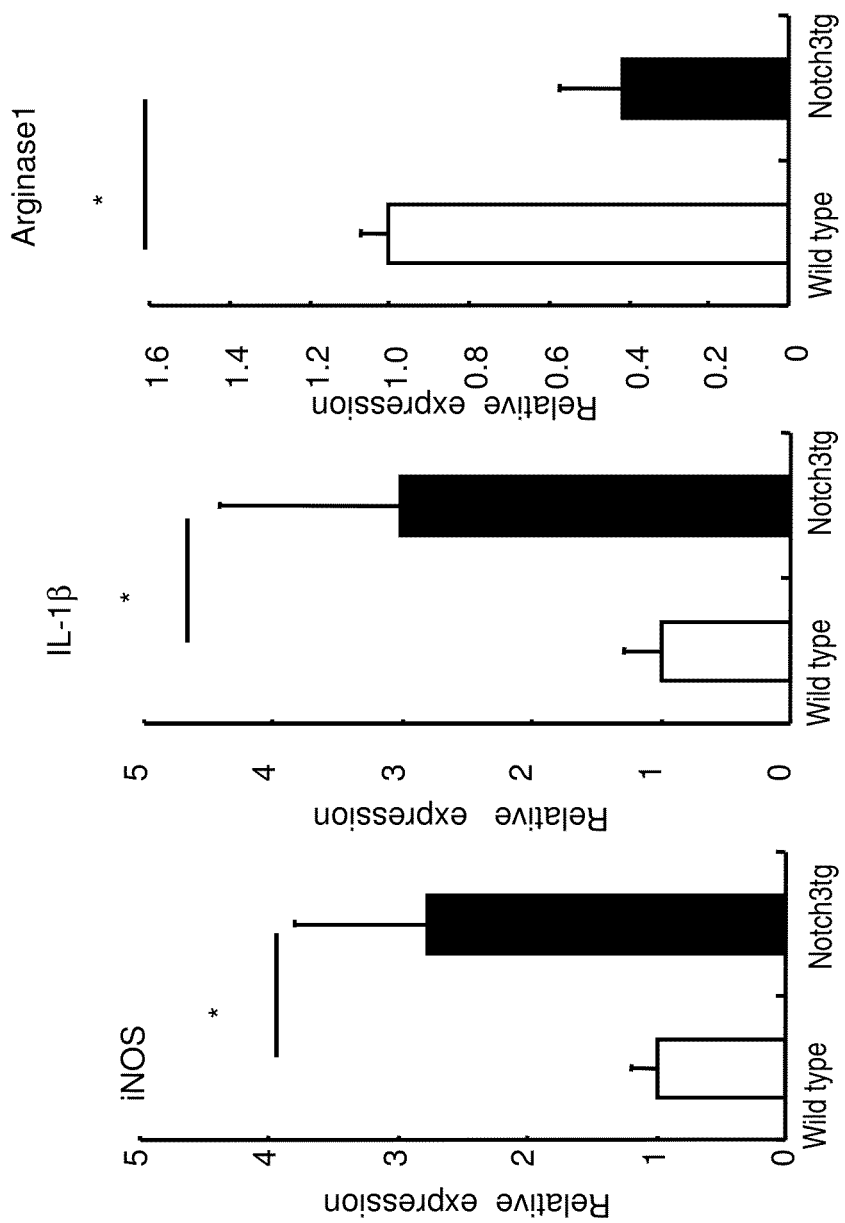
FIG. 23 depicts increased mRNA levels of iNOS and IL-1β in peritoneal macrophages obtained from Notch3tg mice, while these Notch3tg macrophages expressed lower mRNA levels of arginase 1.

Macrophage activation as gauged by proinflammatory molecules plays a key role in chronic inflammatory disorders including atherosclerosis and obesity. Inducible nitric oxide synthase (iNOS), an injurious factor associated with the oxidative burst of macrophages and various inflammatory diseases, represents a commonly used marker for these proinflammatory phagocytes. Peritoneal macrophages obtained from Notch3tg mice expressed a higher mRNA level of iNOS than those from wild type littermates (FIG. 23). Notch3tg macrophages also showed higher expression of IL-1β, a pluripotent proinflammatory cytokine. These data in Notch3tg mice suggest a "classical M1 form" of macrophage activation. M1 macrophage polarization generally promotes cytotoxic and inflammatory functions. In contrast, these Notch3tg macrophages expressed a lower level of arginase 1 mRNA (FIG. 23), a molecule generally considered to be associated with "alternatively" activated, anti-inflammatory macrophages (M2).

Figure 25:
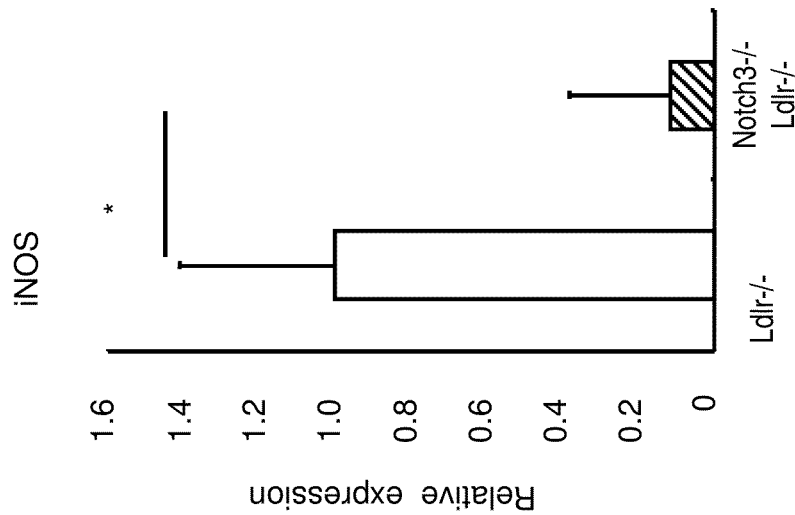
FIG. 25 depicts Notch3 deletion in Notch3 deficient (Notch3−/−) mice resulted in decreased iNOS expression in peritoneal macrophages as compared with control sibling littermates.
Figure 24:
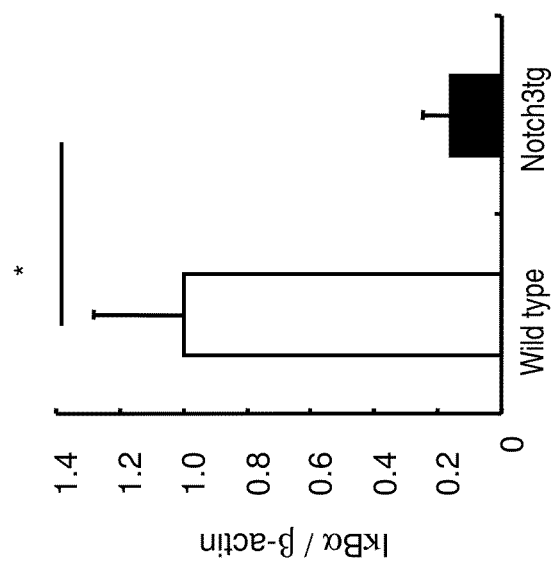
FIG. 24 depicts enforced expression of Notch3-ICD induced NF-κB activation in peritoneal macrophages of Notch3tg mice, as indicated by decreased accumulation of the endogenous inhibitor by IκBα.

NF-κB activation is a pleiotropic proinflammatory transcription factor. Enforced expression of Notch3-ICD induced NF-κB activation in peritoneal macrophages of Notch3tg mice, as indicated by decreased accumulation of the endogenous inhibitor by IκBα (FIG. 24). To further address the role of Notch3 in shifting macrophage polarization toward a proinflammatory phenotype, Applicants employed a loss-of-function approach with Notch3-deficient (Notch3−/−) mice. In peritoneal macrophages, Notch3 deletion decreased iNOS expression as compared with control sibling littermates (FIG. 25), providing an opposing finding to Notch3-ICD expression. Collectively, these results suggest that Notch3 signaling tends to promote a proinflammatory population of macrophages.

Notch3 Signaling Avravates Macrophage Foam Cell Formation

Figure 26:
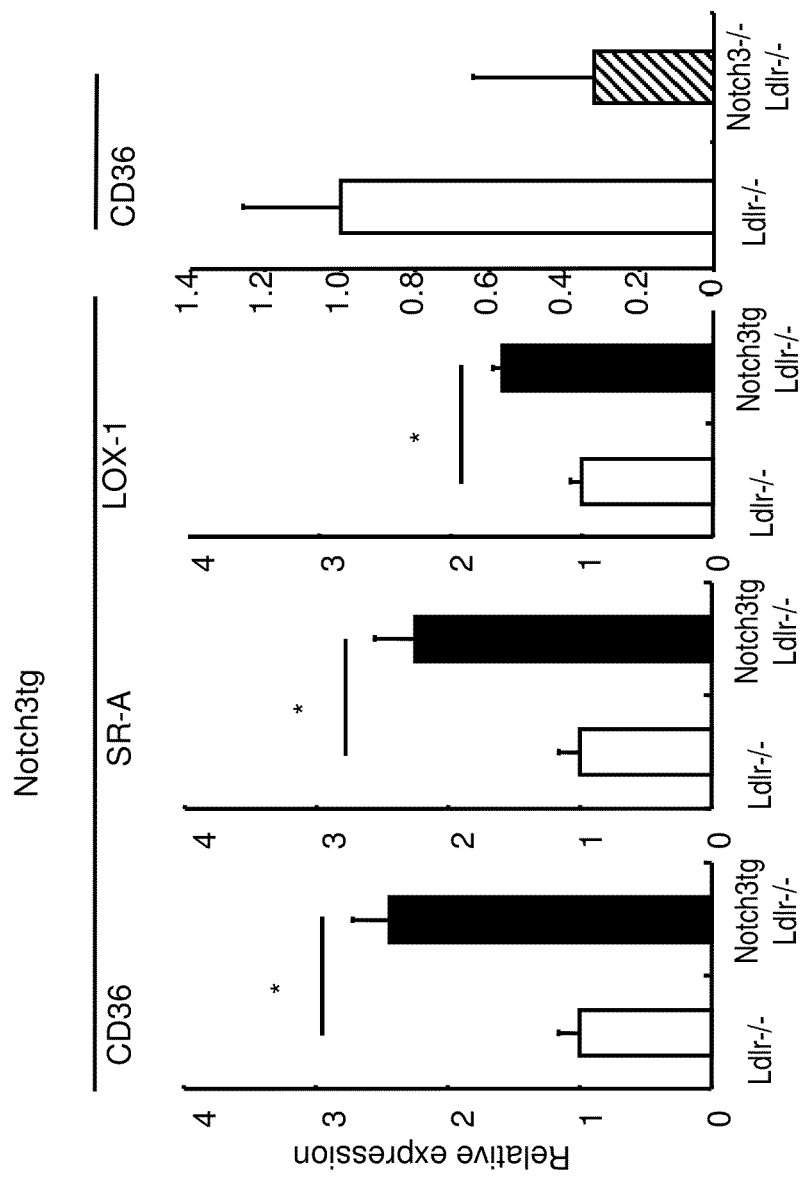
FIG. 26 depicts increased expression of CD36, SR-A and lectin-like oxidized LDL receptor-1 (LOX-1) mRNA in macrophages isolated from cholesterol-fed Notch3tg:Ldlr−/− mice, while CD36 mRNA expression was lower in Notch3−/− mouse macrophages.
Figure 27:
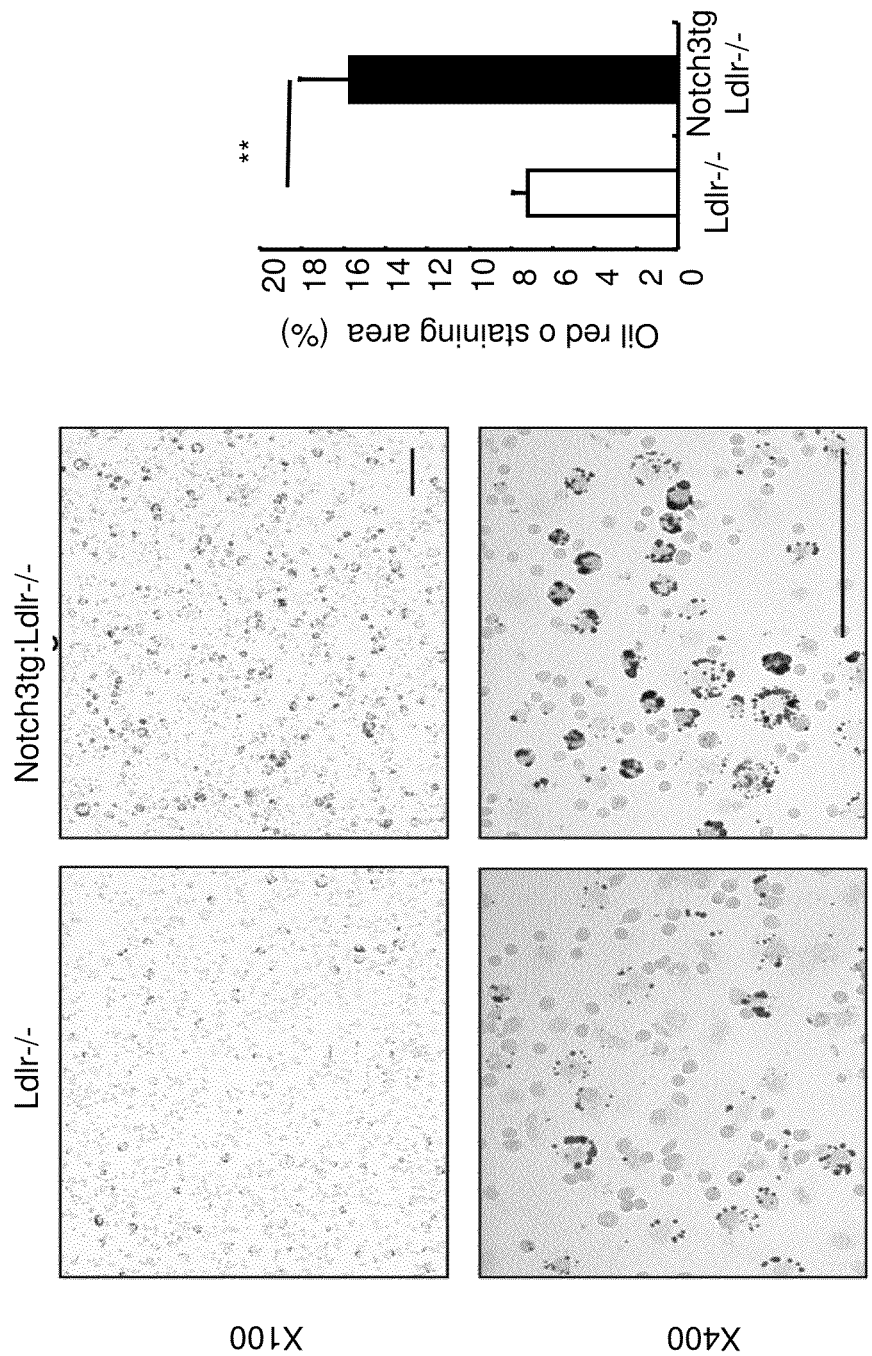
FIG. 27 depicts greater lipid accumulation in peritoneal macrophages isolated from cholesterol-fed Notch3tg:Ldlr$^{-/-}$ mice as compared to those from Ldlr$^{-/-}$ mice, suggesting that NotchICD promotes foam cell formation.

Excessive accumulation of lipids in macrophages via action of scavenger receptors ("foam cell formation") also represents atherogenic functions of these proinflammatory phagocytes. Peritoneal macrophages of Notch3tg mice tend to express higher levels of the major scavenger receptors, CD36 and SR-A. Macrophages isolated from cholesterol-fed Notch3tg:Ldlr−/− mice showed higher mRNA expression of CD36, SR-A and lectin-like oxidized LDL receptor-1 (LOX-1) than those from Ldlr$^{-/-}$ littermates (FIG. 26). Macrophages of Notch3tg−:Ldlr−/− also produced higher protein levels of CD36. In contrast, Notch3 deficiency tended to decrease CD36 mRNA expression in peritoneal macrophages of Ldlr−/− mice (FIG. 26), suggesting that Notch3 signaling in macrophages directly or indirectly regulates scavenger receptor expression. Consistent with increased expression of scavenger receptors, peritoneal macrophages isolated from cholesterol-fed Notch3tg:Ldlr$^{-/-}$ mice showed greater lipid accumulation compared to those from Ldlr−/− littermates (FIG. 27).

Figure 28A:
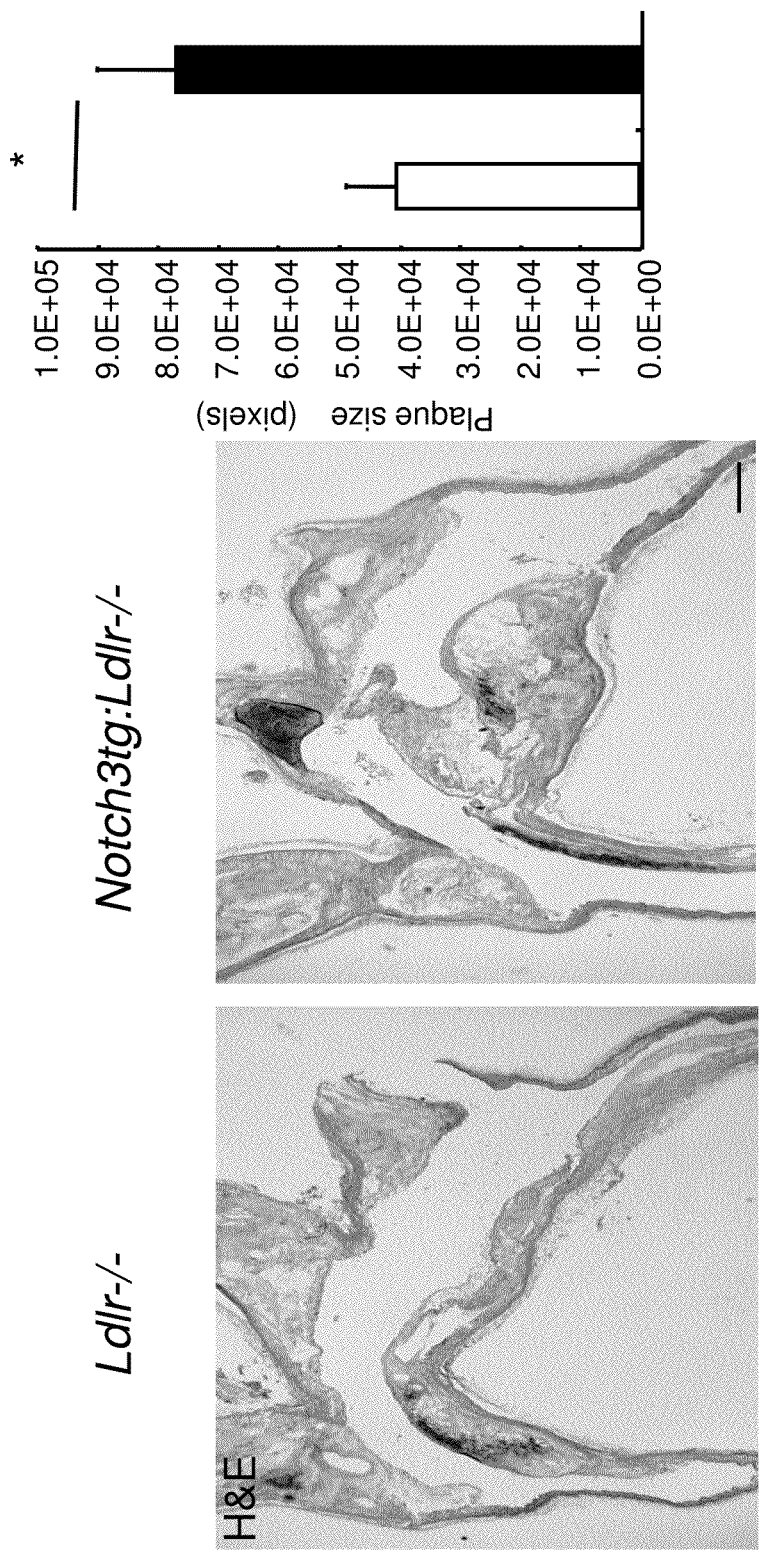
FIGS. 28A-C depict atherosclerotic plaque size, lipid accumulation, and macrophage content in the aorta of cholesterol-fed Notch3tg:Ldlr$^{-/-}$ and Ldl−/− mice, indicating that Notch3ICD accelerated these key features of atherosclerosis. Notably, there were no appreciable differences in the lipid profiles of these two groups.
Figure 28B:
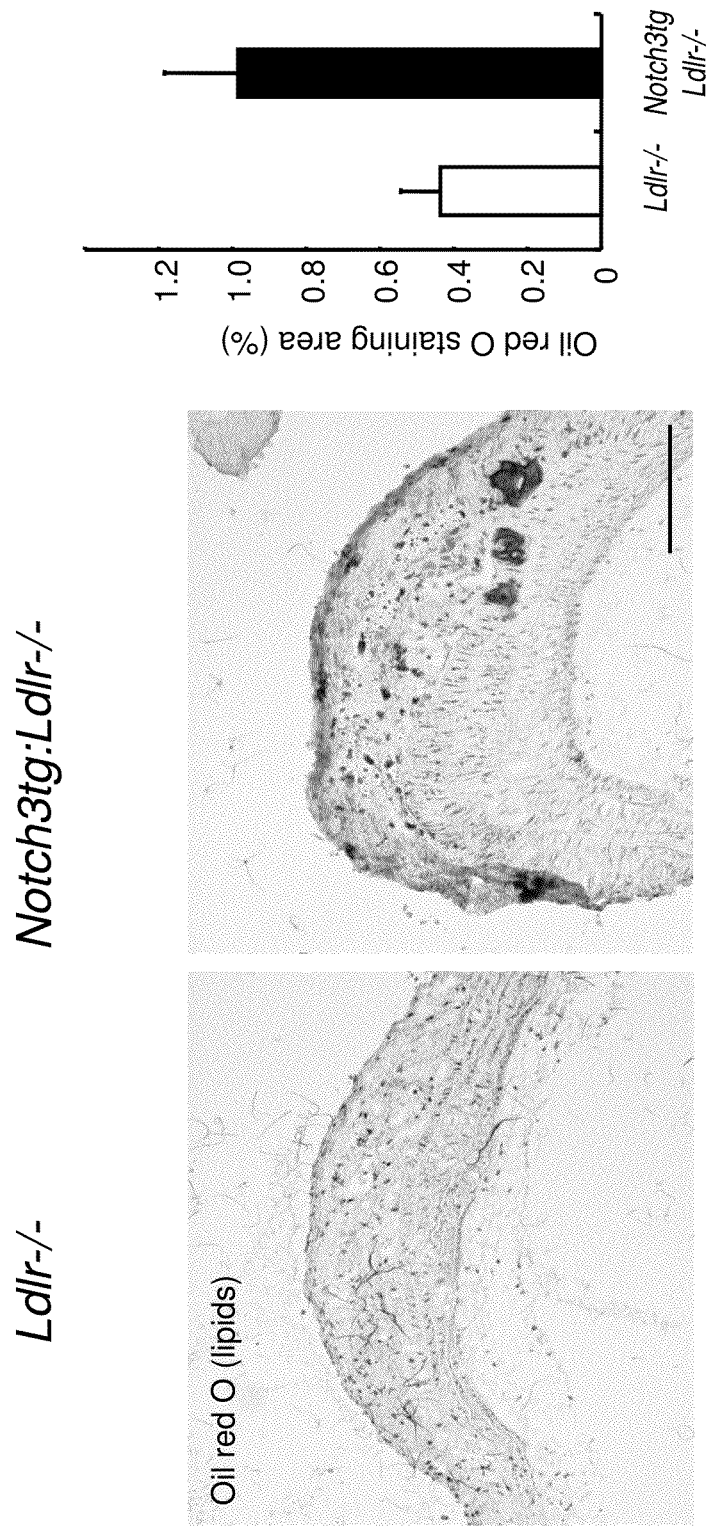
Figure 28C:
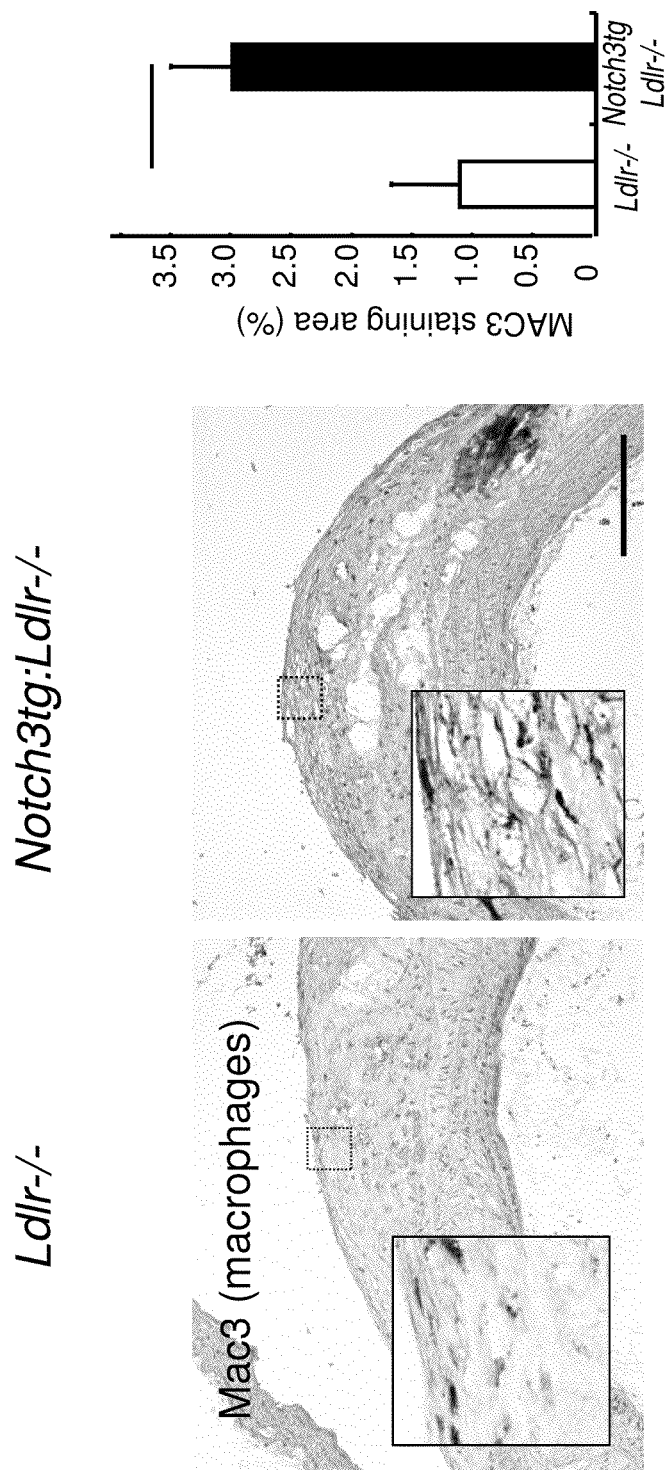

Atherosclerotic Plaques of Macrophage Selective Notch3Tg Mice were Larger and Contained More Macrophages After 24 weeks on a high fat and high cholesterol diet, total cholesterol (798±75 vs. 789±60 mg/dL) and triglyceride (264±35 vs. 270±36 mg/dL) levels did not differ in Notch3: Ldlr−/− mice and Ldlr−/− littermates. Food intake was also similar in the two groups (2.7±0.4 vs. 2.6±0.3 g/day) during the study period. Enforced expression of Notch3-ICD in macrophages significantly increased atherosclerotic plaque size in cholesterol-fed Ldl−/− mice (FIG. 28A). Atherosclerotic plaques of Notch3tg;Ldl−/− mice showed increased lipid accumulation (oil red O), as compared to Ldlr−/− littermates, in agreement with in vitro data (FIG. 28B). In addition, the aorta of Notch3tg:/Ldlr−/− mice contained more macrophages (Mac3 positive area) in the plaque (FIG. 28C).

Figure 29:
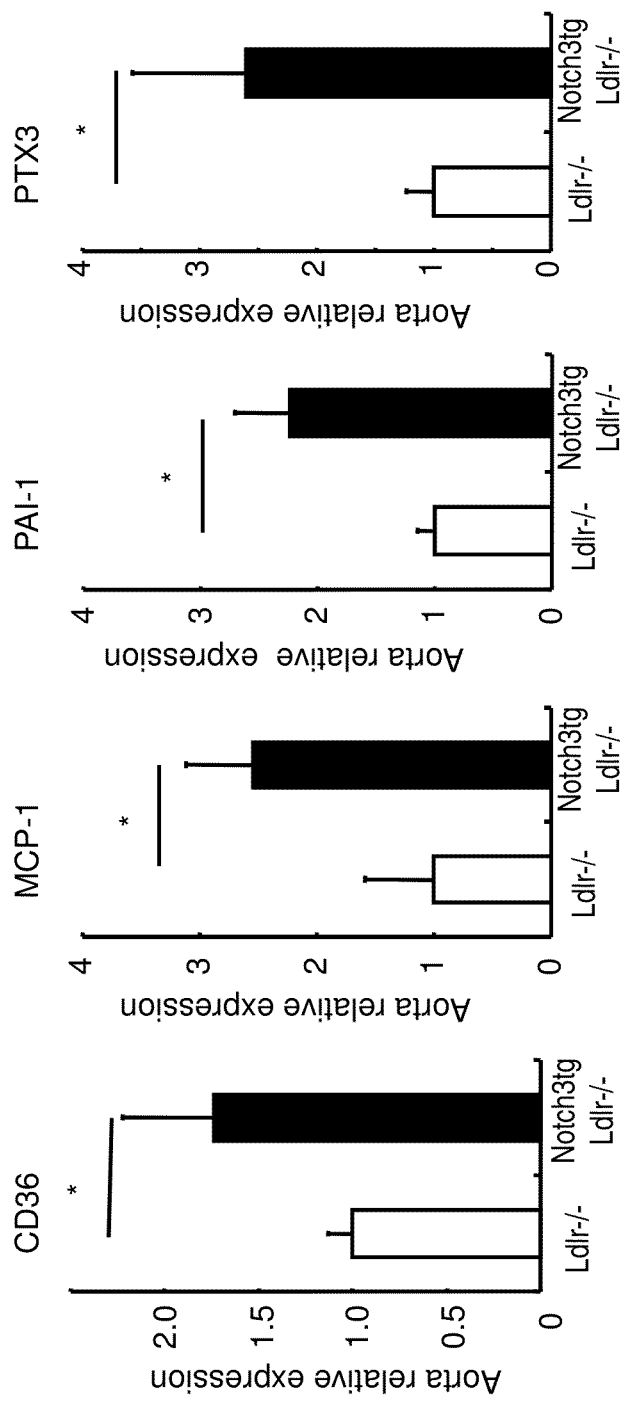
FIG. 29 depicts higher expression levels of CD36, monocyte chemotactic protein-1 (MCP-1), plasminogen activator inhibitor-1 (PAI-1) and the long pantraxin PTX3 mRNA in the aorta of Notch3tg:Ldlr$^{-/-}$ mice.

Furthermore, Notch3tg:Ldlr−/− mice expressed higher levels of CD36, monocyte chemotactic protein-1 (MCP-1), plasminogen activator inhibitor-1 (PAI-1) and the long pantraxin PTX3 (FIG. 29). There was no significant difference of plaque size in cholesterol-fed Notch3−/−:Ldlr−/− mice and Ldlr−/− littermates did not differ significantly (47529±8607 vs. 40290±4474 pixels).

Figure 30A:
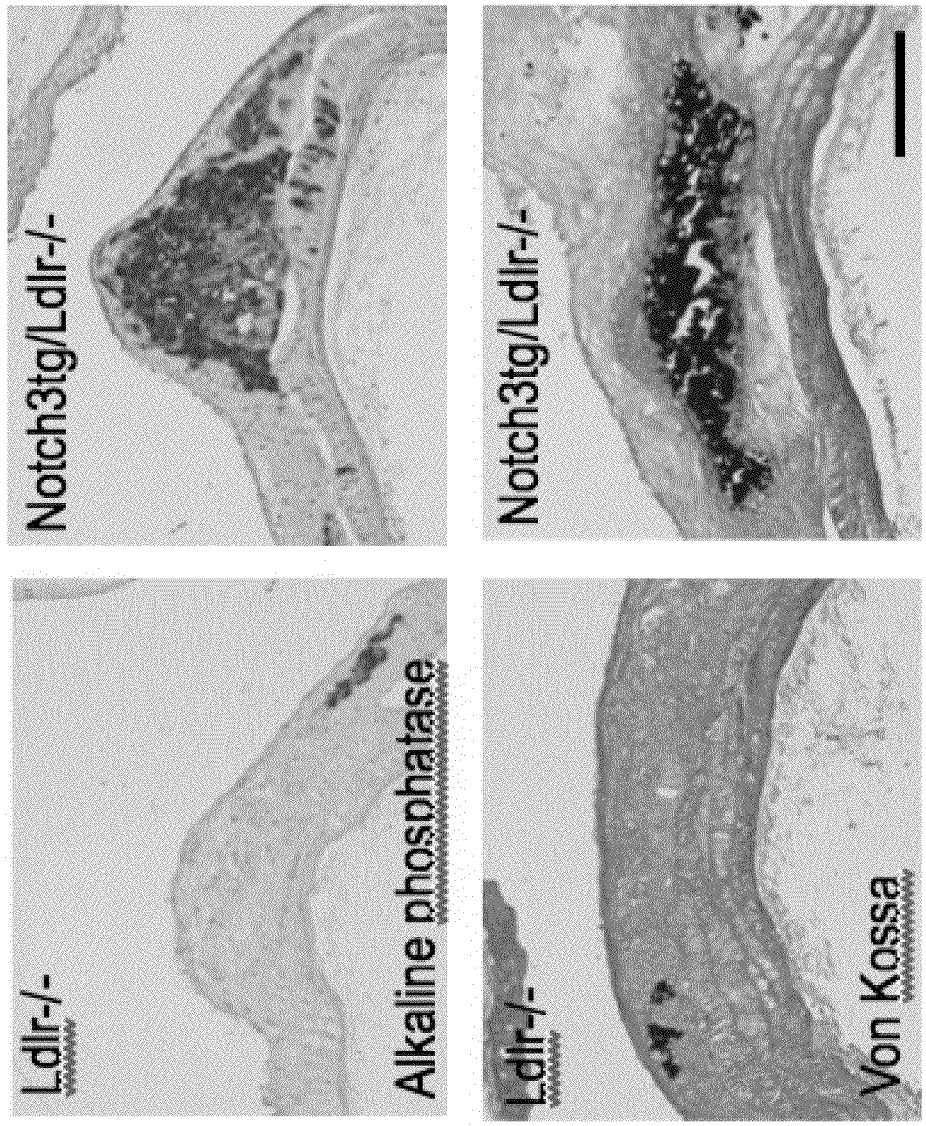
FIGS. 30A-B depict the aorta of macrophage-selective Notch3tg/Ldlr−/− mice after 24 weeks on high-fat and high-cholesterol diet showed greater osteogenic activity (alkaline phosphatase activity) and calcium deposit (von Kossa) compared to Ldlr−/− littermates.
Figure 30B:
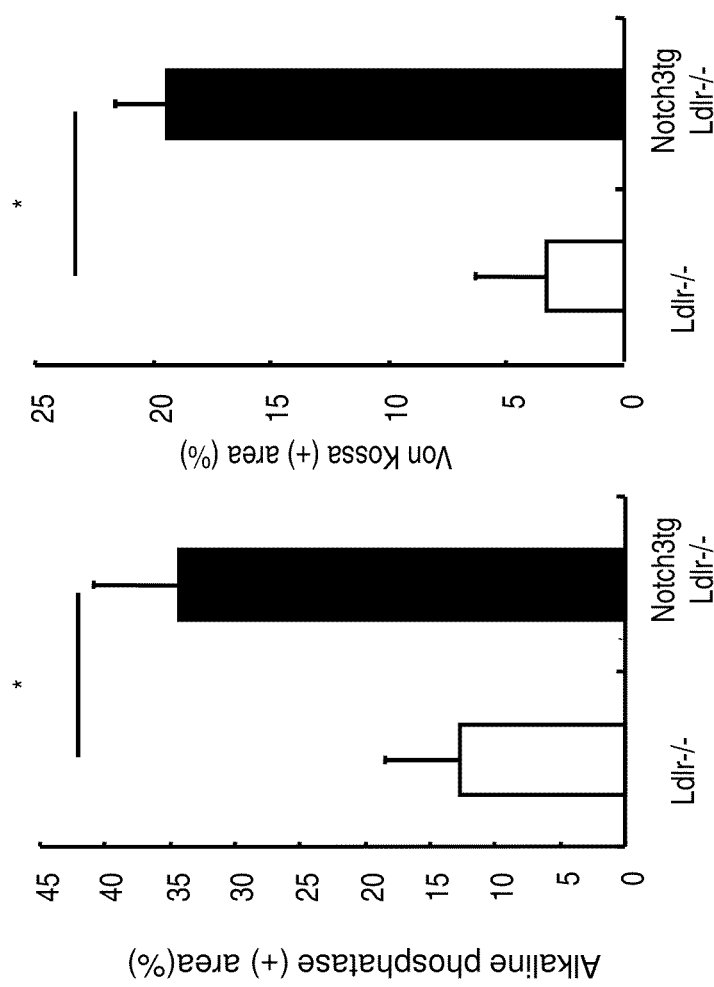
Figure 31:
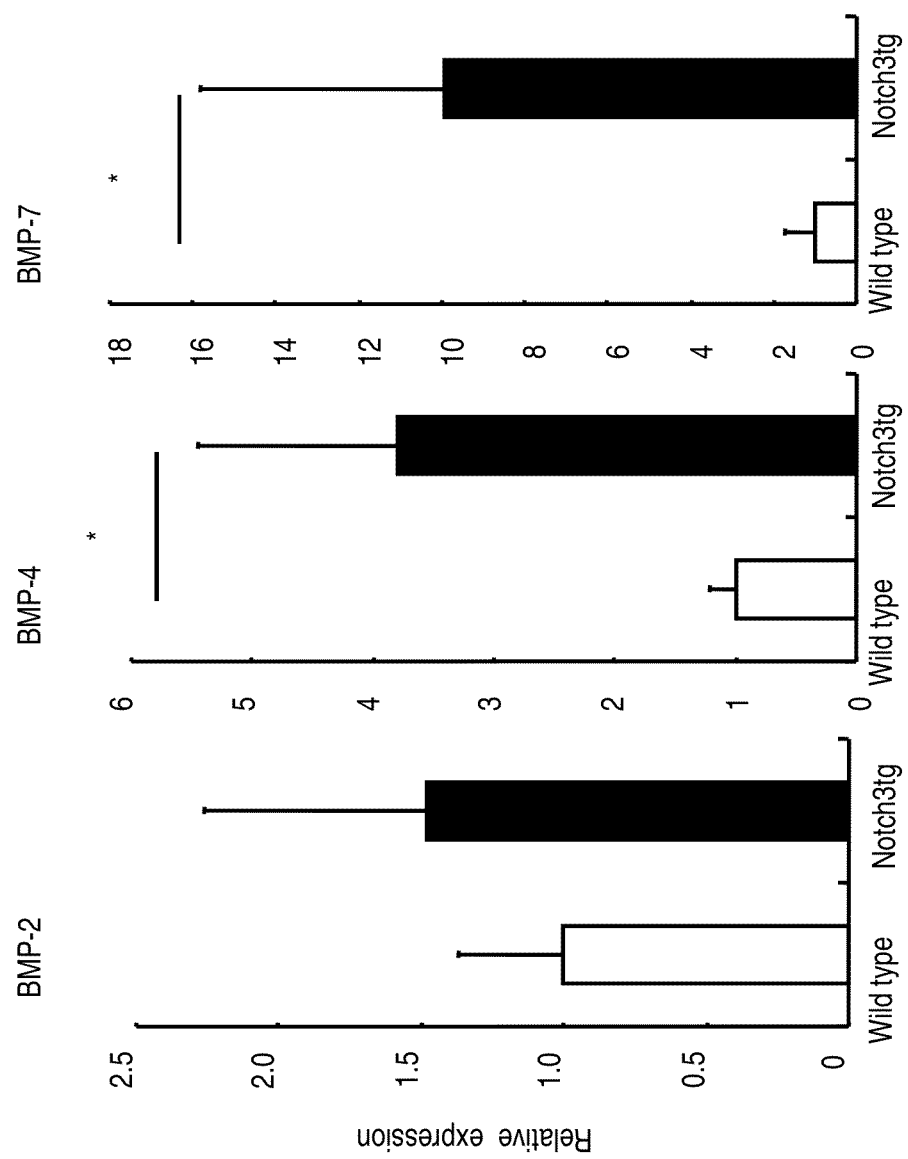
FIG. 31 depicts Notch3tg peritoneal macrophages expressing higher levels of BMP-4 and -7 mRNA, inducers of osteoblast differentiation, than those from littermate controls.

Macrophage Selective Expression of Notch3-ICD-Promoted Aortic Calcification in Ldlr−/− Mice The aorta of macrophage-selective Notch3tg/Ldlr−/− mice after 24 weeks on high fat and high cholesterol diet showed greater osteogenic activity (alkaline phosphatase activity) and calcium deposit (von Kossa) compared to Ldlr−/− littermates (FIGS. 30A-B). Notch3tg peritoneal macrophages expressed higher levels of BMP-4 and -7 mRNA, inducers of osteoblast differentiation, than those from littermate controls, providing a possible mechanism of accelerated aortic calcification (FIG. 31). In contrast, peritoneal macrophages from Notch3−/−:Ldlr−/− mice tended to decrease BMP-4 mRNA expression. In addition, BMP-7 mRNA levels in the aorta of Notch3tg:Ldlr−/− mice significantly increased after 24-week high fat and high cholesterol diet. Alkaline phosphatase stained area (10.2±3.5 vs. 10.4±3.1%) and calcified area (6.4±2.2 vs. 5.7±1.9%) in the plaque did not differ in Notch3−/−:Ldlr−/− mice and Ldlr−/− littermates.

Macrophage Selective Notch3 Activation Promoted Visceral Obesity

Figure 32:
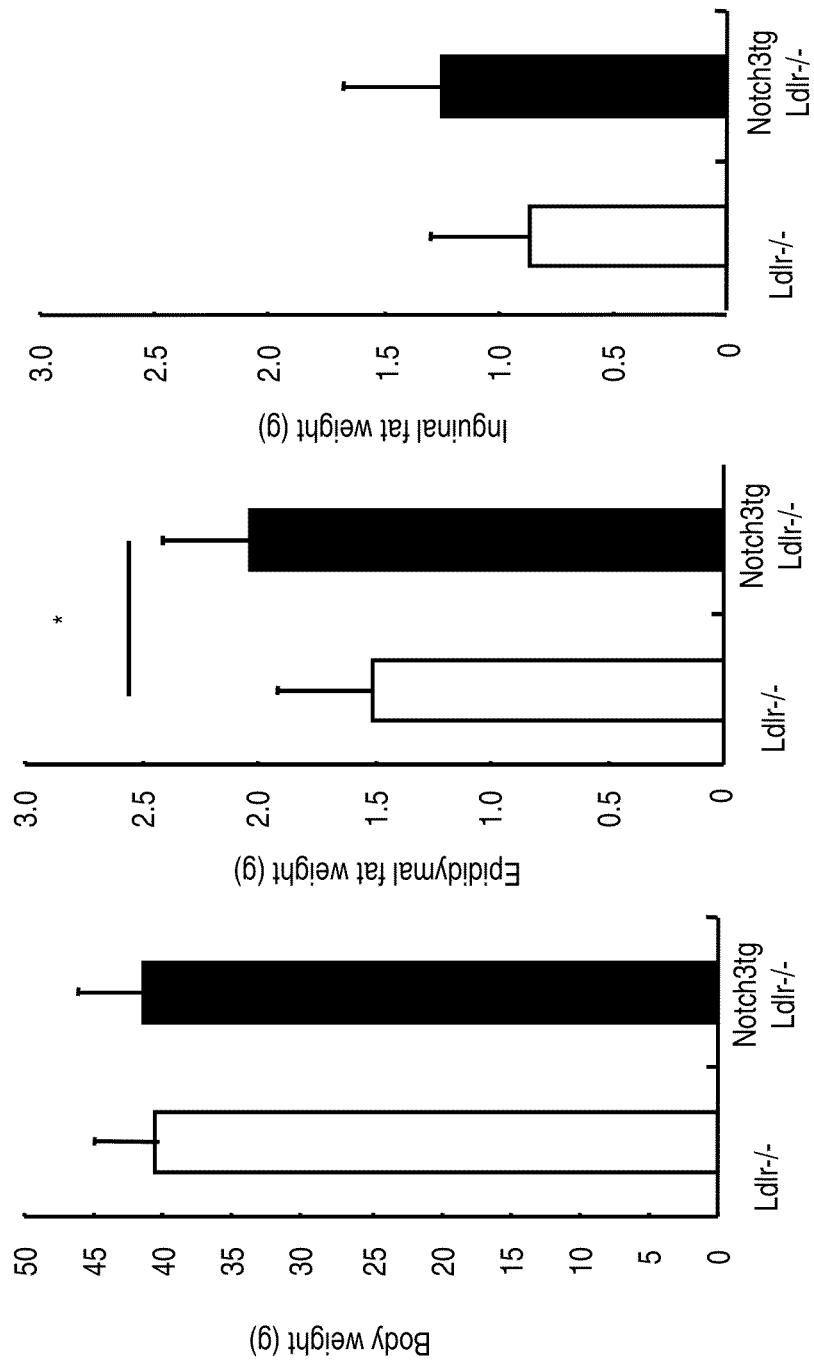
FIG. 32 depicts epididymal and inguinal fat weight in Notch3tg/Ldlr−/− mice and Ldlr−/− littermates after 24 weeks on high fat and high cholesterol diet.
Figure 33:
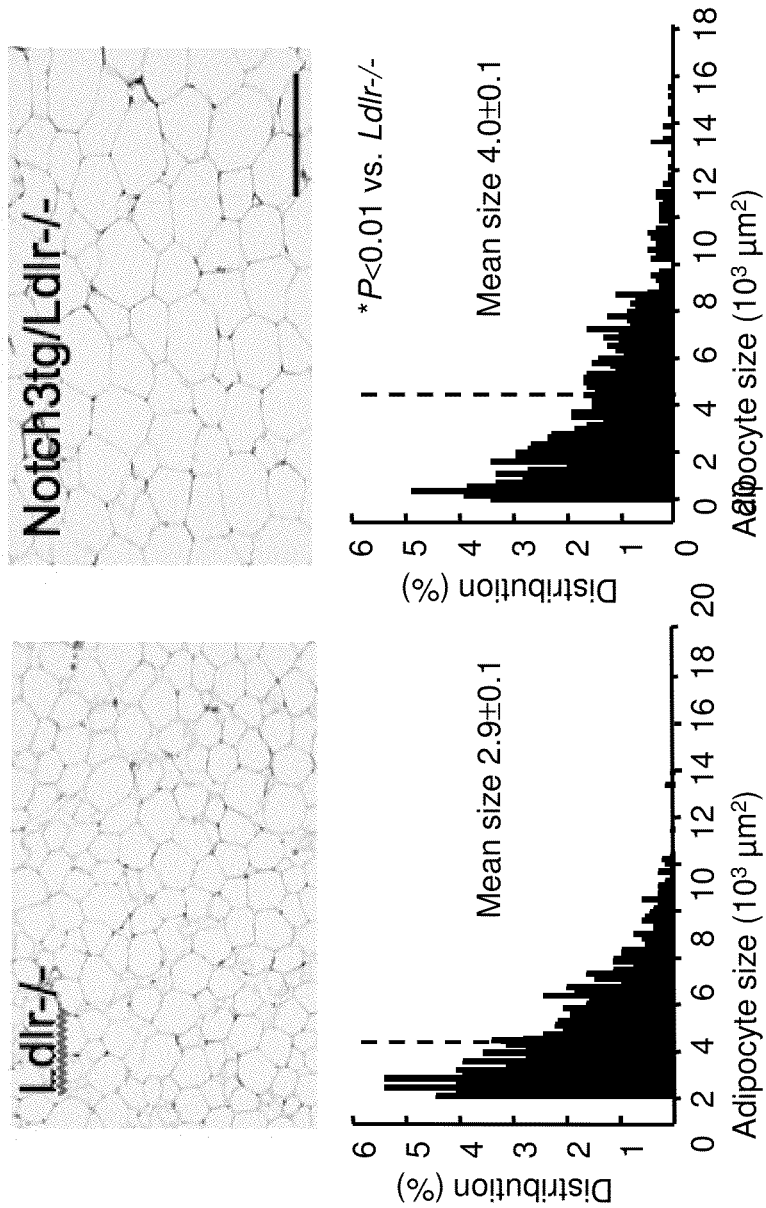
FIG. 33 depicts Notch3tg:Ldlr−/− mice having larger adipocytes size in epididymal fat than Ldlr−/− littermates.
Figure 34:
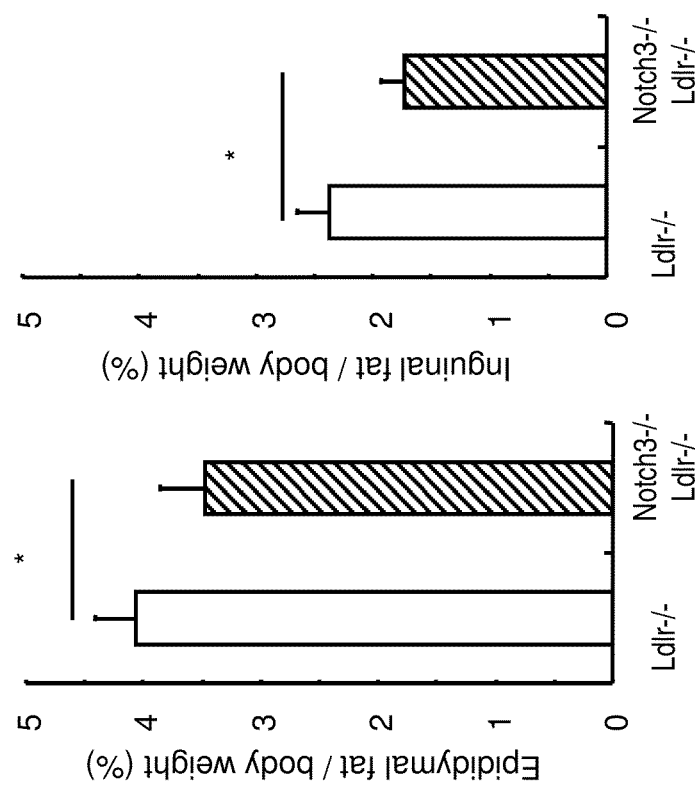
FIG. 34 depicts cholesterol-fed Notch3−/−:Ldlr−/− mice showing the lower ratio of epididymal and inguinal fat weight to total body weight than Ldlr−/− littermates.

While accumulating evidence has associated macrophages with obesity, a causal role of these proinflammatory phagocytes remains to be established. To provide a mechanistic link between macrophage activation and adiposity, Applicants further tested the hypothesis in vivo that Notch-triggered macrophage activation promotes obesity using macrophage-selective Notch3tg mice crossed with Ldlr−/−, a commonly used model of metabolic disorders. Epididymal and inguinal fat weight was significantly greater in Notch3tg/Ldlr−/− mice as compared with Ldlr−/− littermates after 24 weeks on high fat and high cholesterol diet while total body weights did not differ between two groups (FIG. 32). The ratio of epididymal and inguinal fat weight to body weight also increased in Notch3tg:Ldlr−/− mice compared with Ldlr−/− mice (3.04±0.32 vs. 2.05±0.27 g and, 5.00±0.16 vs. 3.67±0.26, respectively). Dual energy X-ray absorptiometry also showed increased fat mass in Notch3tg:Ldlr−/− mice. Furthermore, Notch3tg:Ldlr−/− mice had larger adipocytes size in epididymal fat than Ldlr−/− littermates (FIG. 33). In contrast, cholesterol-fed Notch3−/−:Ldlr−/− mice showed the lower ratio of epididymal and inguinal fat weight to total body weight than Ldlr−/− littermates (FIG. 34). These results from gain-of-function and loss-of-function studies suggest that Notch3 activation in macrophages affects neighboring adipocytes and promotes visceral adipocity.

Figure 35:
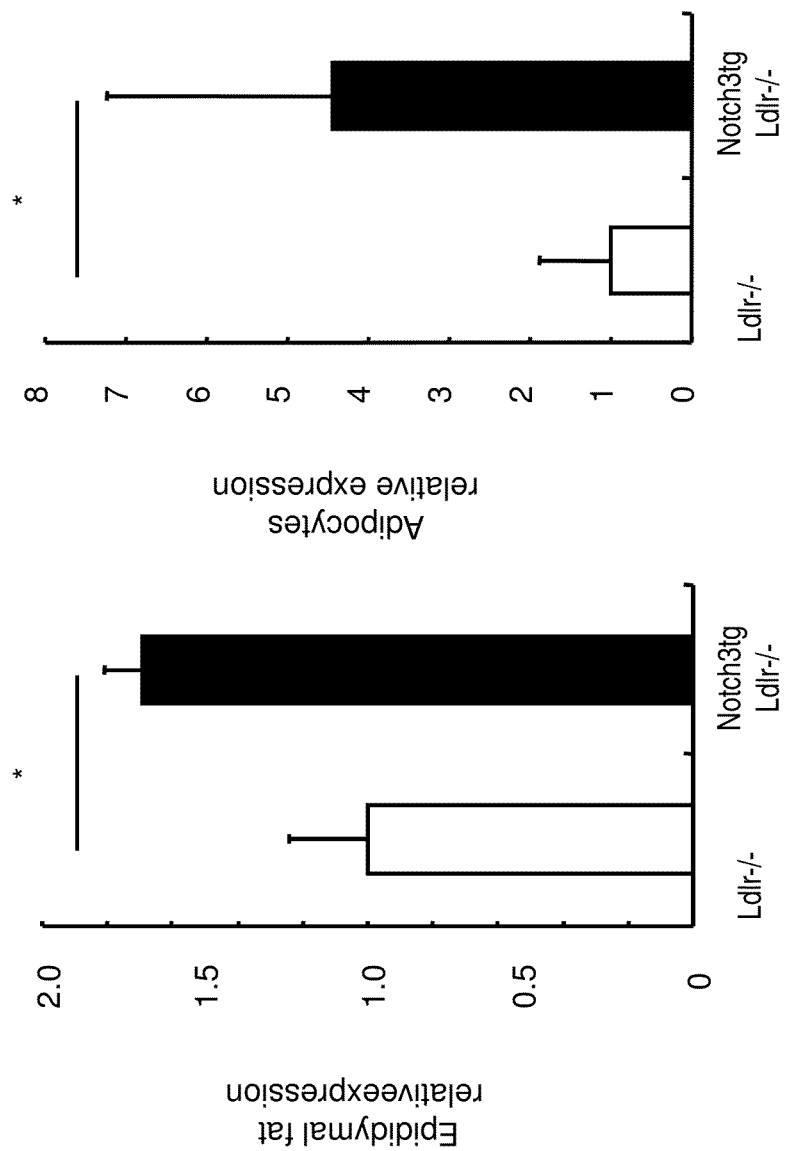
FIG. 35 depicts epididymal fat tissue and adipocytes of Notch3tg:Ldlr−/− mice expressing mRNA levels of leptin.

Applicants further found that visceral fat tissue of Notch3tg:Ldlr−/− mice expressed higher mRNA levels of leptin, an important adipose-derived hormone associated with obesity, than Ldlr−/− littermates (FIG. 35). Isolated adipocytes from Notch3tg:Ldlr−/− mice also showed increased leptin mRNA expression (FIG. 35). Consistent with these results, Notch3tg:Ldlr−/− mice showed higher serum leptin levels while Notch3−/−:Ldlr−/− mice had lower levels. In addition, Notch3tg:Ldlr−/− mice tended to increase mRNA expression of several other molecules associated with monocyte/macrophage recruitment into the tissue, atherogenesis, thrombosis, and innate immunity (e.g., MCP-1, PAI-1 and PTX3) in epididymal fat, while adiponectin and TNF-α a mRNA levels did not differ between both groups. Furthermore, mRNA expression of hormone sensitive lipase (HSL), a key enzyme of lipolysis in fat tissue, was lower in epididymal fat of Notch3tg:Ldlr−/− mice than that of Ldlr−/− mice, whereas adipose triglyceride lipase (ATGL), an initiator of lipolysis in fat tissue, did not differ between 2 groups.

Figure 36:
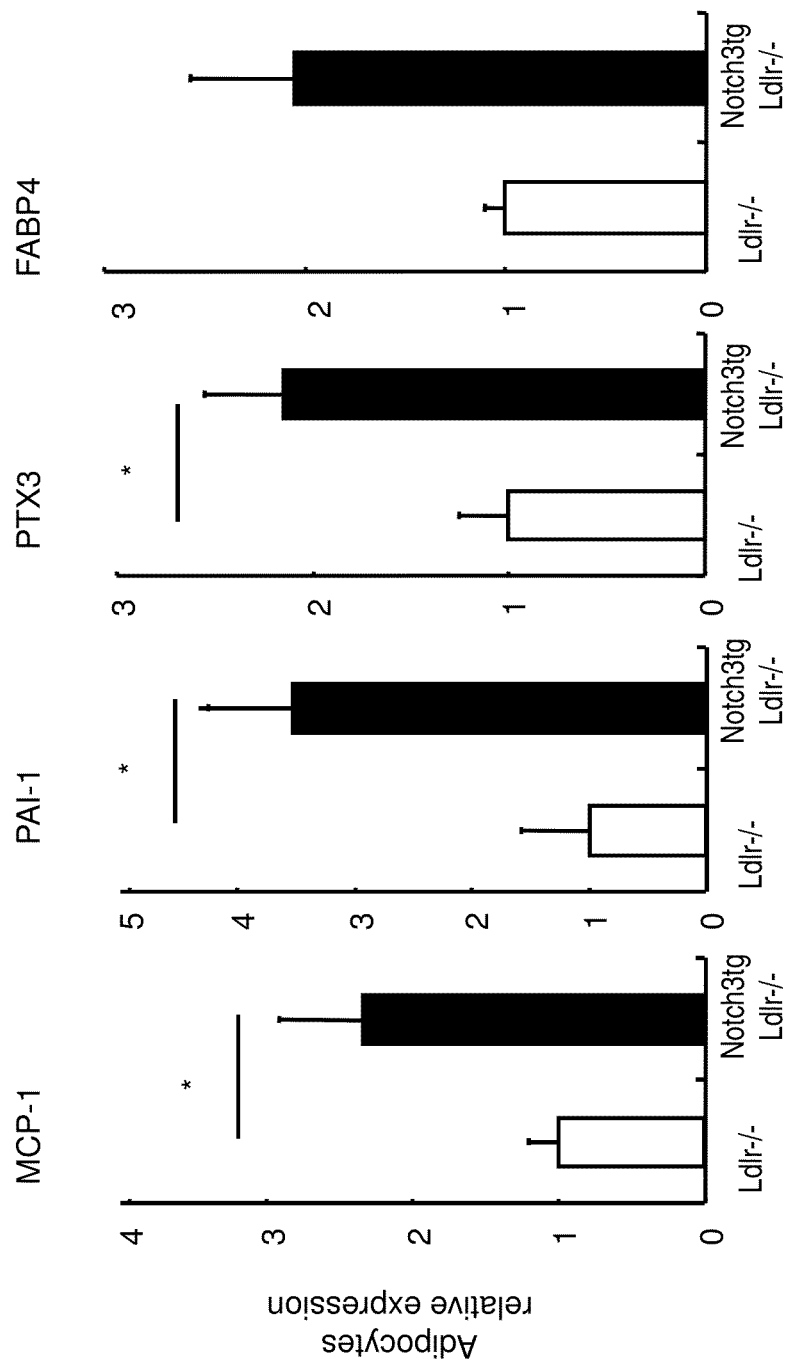
FIG. 36 depicts increased mRNA expression of MCP-1, PAI-1, PTX3 and adipocyte-specific fatty acid-binding protein 4 (FABP4, also known as Ap2) in Notch3tg adipocytes.

To further examine the role of adipocytes in these changes, Applicants isolated adipocytes from epididymal fat of Notch3tg:Ldlr−/− mice. Adipocytes derived from Notch3tg:Ldlr−/− mice had higher expression of MCP-1, PAI-1 and PTX3 (FIG. 36). Notch3tg adipocytes also tended to increase adipocyte-specific fatty acid-binding protein 4 (FABP4, also known as Ap2) expression, a marker of adipocyte differentiation (FIG. 36). These results further indicate that Notch3 activation in macrophages modulates adipocyte function toward development of obesity.

Figure 37A:
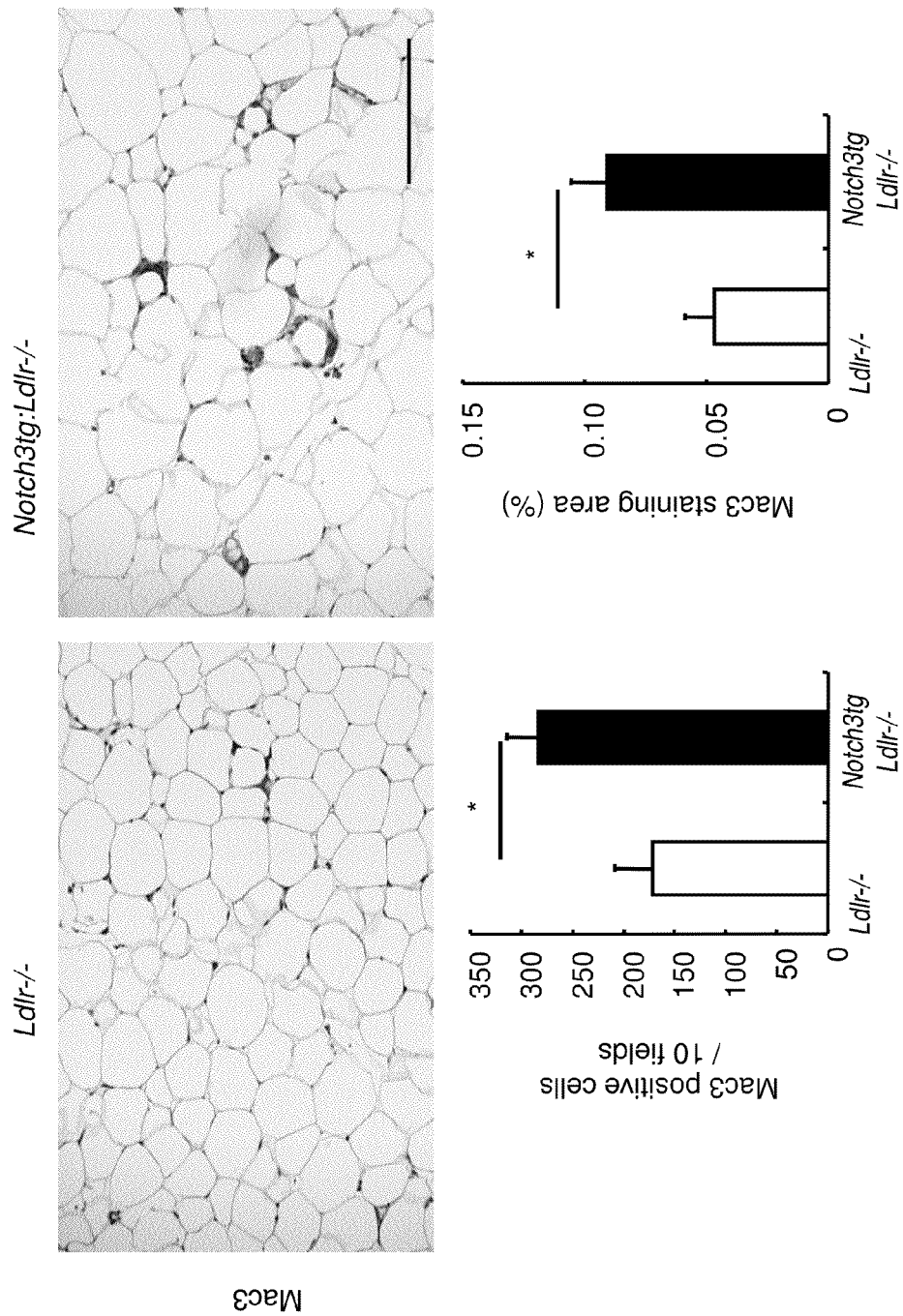
FIGS. 37A-B depicts Mac3 immunopositive cell number and area, and expression of F4/80 mRNA in epididymal fat from Notch3tg:Ldlr−/− and Ldlr−/− mice, indicating that NotchICD increased macrophage accumulation in fat.
Figure 37B:
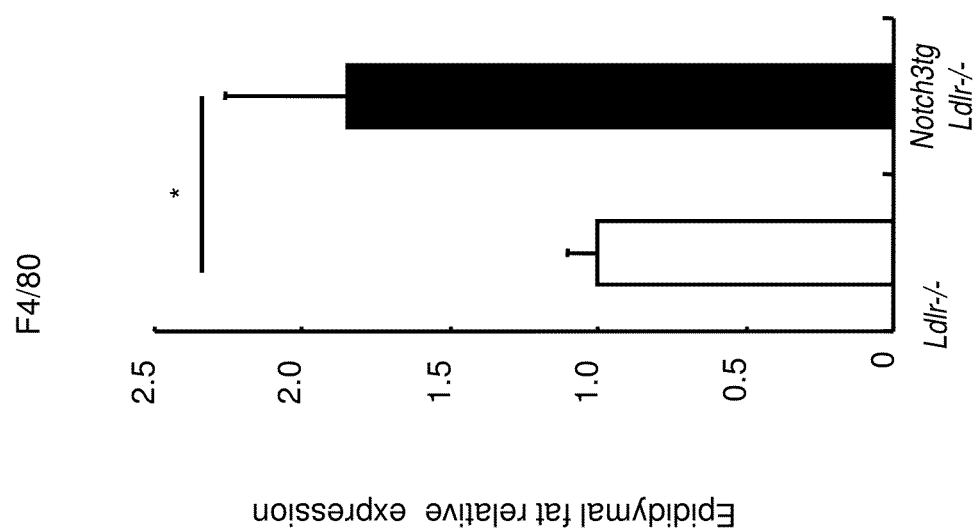

Macrophage Selective Expression of Notch3-ICD Mice Induced Macrophage Accumulation in Visceral Fat Epididymal fat tissue from Notch3tg:Ldlr−/− mice contains more macrophages than those from Ldlr−/− littermates as gauged by Mac3 immunopositive area and expression of F4/80 mRNA (FIGS. 37A-B). These data suggest that Notch3 activation in macrophages induces inflammatory burden in visceral fat tissue.

C. Discussion

The present study used macrophage selective transgenic mice expressing Notch3-ICD, a constitutively active form, to test two biological and mechanistic hypotheses: 1) Notch signaling promotes macrophage activation in vivo; and 2) Notch-triggered macrophage activation accelerates progression of atherosclerosis and obesity. The results suggest that Notch3 activation in macrophages modulates function of these phagocytes as well as neighboring adipocytes toward development of cardiometabolic disorders.

The invention is further described by the following numbered paragraphs:

1. A method of treating or preventing obesity in a patient, comprising administering to said patient a therapeutically effective amount of a compound that inhibits the NOTCH signaling pathway.
2. The method of paragraph 1, wherein said patient has a body mass index (BMI) of 30 kg/m$^2$ or higher.
3. The method of paragraph 1, wherein said compound is a gamma-secretase inhibitor.
4. The method of paragraph 1, wherein said compound inhibits said NOTCH signaling pathway by a biological process selected from the group consisting of: blocking the binding of a ligand to a Notch receptor; blocking expression, function, or activity of any NOTCH pathway component; interfering with Notch receptor trafficking or cleavage; enhancing expression, function, or activity of any NOTCH pathway component; and blocking the cleavage or endocytosis of a Notch ligand.
5. The method of paragraph 4, wherein said Notch receptor is of the NOTCH-1 receptor subtype, the NOTCH-2 receptor subtype, the NOTCH-3 receptor subtype or the NOTCH-4 receptor subtype.
9. The method of paragraph 1, wherein said compound is an RNA interfering agent, a blocking antibody, a small molecule, a peptide, a biosimilar, or a DNA plasmid.
10. A method of determining whether, relative to a control group, a subject that is not obese is at increased risk of becoming obese in the future, comprising:
a) assaying a test biological sample derived from said subject or an imaging biomarker for the amount, function, or activity of a NOTCH component that is present;
b) comparing the results obtained in step a with those from one or more samples or imaging data from said control group; and
c) concluding that said subject is at increased risk of becoming obese if the level of the amount, function, or activity of said NOTCH component is higher in said test biological sample than in that of said samples from said control group.
11. The method of paragraph 10, wherein said Notch component is a NOTCH receptor, a NOTCH ligand selected from the group consisting of: Delta1 (or Delta-like 1/Dll1), Delta3 (Delta-like 3/Dll3), Delta4 (Delta-like 4/Dll4), Jagged1, and Jagged2, ADAM family proteinases, a gamma-secretase component, MAML1-3, or RBP-Jkappa.
12. The method of either paragraph 10 or paragraph 11, wherein said biological sample is a sample of blood, plasma, serum, urine, tissue or cells.
13. A method of treating or preventing metabolic syndrome in a patient, comprising administering to said patient a therapeutically effective amount of a compound that inhibits the NOTCH signaling pathway.
14. The method of paragraph 13, wherein said patient has 3 or more of the following: waist circumference ≥40 inches in men, ≥35 inches in women; blood pressure ≥130/85 mmHg; triglycerides ≥150 mg/dL; HDL cholesterol ≤40 mg/dL in men, 50 mg/dL in women; and glucose ≥100 mg/dL.
15. The method of paragraph 13, wherein said compound is a gamma-secretase inhibitor.
16. The method of paragraph 13, wherein said compound inhibits said NOTCH signaling pathway by a biological process selected from the group consisting of: blocking the binding of a ligand to a Notch receptor; blocking expression, function, or activity of any NOTCH pathway component; interfering with Notch receptor trafficking or cleavage; enhancing expression, function, or activity of any NOTCH pathway component; and blocking the cleavage or endocytosis of a Notch ligand.
17. The method of paragraph 16, wherein said Notch receptor is of the NOTCH-1 receptor subtype.

18. The method of paragraph 16, wherein said Notch receptor is of the NOTCH-2 receptor subtype.
19. The method of paragraph 16, wherein said Notch receptor is of the NOTCH-3 receptor subtype.
20. The method of paragraph 16, wherein said Notch receptor is of the NOTCH-4 receptor subtype.
21. The method of paragraph 13, wherein said compound is an RNA interfering agent, a blocking antibody, a small molecule, a peptide, a biosimilar, or a DNA plasmid.
22. A method of determining whether, relative to a control group, a subject that does not have metabolic syndrome is at increased risk of developing metabolic syndrome in the future, comprising:
a) assaying a test biological sample derived from said subject or an imaging biomarker for the amount, function, or activity of a NOTCH component that is present;
b) comparing the results obtained in step a with those from one or more samples or imaging data from said control group; and
c) concluding that said subject is at increased risk of becoming obese if the level of the amount, function, or activity of said NOTCH component is higher in said test biological sample than in that of said samples from said control group.
23. The method of paragraph 22, wherein said Notch component is a NOTCH receptor, a NOTCH ligand selected from the group consisting of: Delta1 (or Delta-like 1/Dll1), Delta3 (Delta-like 3/Dll3), Delta4 (Delta-like 4/Dll4), Jagged1, and Jagged2, ADAM family proteinases, a gamma-secretase component, MAML1-3, or RBP-Jkappa.
24. The method of either paragraph 22 or paragraph 23, wherein said biological sample is a sample of blood, plasma, serum, urine, tissue or cells.
25. A method of treating or preventing complications of metabolic disorders in a patient, comprising administering to said patient a therapeutically effective amount of a compound that inhibits the NOTCH signaling pathway.
26. The method of paragraph 25, wherein said complications of metabolic disorders are selected from the group consisting of: cancer; chronic kidney disease; nonalcoholic fatty liver disease; pancreatitis; atherosclerosis; arterial or valvular inflammation; arterial or valvular calcification; vasculitis; retinopathy; erectile dysfunction; heart failure; neuroinflammation; cognitive impairment; accelerated tissue injury or delayed healing after acute myocardial infarction, stroke, vein graft implantation, heart transplantation, coronary intervention, stent implantation, implantation of engineered tissues, implantation of allograft, homograft, or bioprosthesis tissues, implantation of Dacron grafts or any synthetic or biosprothetic conduits.
27. The method of paragraph 26, wherein said compound is a gamma-secretase inhibitor.
28. The method of paragraph 27, wherein said compound inhibits said NOTCH signaling pathway by a biological process selected from the group consisting of: blocking the binding of a ligand to a Notch receptor; blocking expression, function, or activity of any NOTCH pathway component; interfering with Notch receptor trafficking or cleavage; enhancing expression, function, or activity of any NOTCH pathway component; and blocking the cleavage or endocytosis of a Notch ligand.
29. The method of paragraph 28, wherein said Notch receptor is of the NOTCH-1 receptor subtype.
30. The method of paragraph 4, wherein said Notch receptor is of the NOTCH-2 receptor subtype.
31. The method of paragraph 4, wherein said Notch receptor is of the NOTCH-3 receptor subtype.
32. The method of paragraph 4, wherein said Notch receptor is of the NOTCH-4 receptor subtype.
33. The method of paragraph 25, wherein said compound is an RNA interfering agent, a blocking antibody, a small molecule, a peptide, a biosimilar, or a DNA plasmid.
34. A method of determining whether, relative to a control group, a subject that does not have clinically apparent complications of metabolic disorders is at increased risk of developing these complications in the future, comprising:
a) assaying a test biological sample derived from said subject or an imaging biomarker for the amount, function, or activity of a NOTCH component that is present;
b) comparing the results obtained in step a with those from one or more samples, or imaging data from said control group; and
c) concluding that said subject is at increased risk of becoming having complications associated with metabolic disorders if the level of the amount, function, or activity of said NOTCH component is higher in said test biological sample than in that of said samples from said control group.
35. The method of paragraph 34, wherein said Notch component is a NOTCH receptor, a NOTCH ligand selected from the group consisting of, but not limited to: Delta1 (or Delta-like 1/Dll1), Delta3 (Delta-like 3/Dll3), Delta4 (Delta-like 4/Dll4), Jagged1, and Jagged2, ADAM family proteinases, a gamma-secretase component, MAML1-3, or RBP-Jkappa.
36. The method of either paragraph 34 or paragraph 35, wherein said biological sample is a sample of blood, plasma, serum, urine, tissue or cells.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of treating a patient for metabolic syndrome comprising administering to said patient a therapeutically effective amount of an antibody that binds to Delta-like 4 (DLL4) and inhibits the NOTCH signaling pathway.

2. The method of claim 1, wherein said patient is treated for a sufficient period of time to reduce or eliminate one or more symptoms associated with metabolic syndrome, wherein said symptoms are selected from the group consisting of: a waist circumference ≥40 inches in men or ≥35 inches in women; blood pressure ≥130/85 mmHg; triglycerides ≥150 mg/dL; HDL cholesterol ≤40 mg/dL in men and 50 mg/dL in women; and glucose ≥100 mg/dL.

3. The method of claim 2, wherein said patient is treated for a sufficient period of time to reduce or eliminate more than one of said symptoms.

4. The method of claim 1, wherein said metabolic syndrome is accompanied by one or more complications selected from the group consisting of: atherosclerosis; acute myocardial infarction; chronic kidney disease; arterial calcification; valvular calcification; valvular stenosis; restenosis after coronary intervention; accelerated tissue damage or delayed healing after coronary intervention; failure of vein grafts for coronary bypass surgery; diabetic nephropathy; vasculitis; retinopathy; erectile dysfunction; stroke and heart failure.

5. The method of claim 1, wherein said patient is treated by administering a pharmaceutical composition comprising said antibody and a pharmaceutically acceptable carrier.

6. The method of claim 5, wherein said patient is treated for a sufficient period of time to reduce or eliminate one or more symptoms associated with metabolic syndrome, wherein said symptoms are selected from the group consisting of: a waist circumference >40 inches in men or >35 inches in women; blood pressure >130/85 mmHg; triglycerides >150 mg/dL; HDL cholesterol 40 mg/dL in men and 50 mg/dL in women; and glucose >100 mg/dL.

7. The method of claim 6, wherein said patient is treated for a sufficient period of time to reduce or eliminate more than one of said symptoms.

8. The method of claim 6, wherein said metabolic syndrome is accompanied by one or more complications selected from the group consisting of: acute myocardial infarction; arterial calcification; valvular calcification; valvular stenosis; restenosis after coronary intervention; accelerated tissue damage or delayed healing after coronary intervention; failure of vein grafts for coronary bypass surgery; stroke and heart failure.

9. The method of claim 6, wherein said metabolic syndrome is accompanied by one or more complications selected from the group consisting of: chronic kidney disease; diabetic nephropathy; vasculitis; retinopathy; and erectile dysfunction.

10. The method of claim 5, wherein said pharmaceutical composition is in unit dosage form.

11. The method of claim 10, wherein said patient is treated for a sufficient period of time to reduce or eliminate one or more symptoms associated with metabolic syndrome, wherein said symptoms are selected from the group consisting of: a waist circumference >40 inches in men or >35 inches in women; blood pressure >130/85 mmHg; triglycerides >150 mg/dL; HDL cholesterol 40 mg/dL in men and 50 mg/dL in women; and glucose >100 mg/dL.

12. The method of claim 11, wherein said patient is treated for a sufficient period of time to reduce or eliminate more than one of said symptoms.

13. The method of claim 11, wherein said metabolic syndrome is accompanied by one or more complications selected from the group consisting of: acute myocardial infarction; arterial calcification; valvular calcification; valvular stenosis; restenosis after coronary intervention; accelerated tissue damage or delayed healing after coronary intervention; failure of vein grafts for coronary bypass surgery; stroke and heart failure.

14. The method of claim 11, wherein said metabolic syndrome is accompanied by one or more complications selected from the group consisting of: chronic kidney disease; diabetic nephropathy; vasculitis; retinopathy; and erectile dysfunction.

15. A method of treating a patient for metabolic syndrome comprising administering to said patient a therapeutically effective amount of a compound that inhibits the NOTCH signaling pathway wherein:
   a) said patient is treated for a sufficient period of time to reduce or eliminate one or more symptoms associated with metabolic syndrome, wherein said one or more symptoms are selected from the group consisting of: a waist circumference ≥40 inches in men or ≥35 inches in women; blood pressure ≥130/85 mmHg; triglycerides ≥150 mg/dL; HDL cholesterol ≤40 mg/dL in men and 50 mg/dL in women; and glucose ≥100 mg/dL;
   b) said compound is an antibody that binds to Delta-like 4 (DLL4) and inhibits said NOTCH signaling pathway; and
   c) said compound is administered by injection.

16. The method of claim 15, wherein said patient is treated by administering a pharmaceutical composition comprising said antibody and a pharmaceutically acceptable carrier.

17. The method of claim 16, wherein said pharmaceutical composition is in unit dosage form.

18. The method of claim 17, wherein said compound is administered intravenously.

19. The method of claim 15, wherein said metabolic syndrome is accompanied by one or more complications selected from the group consisting of: acute myocardial infarction; arterial calcification; valvular calcification; valvular stenosis; restenosis after coronary intervention; accelerated tissue damage or delayed healing after coronary intervention; failure of vein grafts for coronary bypass surgery; stroke and heart failure.

20. The method of claim 15, wherein said metabolic syndrome is accompanied by one or more complications selected from the group consisting of: chronic kidney disease; diabetic nephropathy; vasculitis; retinopathy; and erectile dysfunction.

* * * * *

SEQUENCE LISTING

```
<160> NUMBER OF SEQ ID NOS: 2

<210> SEQ ID NO 1
<211> LENGTH: 20
<212> TYPE: DNA
<213> ORGANISM: Homo sapiens

<400> SEQUENCE: 1
gcttgtttca acaacccttg                                               20

<210> SEQ ID NO 2
```

```
<211> LENGTH: 20
<212> TYPE: DNA
<213> ORGANISM: Homo sapiens

<400> SEQUENCE: 2
atgacacatt cctgcgttga                                              20
```